United States Patent
Yen et al.

(10) Patent No.: US 11,739,110 B2
(45) Date of Patent: Aug. 29, 2023

(54) ORGANIC ELECTROLUMINESCENT MATERIAL AND DEVICE

(71) Applicants: Feng-Wen Yen, Taipei (TW); Tsun-Yuan Huang, Chiayi (TW)

(72) Inventors: Feng-Wen Yen, Taipei (TW); Tsun-Yuan Huang, Chiayi (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 716 days.

(21) Appl. No.: 16/675,195

(22) Filed: Nov. 5, 2019

(65) Prior Publication Data

US 2021/0130383 A1   May 6, 2021

(51) Int. Cl.
*C07D 209/88*   (2006.01)
*C07F 15/00*   (2006.01)
(Continued)

(52) U.S. Cl.
CPC ........ *C07F 15/0033* (2013.01); *C07C 257/18* (2013.01); *C07D 209/88* (2013.01); *C07D 213/78* (2013.01); *C07D 217/26* (2013.01); *H10K 85/342* (2023.02); *H10K 85/615* (2023.02); *H10K 85/654* (2023.02); *H10K 85/6572* (2023.02); *H10K 50/81* (2023.02); *H10K 50/82* (2023.02)

(58) Field of Classification Search
CPC . H01L 51/0085; H01L 51/0072; H01L 51/00; C07D 209/88; H10K 85/342; H10K 85/615; H10K 85/633; C07F 15/003
See application file for complete search history.

(56) References Cited

U.S. PATENT DOCUMENTS

| | | | | |
|---|---|---|---|---|
| 2019/0041699 A1* | 2/2019 | David | ............... | G02F 1/133617 |
| 2019/0252619 A1* | 8/2019 | Tsai | .................... | H01L 51/0067 |
| 2020/0043400 A1* | 2/2020 | Chen | ...................... | H01L 33/08 |

FOREIGN PATENT DOCUMENTS

CN   106543231 A  *  3/2017
CN   108690083 A  *  10/2018
(Continued)

*Primary Examiner* — Younes Boulghassoul
*Assistant Examiner* — Quinton A Brasfield

(57) ABSTRACT

A compound having a first ligand of the following

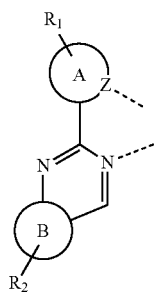

formula (2)

is described. Ring A represents a monocyclic aromatic group or a polycyclic aromatic group. Ring B represents a polycyclic aromatic group. Z is a carbon. Z and the right N are coordinated to a metal to form a five-membered chelate ring. $R_1$ and $R_2$ independently represent mono to a maximum possible number of substitutions, or no substitution.

13 Claims, 2 Drawing Sheets

(51) Int. Cl.
*C07C 257/18* (2006.01)
*C07D 217/26* (2006.01)
*C07D 213/78* (2006.01)
*H10K 85/30* (2023.01)
*H10K 85/60* (2023.01)
*H10K 50/81* (2023.01)
*H10K 50/82* (2023.01)

(56) References Cited

FOREIGN PATENT DOCUMENTS

| CN | 108690084 A | * | 10/2018 | |
|---|---|---|---|---|
| WO | WO-2019221446 A1 | * | 11/2019 | .......... C07F 15/0033 |
| WO | WO-2019221487 A1 | * | 11/2019 | .......... C07F 15/0033 |

* cited by examiner

ORGANIC ELECTROLUMINESCENT MATERIAL AND DEVICE

FIELD

The present invention relates to a compound, and, more specifically, to an organic electroluminescence (hereinafter referred to as organic EL) device using the compound.

BACKGROUND

Organic electroluminescence (organic EL) devices, i.e., organic light-emitting diodes (OLEDs) that make use of organic compounds, are becoming increasingly desirable than before. The devices make use of thin organic films that emit light when voltage is applied across the device. They are becoming an interesting technology for use in applications such as flat panel displays, illumination, or backlighting.

One of the organic compounds, denoted $Ir(piq)_2(acac)$ hereinafter, has the following formula:

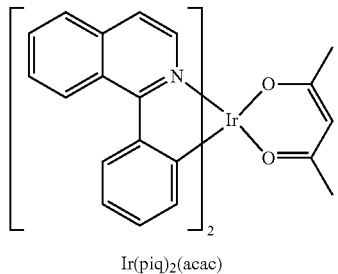

$Ir(piq)_2(acac)$

As used herein, "top" means furthest away from the substrate, while "bottom" means closest to the substrate. Where a second layer is described as formed on or onto a first layer, the second layer is formed further away from substrate. There may be other layers between the second layer and the first layer, unless it is specified that the second layer is "in contact with" the first layer. For example, a cathode may be described as formed onto an anode, even though there are various organic layers in between.

SUMMARY

A compound comprises a first ligand of the following formula:

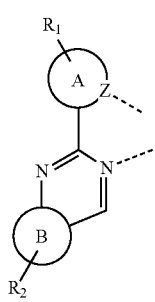

formula (2)

or a tautomer thereof;
wherein ring A represents a monocyclic aromatic group or a polycyclic aromatic group;
wherein ring B represents a polycyclic aromatic group;
wherein Z is a carbon;
wherein Z and the right N are coordinated to a metal to form a five-membered chelate ring;
wherein $R_1$ and $R_2$ independently represent mono to a maximum possible number of substitutions, or no substitution;
wherein $R_1$ and $R_2$ are each independently a hydrogen or a substituent selected from the group consisting of halide, alkyl, alkoxy, aralkyl, heteroaryl, deuterium, cycloalkyl, heteroalkyl, aryl, alkyl, alkoxy, aryloxy, amino, silyl, alkenyl, cycloalkenyl, heteroalkenyl, alkynyl, acyl, carbonyl, carboxylic acids, ester, nitrile, isonitrile, sulfanyl, sulfinyl, sulfonyl, phosphino, and combinations thereof;
wherein two or more of adjacent $R_1$ or $R_2$ substituents are optionally joined or fused into a ring; and
wherein the metal is optionally coordinated to a second ligand.

In selected embodiments, the compound has the following formula:

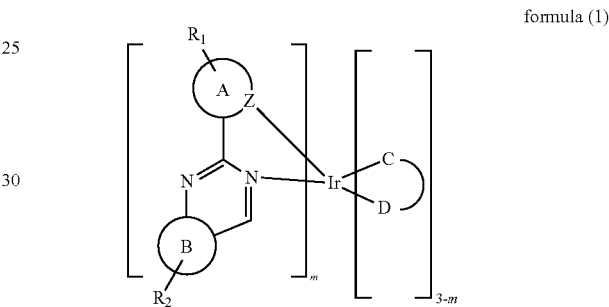

formula (1)

or a tautomer thereof;
wherein Ir is the metal of iridium;
wherein C-D represents the second ligand; and
wherein m represents an integer of 1 to 3.

In selected embodiments, the second ligand is a bidentate ligand having a formula selected from the group consisting of:

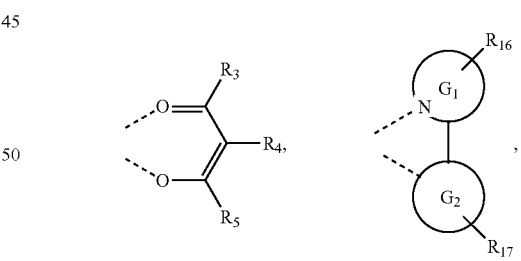

and a tautomer thereof;
wherein $G_1$ represents a hetero-monocyclic aromatic group or a hetero-polycyclic aromatic group having N as the heteroatom;
wherein $G_2$ represents a carbo-monocyclic aromatic group or a carbo-polycyclic aromatic group;
wherein $R_{16}$ and $R_{17}$ independently represent mono to a maximum possible number of substitutions, or no substitution; and
wherein each of $R_{16}$ or $R_{17}$ substitutions are independently selected from the group consisting of halogen, alkyl, alkoxy, aralkyl, heteroaryl, and combinations thereof.

The present invention further discloses an organic EL device. The organic EL device may comprise a cathode, an anode and one or more organic layers formed between the anode and the cathode, wherein at least one of the organic layers comprises the compound of the present invention.

In selected embodiments, the organic electroluminescence device is a panel free of blue wavelengths.

In selected embodiments, the one of the organic layers comprising the compound is an emissive layer emitting orange phosphorescence.

In selected embodiments, the one of the organic layers comprising the compound is an emissive layer emitting green, yellow or red phosphorescence.

In selected embodiments, the organic electroluminescence device is an amber panel.

The present invention further discloses a product for manufacturing a compound of formula (2) in an organic layer of an organic electroluminescence device. The product has the following formula:

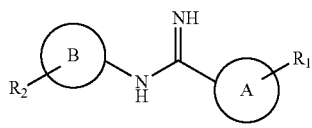

or a tautomer thereof;

wherein ring A represents a monocyclic aromatic group or a polycyclic aromatic group;

wherein ring B represents a polycyclic aromatic group;

wherein $R_1$ and $R_2$ independently represent mono to a maximum possible number of substitutions, or no substitution;

wherein $R_1$ and $R_2$ are each independently a hydrogen or a substituent selected from the group consisting of halide, alkyl, alkoxy, aralkyl, heteroaryl, deuterium, cycloalkyl, heteroalkyl, aryl, alkyl, alkoxy, aryloxy, amino, silyl, alkenyl, cycloalkenyl, heteroalkenyl, alkynyl, acyl, carbonyl, carboxylic acids, ester, nitrile, isonitrile, sulfanyl, sulfinyl, sulfonyl, phosphino, and combinations thereof; and wherein two or more of adjacent $R_1$ or $R_2$ substituents are optionally joined or fused into a ring.

DETAILED DESCRIPTION

Figure 1:
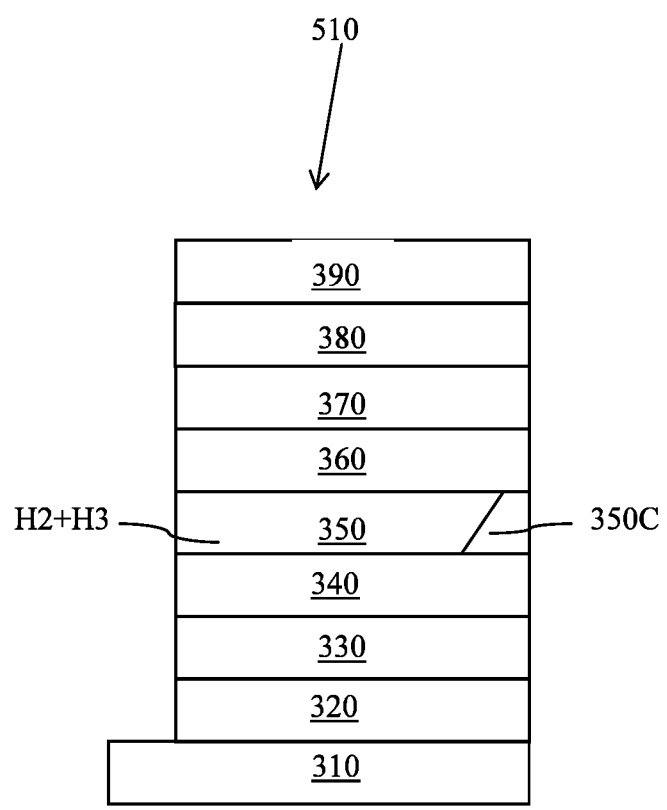
FIG. 1 is a cross-sectional view of a first organic EL device according to a second embodiment of the present invention.

Plural embodiments of the present disclosure are disclosed through drawings. For the purpose of clear illustration, many practical details will be illustrated along with the description below. It should be understood that, however, these practical details should not limit the present disclosure. In other words, in embodiments of the present disclosure, these practical details are not necessary. In addition, for the purpose of simplifying the drawings, some conventional structures and components are simply and schematically depicted in the figures.

It is to be understood that although particular phrases used herein, such as "first", "second", "third", and so on, are used to describe different components, members, regions, layers, and/or sections, these components, members, regions, layers, and/or sections should not be limited by these terms. These phrases are used to distinguish one component, member, region, layer, or section from another component, member, region, layer, or section. In this way, a first component, member, region, layer, and/or section to be described below may be referred to as a second component, member, region, layer, and/or section, without departing from the spirit and scope of the present disclosure.

Spatially relative phrases, such as "onto", "on", "under", "below", "underlying", "beneath", "above", and so on used herein, are used for facilitating description of a relation between one component or feature and another component or feature depicted in the drawings. Therefore, it can be understood that, in addition to directions depicted in the drawings, the spatially relative terms mean to include all different orientations during usage or operations of the device. For example, it is assumed that a device in a figure is reversed upside down, a component described as being "under", "below", or "beneath" another component or feature is oriented "onto" or "on" the other component or feature. Therefore, these exemplary terms "under" and "below" may include orientations above and below. The device may be otherwise oriented (e.g., turned by 180 degrees, or other orientations), and the spatially relative terms used herein should be explained accordingly.

Accordingly, it may be understood that when a component or a layer is referred to as being "onto", "on", "connected to", or "coupled to" another component or another layer, it may be immediately on the other component or layer, or connected to or coupled to the other component or layer, or there may be one or more intermediate components or intermediate layers. Further, it can be understood that when a component or a layer is referred to as being "between" two components or two layers, it may be the only component or layer between the two components or layers, or there may be one or more intermediate components or intermediate layers.

Terminologies used herein are only for the purpose of describing particular embodiments, but not limiting the present disclosure. The singular form of "a" and "the" used herein may also include the plural form, unless otherwise indicated in the context. Accordingly, it can be understood that when there terms "include" or "comprise" are used in the specification, it clearly illustrates the existence of a specified feature, bulk, step, operation, component, and/or member, while not excluding the existence or addition of one or more features, bulks, steps, operations, components, members and/or groups thereof. "And/or" used herein includes any and all combinations of one or more related terms that are listed. When a leading word, such as "at least one of", is added ahead of a component list, it is to describe the entire component list, but not individual components among the list.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "substituent", "substitution" and "substituted" are used interchangeably and refer to a substituent other than H that is bonded to the relevant position, e.g., a carbon or nitrogen. For example, when $R_1$ represents mono-substitution, then one $R_1$ must be other than H (i.e., a substitution). Similarly, when $R_1$ represents di-substitution, then two of $R_1$ must be other than H. Similarly, when $R_1$ represents no substitution, $R_1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum possible number of substitutions in a ring structure will depend on the total number of available valencies in the ring atoms. For example, the upper two-rings of

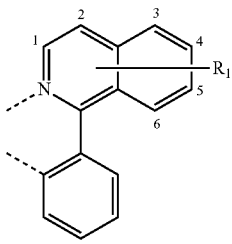

has six available valencies in the ring atoms, so that the maximum possible number of substitutions in the upper ring structure is six. A polycyclic aromatic group or ligand may have two or more rings possible for being substituted. In such a formula, an extended and straight line may be drawn to pass through each of the rings. For example,

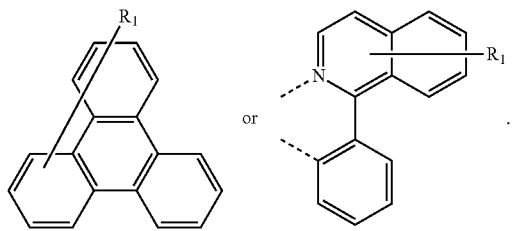

Generally, an organic EL device comprises at least one organic layer disposed between and electrically connected to an anode and a cathode. When an external voltage is applied across the organic EL device, electrons and holes are injected from the cathode and the anode, respectively. Electrons will be injected from a cathode into a LUMO (lowest unoccupied molecular orbital) and holes will be injected from an anode into a HOMO (highest occupied molecular orbital). Subsequently, the electrons recombine with holes in the emissive layer to form excitons and then emit light. When luminescent molecules absorb energy to achieve an excited state, the exciton may either be in a singlet state or a triplet state, depending on how the spins of the electrons and holes have been combined.

The term "hydrogen" refers to a —H radical.

The terms "halogen" and "halide" are used interchangeably and refer to fluorine, chlorine, bromine, or iodine.

The term "trifluoromethyl" refers to a —$CF_3$ radical.

The term "cyano" refers to a —C≡N radical.

The term "nitro" refers to a —$NO_2$ radical.

The term "silyl" refers to a —$Si(R_s)_3$ radical, wherein each $R_s$ can be same or different. $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combinations thereof. Preferred Rs is selected from the group consisting of alkyl, cycloalkyl, aryl, heteroaryl, and combinations thereof.

As used herein, the description "a first integer to a second integer" indicates a group comprising at least a first integer, a second integer, and all integers therebetween, unless otherwise expressively or inherently indicated that the description is a numerical range. The group of the integers is a list of alternatively useable members, just like a Markush group. For example, "1 to 4 atoms" indicates 1, 2, 3 or 4 atoms; and "an integer of 0 to 3" indicates 0, 1, 2 or 3. Note that a "maximum possible number" of substitutions is also an integer. If a maximum possible number of substitutions is 4, the description "mono to the maximum possible number of substitutions" indicates 1, 2, 3 or 4 substitutions.

As used herein, "combinations thereof" indicates that one or more members of the applicable list are combined to form a known or chemically stable arrangement that one of ordinary skill in the art can envision from the applicable list. For example, a monocyclic aromatic group and a polycyclic aromatic group can be combined by being joined through a direct bond, or can be combined to have two carbons common to two adjoining rings (the rings are "fused"); a halogen and alkyl can be combined to form a halogenated alkyl substituent; a halogen, alkyl, and aryl can be combined to form a halogenated arylalkyl; and an alkyl and deuterium can be combined to form a partial or fully deuterated alkyl group. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The term "alkyl" refers to and includes both straight and branched chain alkyl radicals. Preferred alkyl groups are those containing 30 or fewer carbon atoms, preferably 1 to 20 carbon atoms, more preferably 1 to 15 carbon atoms, and most preferably 1 to 12 carbon atoms. Suitable alkyl groups include methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The term "aryl" or "aromatic group" as used herein contemplates monocyclic aromatic groups, polycyclic aromatic groups, and combinations thereof. A polycyclic aromatic group may have two, three, four or more rings in which two carbons are common to two adjoining rings (the rings are "fused") wherein at least one of the fused rings is an aromatic hydrocarbyl, e.g., the other rings can be cycloalkyls, cycloalkenyls, aryl, heterocycles, and/or heteroaryls. Unless otherwise specified, preferred aryl groups are those containing 30 or fewer carbon atoms, preferably 6 to 30 carbon atoms, more preferably 6 to 20 carbon atoms, and most preferably 6 to 12 carbon atoms. Especially preferred is an aryl group having 6 carbons, 10 carbons or 12 carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

Monocyclic aromatic groups contemplate hetero-monocyclic aromatic groups and carbo-monocyclic aromatic groups. Polycyclic aromatic groups contemplate heteropolycyclic aromatic groups and carbo-polycyclic aromatic groups. Hetero-monocyclic aromatic groups are preferably single rings with 5 or 6 ring atoms, and the ring can have from one to six heteroatoms. The hetero-polycyclic aromatic groups can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic groups can have from one to six heteroatoms per ring of the polycyclic aromatic group. Preferred heteroaryl groups are those containing 30 or fewer carbon atoms, preferably 3 to 30 carbon atoms, more preferably 3 to 20 carbon atoms, and most preferably 3 to 12 carbon atoms. Suitable heteroaryl groups include but not limited to dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof.

The term "heteroaryl" as used herein contemplates monocyclic aromatic groups and polycyclic aromatic groups that both include at least one heteroatom. The heteroatoms include, but are not limited to O, S, N, P, B, Si, and Se. In many instances, O, S, Se, N or Si are the preferred heteroatoms. Hetero-monocyclic aromatic groups are preferably single rings with 5 or 6 ring atoms, and the ring can have from one to six heteroatoms. The hetero-polycyclic aromatic groups can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic groups can have from one to six heteroatoms per ring of the polycyclic aromatic group. Preferred heteroaryl groups are those containing 30 or fewer carbon atoms, preferably 3 to 30 carbon atoms, more preferably 3 to 20 carbon atoms, and most preferably 3 to 12 carbon atoms. Suitable heteroaryl groups include but not limited to dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

The term "heterocyclic group" as used herein contemplates aromatic and non-aromatic cyclic radicals. Heteroaromatic cyclic radicals also mean heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "arylene" or "arenediyl" as used herein contemplates a substituent of an organic compound that is derived from an aromatic hydrocarbon (arene) that has had a hydrogen atom removed from two ring carbon atoms, such as phenylene. Unless otherwise specified, preferred arylene groups are those containing 30 or fewer carbon atoms, preferably 6 to 30 carbon atoms, more preferably 6 to 20 carbon atoms, and most preferably 6 to 12 carbon atoms. Especially preferred is an arylene group having 6 carbons, 10 carbons or 12 carbons. Additionally, the arylene group is optionally substituted.

The terms "aralkyl" or "arylalkyl" are used interchangeably and refer to an alkyl group that is substituted with an aryl group. Preferred aralkyl groups are those containing 30 or fewer carbon atoms, preferably 6 to 30 carbon atoms, more preferably 7 to 30 carbon atoms, and most preferably 7 to 13 carbon atoms. Additionally, the aralkyl group is optionally substituted.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, methyl, alkyl, cycloalkyl, aryl, heteroaryl, and combinations thereof.

The term "acyl" refers to a substituted carbonyl radical $(C(O)-R_s)$.

The term "ester" refers to a substituted oxycarbonyl $(-O-C(O)-R_s \text{ or } -C(O)-O-R_s)$ radical.

The term "ether" refers to an $-OR_s$ radical.

The terms "sulfanyl" or "thio-ether" are used interchangeably and refer to a $-SR_s$ radical.

The term "sulfinyl" refers to a $-S(O)-R_s$ radical.

The term "sulfonyl" refers to a $-SO_2-R_s$ radical.

The term "phosphino" refers to a $-P(R_s)_3$ radical, wherein each $R_s$ can be same or different.

The term "tautomer" is a structural isomer (constitutional isomer) of a chemical compound that readily interconvert. This reaction commonly results in the relocation of a proton. The concept of tautomerization is called tautomerism. The chemical reaction interconverting the two is called tautomerization.

It is to be understood that when a molecular fragment is described as being a substituent or otherwise attached to another moiety, its name may be written as if it were a fragment (e.g., phenyl, phenylene, naphthyl, dibenzofuryl, hydrocarbyl, aromatic linker, arylene) or as if it were the whole molecule (e.g., benzene, naphthalene, dibenzofuran, hydrocarbon, aromatic compound, aromatic hydrocarbon). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2,2' positions in a biphenyl, or 1,8 position in a naphthalene, as long as they can form a stable fused ring system.

Material and/or Film Definitions

As used herein, abbreviations refer to materials and/or films as follows:
LiQ: 8-hydroxyquinolato-lithium
Ir(ppy)$_3$: tris(2-phenylpyridine)-iridium
NPB: N,N-Bis(naphthalene-1-yl)-N,N-bis(phenyl)-benzidine
HAT-CN: Dipyrazino[2,3-f:2,3-]quinoxaline-2,3,6,7,10,11-hexacarbonitrile
DMSO: dimethyl sulfoxide
EIL: electron injecting layer
ETL: electron transporting layer
EML: emissive layer
EBL: electron blocking layer
HTL: hole transporting layer
HIL: hole injection layer
ITO: indium tin oxide
EL: electroluminescence The present invention discloses a compound comprising a first ligand of the following formula:

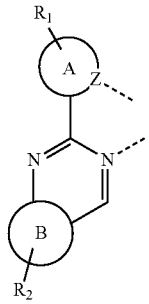

formula (2)

or a tautomer thereof;
wherein ring A represents a monocyclic aromatic group or a polycyclic aromatic group;
wherein ring B represents a polycyclic aromatic group;
wherein Z is a carbon;
wherein Z and the right N are coordinated to a metal to form a five-membered chelate ring;
wherein $R_1$ and $R_2$ independently represent mono to a maximum possible number of substitutions, or no substitution;
wherein $R_1$ and $R_2$ are each independently a hydrogen or a substituent selected from the group consisting of halide, alkyl, alkoxy, aralkyl, heteroaryl, deuterium, cycloalkyl, heteroalkyl, aryl, alkyl, alkoxy, aryloxy, amino, silyl, alkenyl, cycloalkenyl, heteroalkenyl, alkynyl, acyl, carbonyl, carboxylic acids, ester, nitrile, isonitrile, sulfanyl, sulfinyl, sulfonyl, phosphino, and combinations thereof;
wherein two or more of adjacent $R_1$ or $R_2$ substituents are optionally joined or fused into a ring; and
wherein the metal is optionally coordinated to a second ligand.

Figure 2:
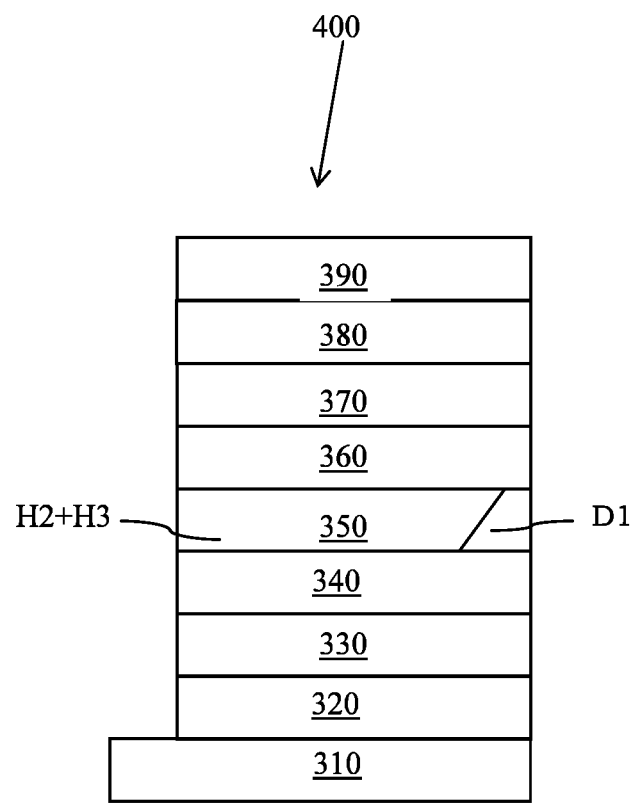
FIG. 2 is a cross-sectional view of an organic EL device without the dopant 350C of FIG. 1.

FIG. 2 is a cross-sectional view of an organic EL device without the organic compound of formula (1) (without 350C of FIG. 1). Referring to FIG. 2, the organic EL device 400 may have a driving voltage of about 4.9 V, a current efficiency of about 16.1 cd/A, or a half-life of about 370 hours, if the dopant D1 is Ir(pig)$_2$(acac).

Referring to FIG. 1, by comprising the compound of the present invention as a dopant 350C, the first organic EL device 510 may have a driving voltage lower than that of the organic EL device 400 (FIG. 2). Moreover, by comprising the compound as a dopant 350C, the first organic EL device 510 of FIG. 1 may have a current efficiency higher than that of the organic EL device 400 (FIG. 2). Furthermore, by comprising the organic compound as a dopant 350C, the first organic EL device 510 of FIG. 1 may have a half-life longer than that of the organic EL device 400 (FIG. 2).

As a dopant 350C of the first organic EL device 510 of FIG. 1, the compound of the present invention may lower the driving voltage to be about 3.6 V to about 4.6 V. Moreover, the compound of the present invention may increase the current efficiency to be about 16.9 cd/A to about 56.3 cd/A.

Furthermore, the compound of the present invention may increase the half-life to be about 380 hours to about 980 hours.

When the dopant 350C is a red dopant (guest), the compound of the present invention may lower the driving voltage to be about 3.5 V to about 4.5 V, increase the current efficiency to be about 16.9 cd/A to about 25.8 cd/A, or increase the half-life to be about 550 hours to about 895 hours. The organic layer comprising the compound is an emissive layer emitting red phosphorescence.

When the dopant 350C is a green dopant (guest), the compound of the present invention may lower the driving voltage to be about 3.8 V to about 4.0 V, increase the current efficiency to be about 49.8 cd/A to about 56.3 cd/A, or increase the half-life to be about 870 hours to about 980 hours. The organic layer comprising the compound is an emissive layer emitting green phosphorescence.

When the dopant 350C is a yellow dopant (guest), the compound of the present invention may lower the driving voltage to be about 4.3 V to about 4.6 V, increase the current efficiency to be about 42.1 cd/A to about 46.3 cd/A, or increase the half-life to be about 380 hours to about 470 hours. The organic layer comprising the compound is an emissive layer emitting yellow phosphorescence.

In selected embodiments, each of $R_1$ and $R_2$ is independently selected from the group consisting of alkyl group having 30 or fewer carbon atoms, alkoxy having 30 or fewer carbon atoms, aryl having 30 or fewer carbon atoms, aralkyl having 30 or fewer carbon atoms, heteroaryl having 30 or fewer carbon atoms, and combinations thereof.

In selected embodiments, $R_1$ and $R_2$ independently represent mono, di, tri, tetra, penta, or hexa substitutions, or no substitution.

In selected embodiments, the first ligand has a formula selected from the group consisting of:

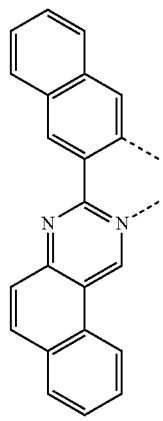

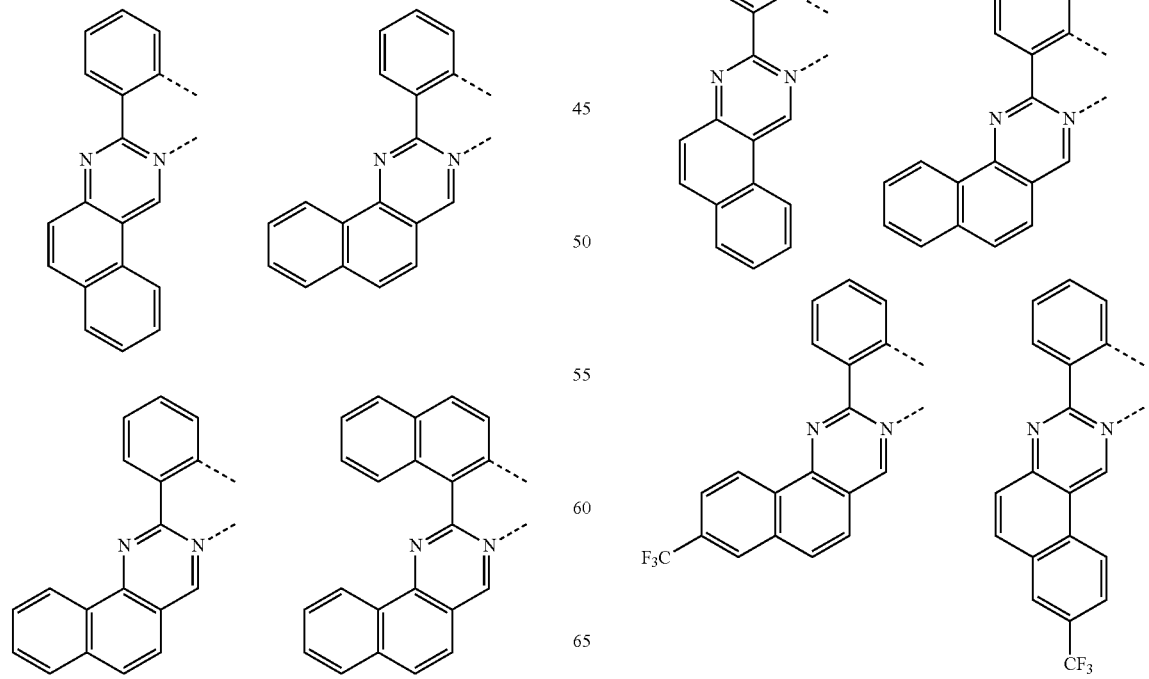

-continued

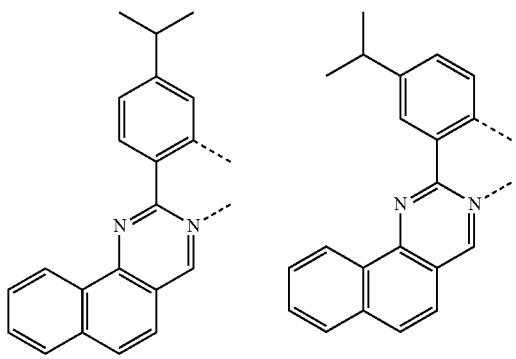

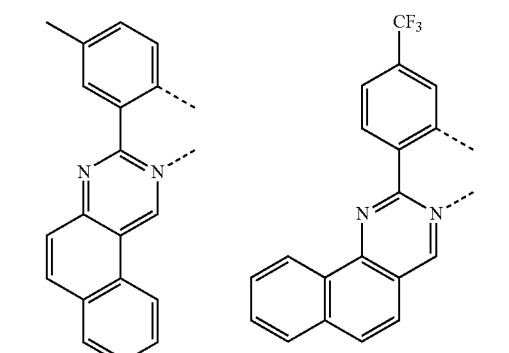

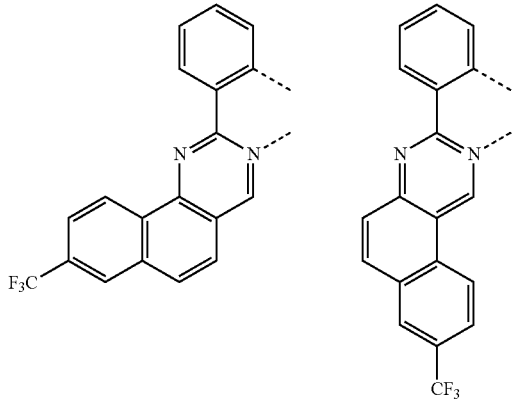

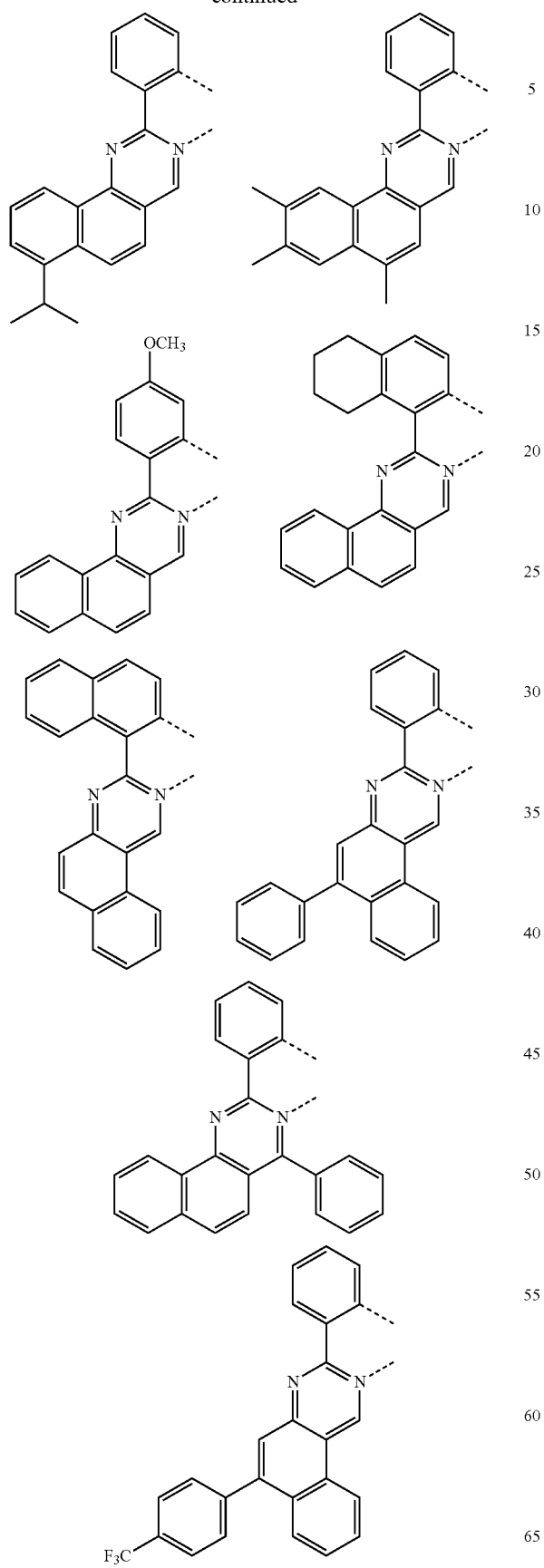
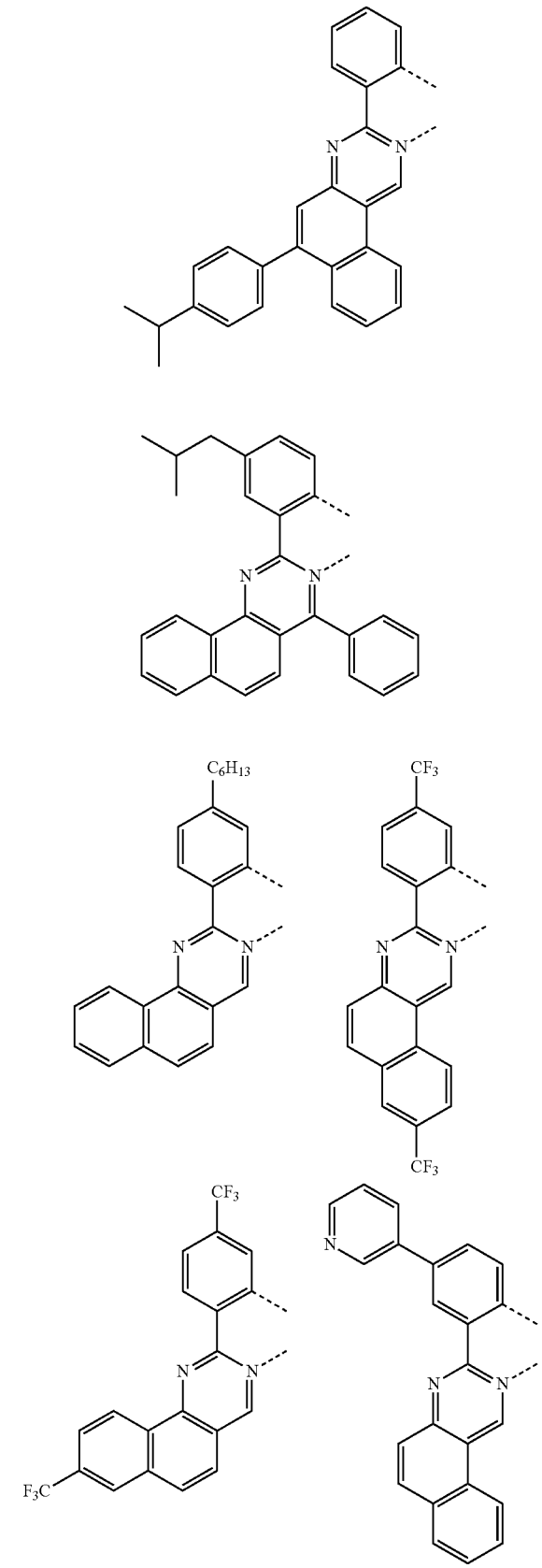

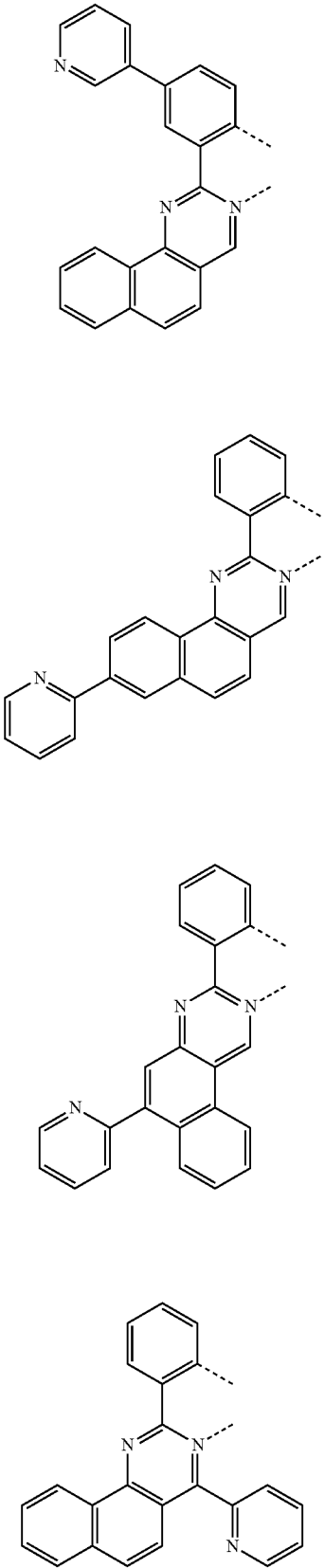
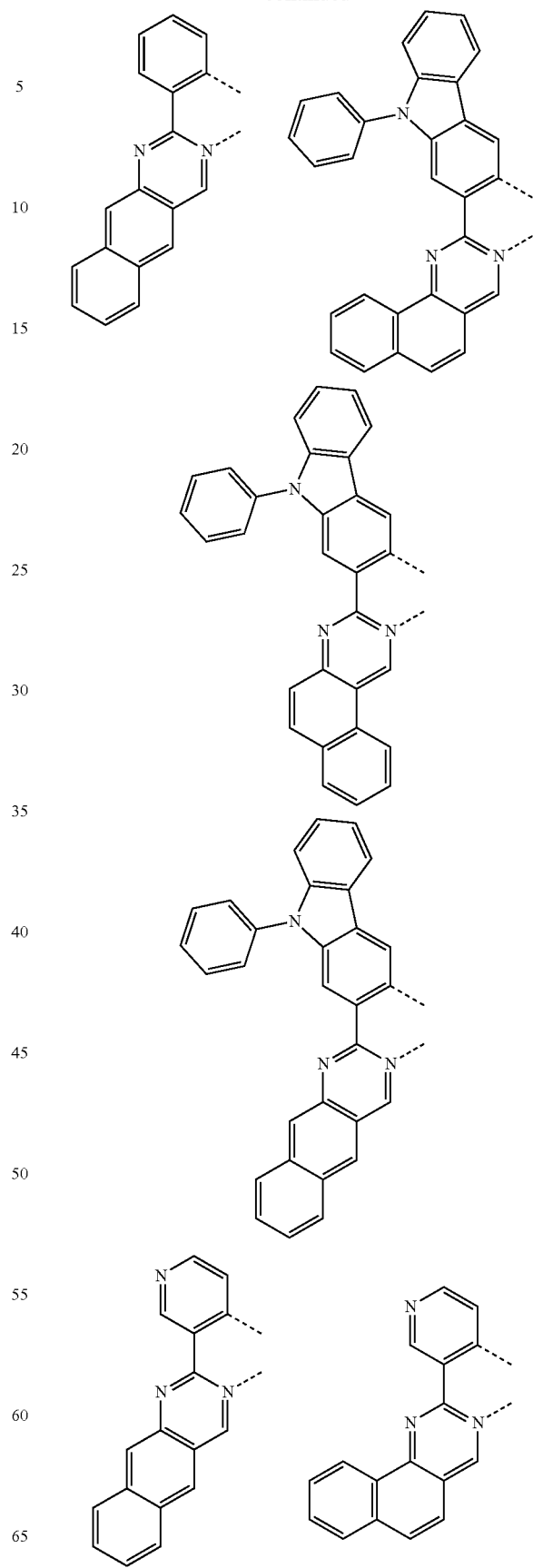

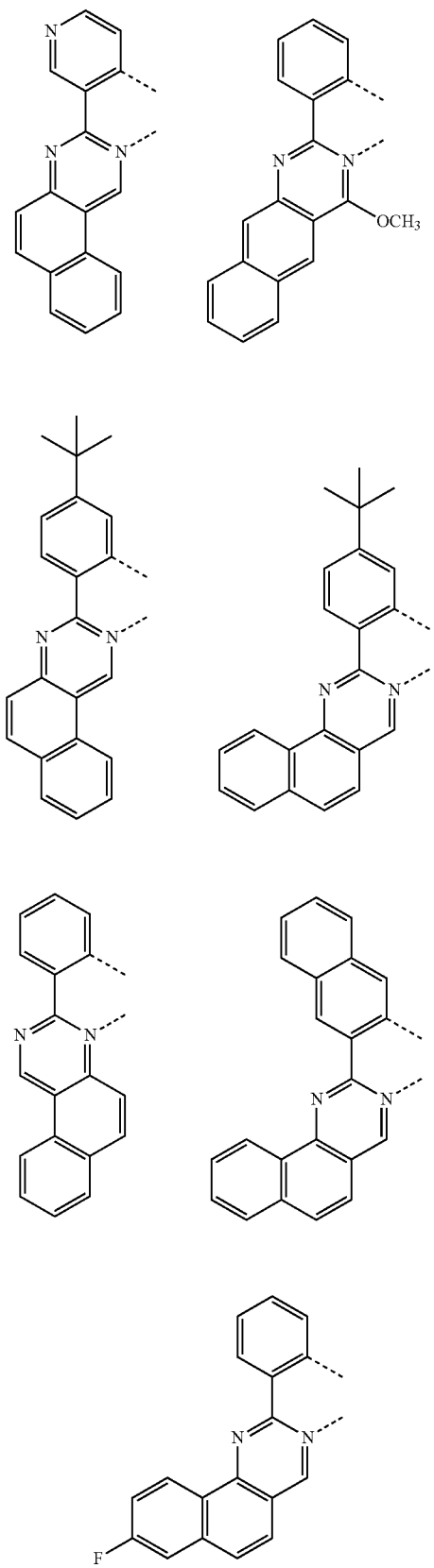
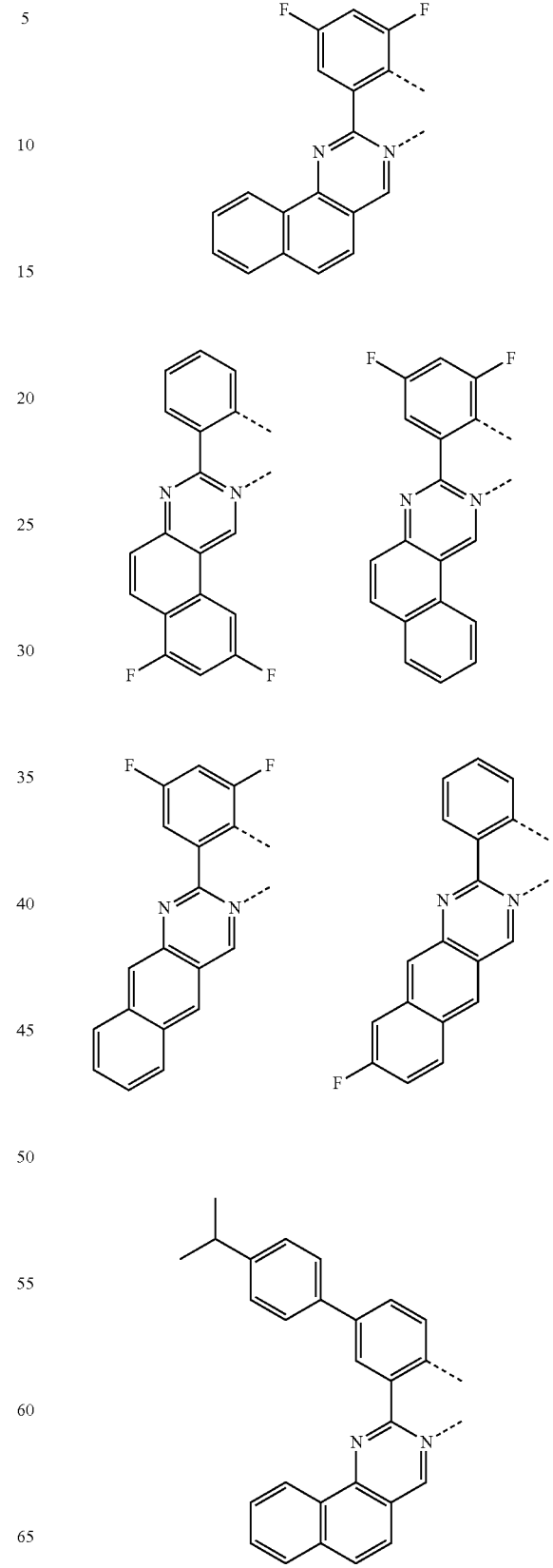

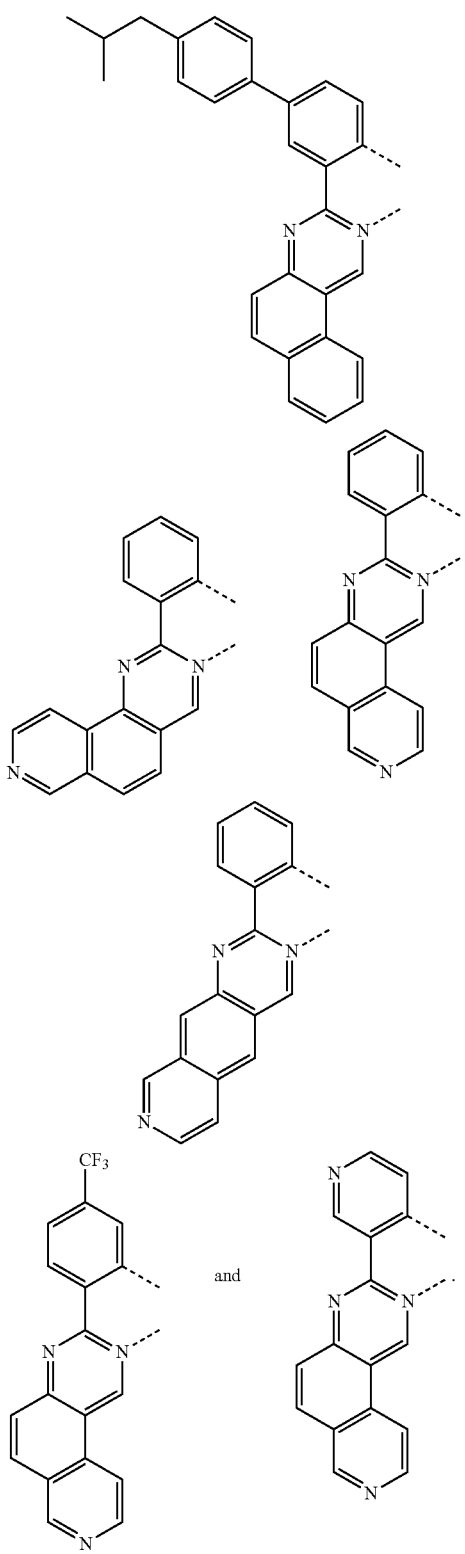

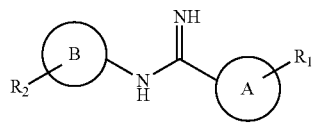

or a tautomer thereof;

wherein ring A represents a monocyclic aromatic group or a polycyclic aromatic group;

wherein ring B represents a polycyclic aromatic group;

wherein $R_1$ and $R_2$ independently represent mono to a maximum possible number of substitutions, or no substitution;

wherein $R_1$ and $R_2$ are each independently a hydrogen or a substituent selected from the group consisting of halide, alkyl, alkoxy, aralkyl, heteroaryl, deuterium, cycloalkyl, heteroalkyl, aryl, alkyl, alkoxy, aryloxy, amino, silyl, alkenyl, cycloalkenyl, heteroalkenyl, alkynyl, acyl, carbonyl, carboxylic acids, ester, nitrile, isonitrile, sulfanyl, sulfinyl, sulfonyl, phosphino, and combinations thereof; and wherein two or more of adjacent $R_1$ or $R_2$ substituents are optionally joined or fused into a ring.

The compound manufactured by the product comprises the first ligand of the following formula:

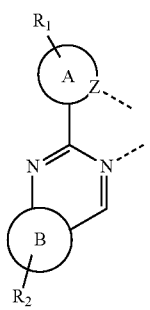

formula (2)

or a tautomer thereof;

wherein Z is a carbon; and wherein Z and the right N are coordinated to a metal to form a five-membered chelate ring.

The product and the compound have the same essential structural element. Their basic chemical structures are the same or their chemical structures are technically closely inter-related. The product incorporates an essential structural element into the compound.

The product and the compound of formula (2) are technically inter-related. The compound is manufactured directly from the product by, for example, formula (2)

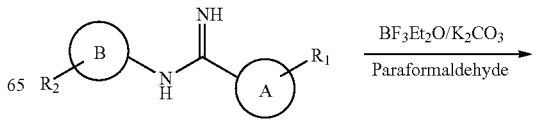

The present invention further discloses a product for manufacturing a compound of formula (2) in an organic layer of an organic electroluminescence device. The product has the following formula:

-continued

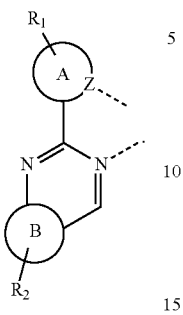

A mixture of the product, Boron trifluoride diethyl etherate, Potassium carbonate, Paraformaldehyde, and DMSO may be sealed under $O_2$ and stirred at about 140° C. for about 24 hrs. After the reaction finished, the mixture is allowed to cool to room temperature. The solution is extracted with dichloromethane and water. The organic layer is dried with anhydrous magnesium sulfate. The solvent is then evaporated under reduced pressure. The residue is purified by column chromatography on silica, to manufacture the compound of formula (2).

In some selected embodiments, the product may have a formula selected from the group consisting of:

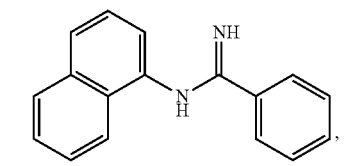

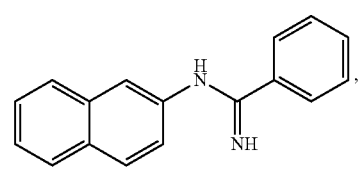

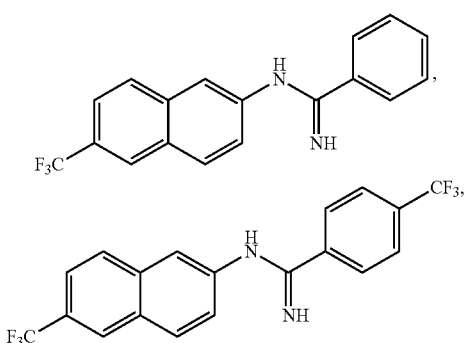

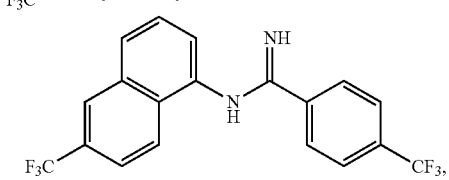

-continued

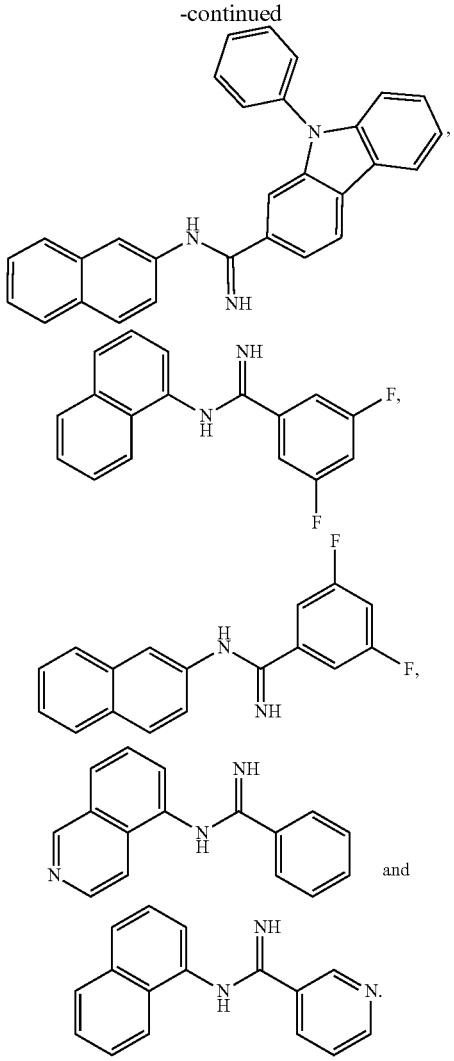

and

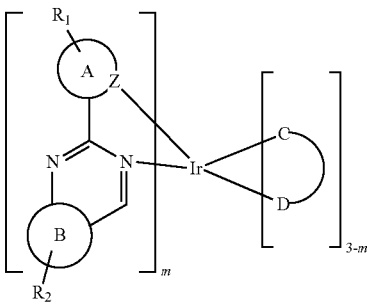

In selected embodiments, the compound has the following formula:

formula (1)

or a tautomer thereof;
wherein Ir is the metal of iridium;
wherein C-D represents the second ligand; and
wherein m represents an integer of 1 to 3.

In selected embodiments, the second ligand is a bidentate ligand of the following formula:

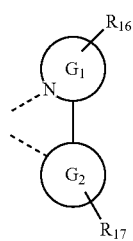

or a tautomer thereof;

wherein $G_1$ represents a hetero-monocyclic aromatic group or a hetero-polycyclic aromatic group having N as the heteroatom;

wherein $G_2$ represents a carbo-monocyclic aromatic group or a carbo-polycyclic aromatic group;

wherein $R_{16}$ and $R_{17}$ independently represent mono to a maximum possible number of substitutions, or no substitution; and wherein each of $R_{16}$ or $R_{17}$ substitutions are independently selected from the group consisting of halogen, alkyl, alkoxy, aralkyl, heteroaryl, and combinations thereof.

In selected embodiments, the second ligand is a bidentate ligand having one of the following formulae:

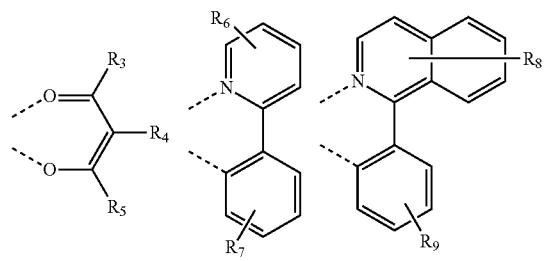

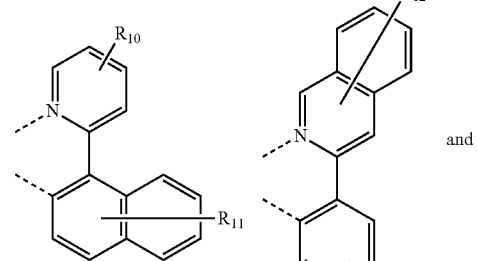

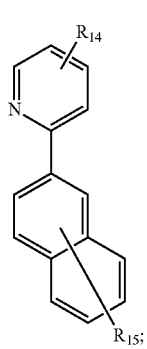

wherein $R_3$ to $R_{15}$ independently represent mono, di, tri, tetra, penta, or hexa substitutions, or no substitution; and wherein each of $R_3$ to $R_{15}$ substitutions are independently selected from the group consisting of halogen, alkyl, alkoxy, aralkyl, heteroaryl, and combinations thereof.

In selected embodiments, each of $R_3$ to $R_{15}$ is independently selected from the group consisting of hydrogen, alkyl having 30 or fewer carbon atoms, alkoxy having 30 or fewer carbon atoms, aryl having 30 or fewer carbon atoms, aralkyl having 30 or fewer carbon atoms, heteroaryl having 30 or fewer carbon atoms, and combinations thereof.

In selected embodiments, each of $R_3$ to $R_{15}$ substitutions are independently selected from the group consisting of a halogen, a methyl group, an isopropyl group, an isobutyl group, a cyclopentyl group, a hexyl group, a cyclohexyl group, a phenyl group, and combinations thereof.

The present invention further discloses an organic EL device. The organic EL device may comprise a cathode, an anode and one or more organic layers formed between the anode and the cathode. At least one of the organic layers comprises the compound of the present invention.

In selected embodiments, the organic electroluminescence device is a panel free of blue wavelengths.

In selected embodiments, the one of the organic layers comprising the compound is an emissive layer emitting orange phosphorescence.

In selected embodiments, the one of the organic layers comprising the compound is an emissive layer emitting green, yellow or red phosphorescence.

In selected embodiments, the organic electroluminescence device is an amber panel.

The organic electroluminescence device may be a lighting panel.

The organic electroluminescence device may be a backlight panel.

The compound of the present invention may be one of the following compounds:

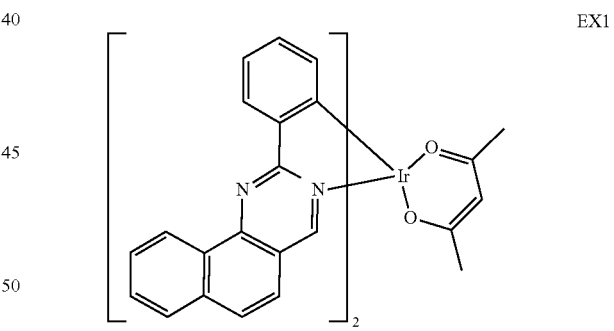

EX1

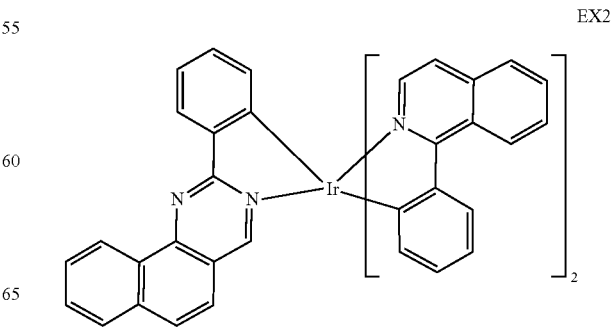

EX2

EX3
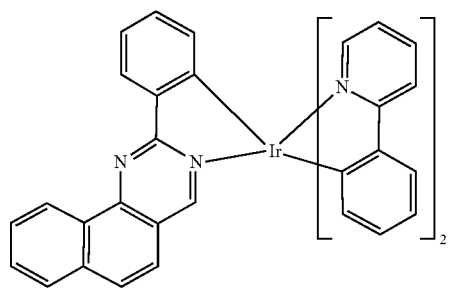
EX4
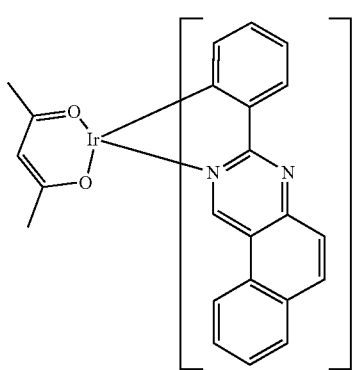
EX5
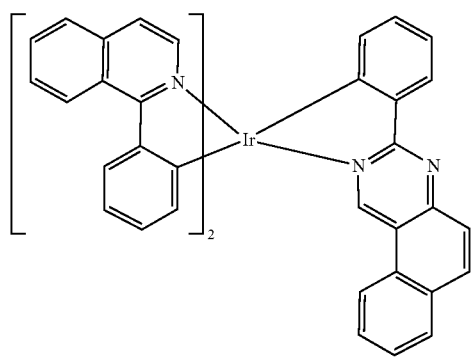
EX6
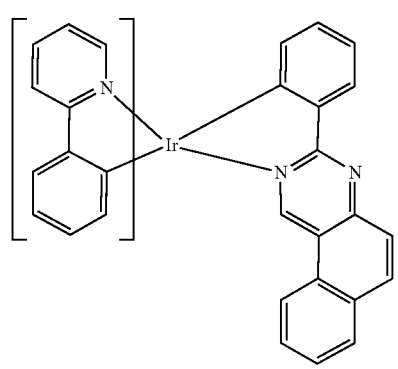
EX7
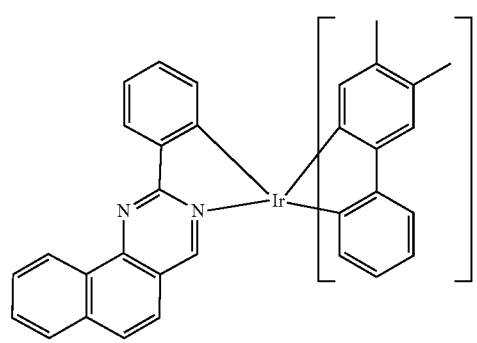
EX8
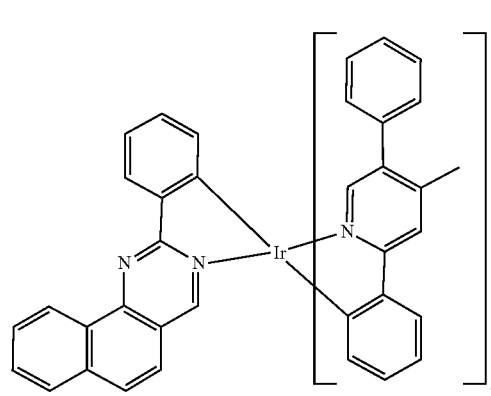
EX9
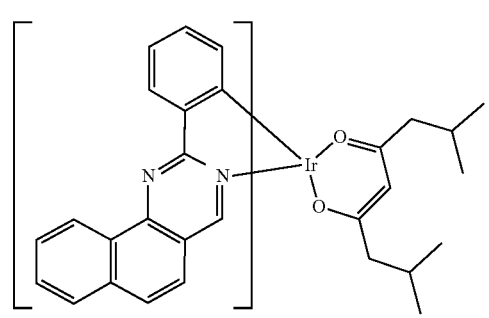
EX10
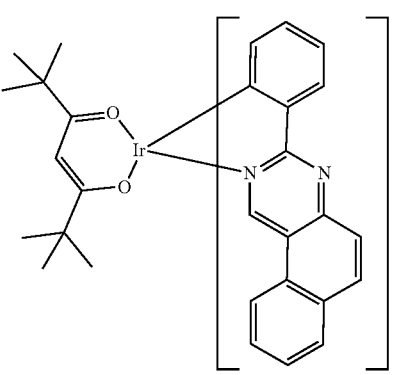

-continued
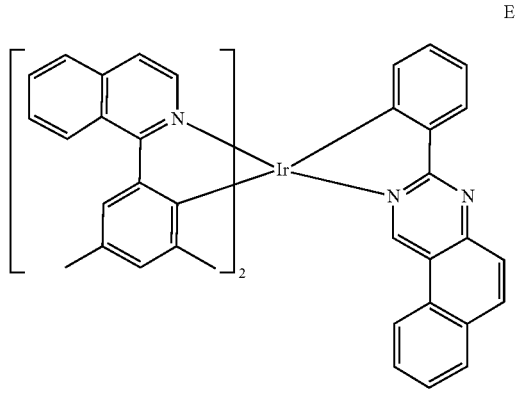 EX11
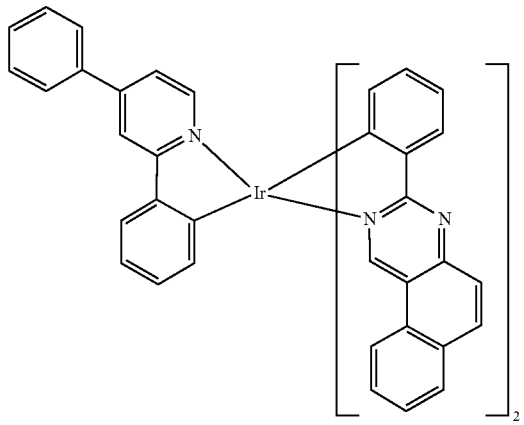 EX12
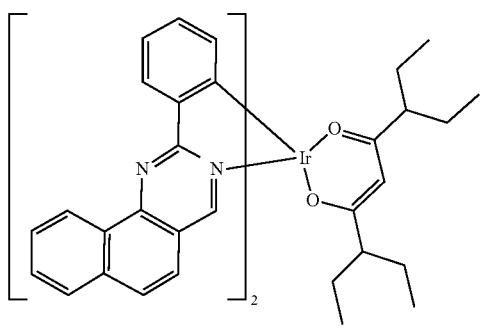 EX13
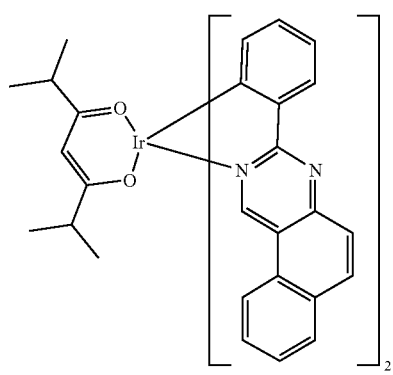 EX14
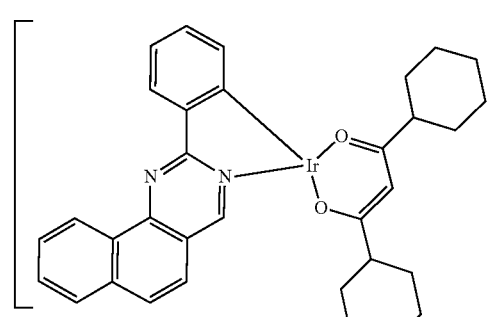 EX15
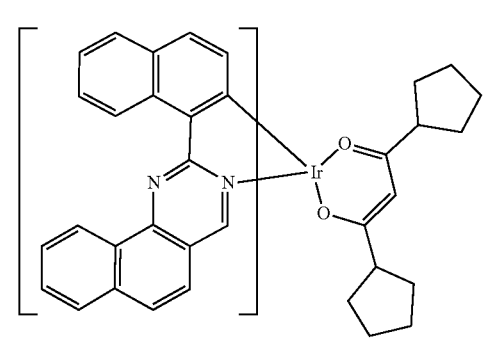 EX16
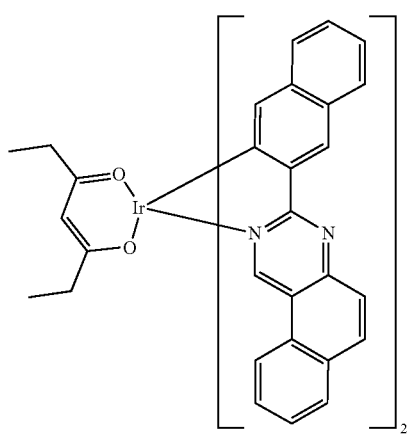 EX17
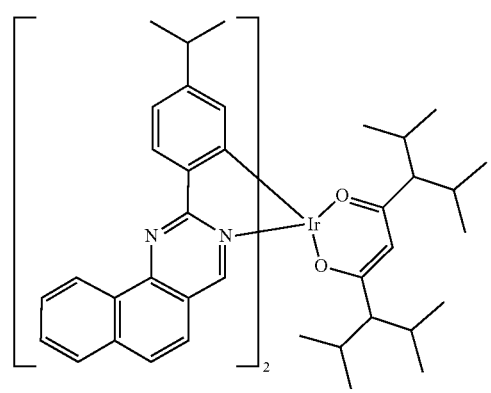 EX18

-continued
EX19
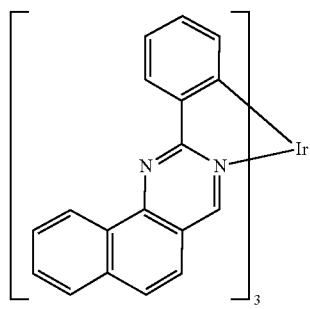
EX20
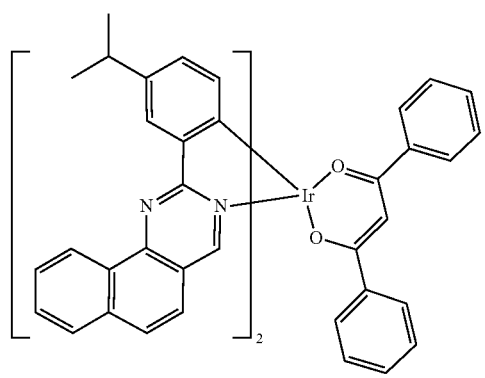
EX21
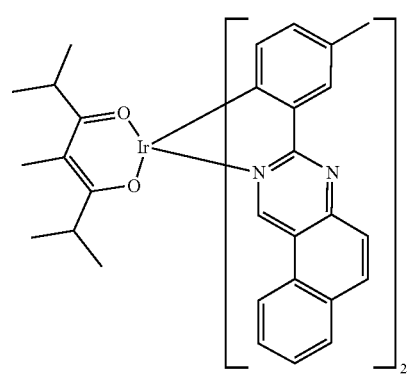
EX22
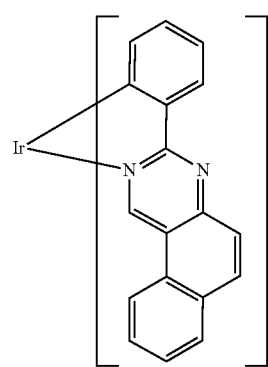
EX23
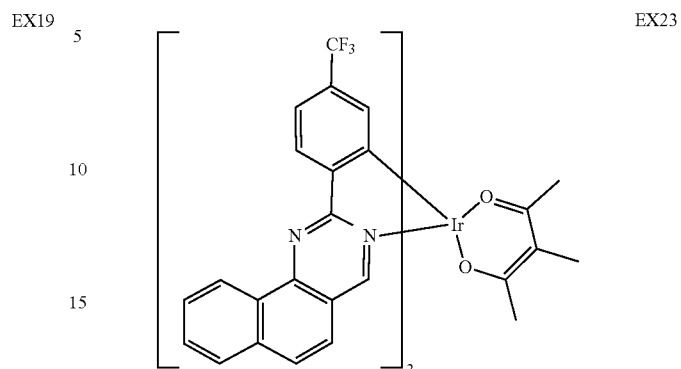
EX24
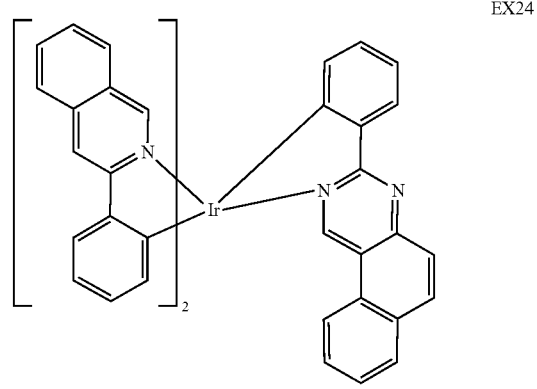
EX25
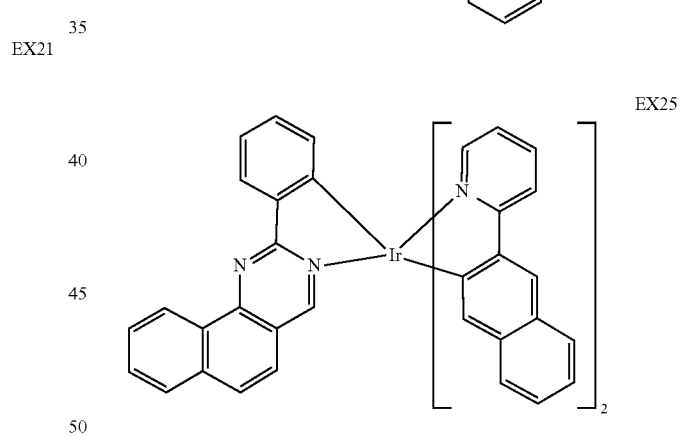
EX26
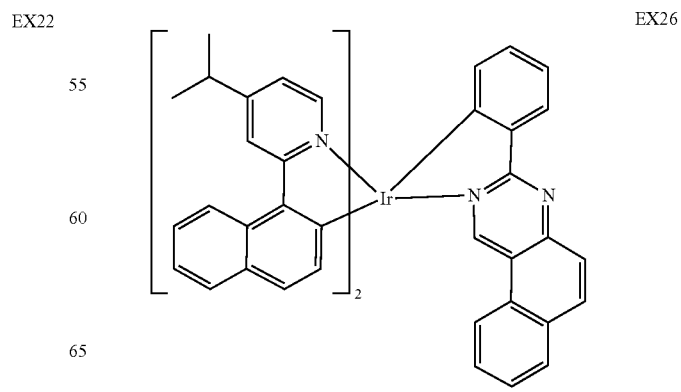

-continued
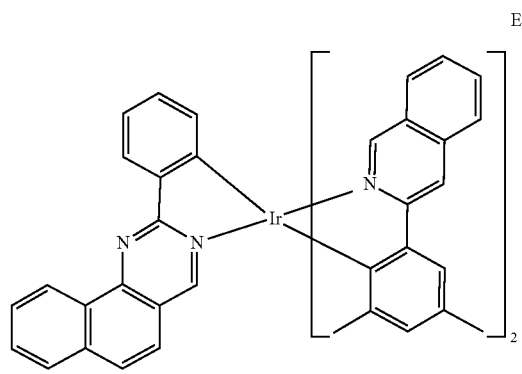
EX27
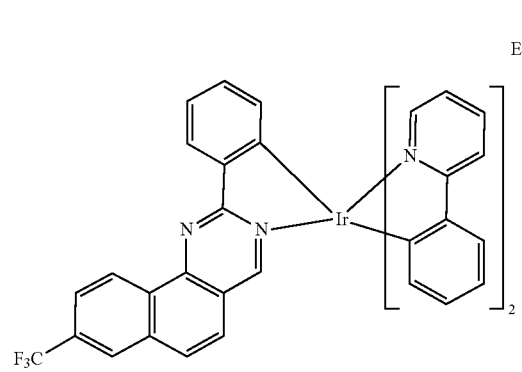
EX28
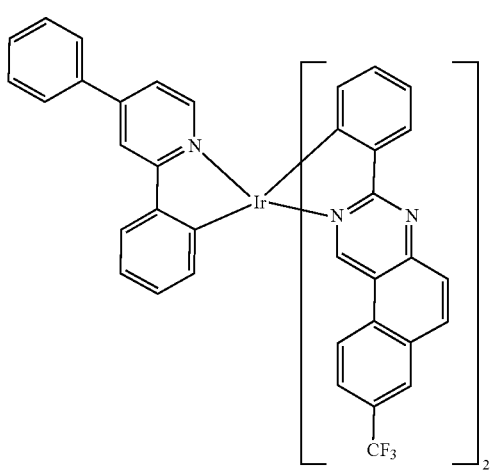
EX29
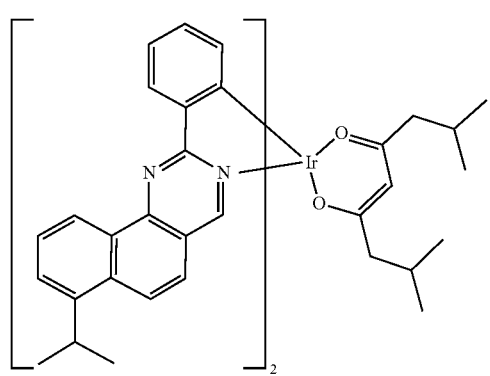
EX30
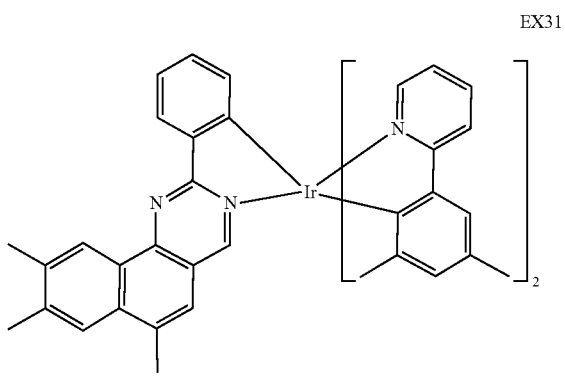
EX31
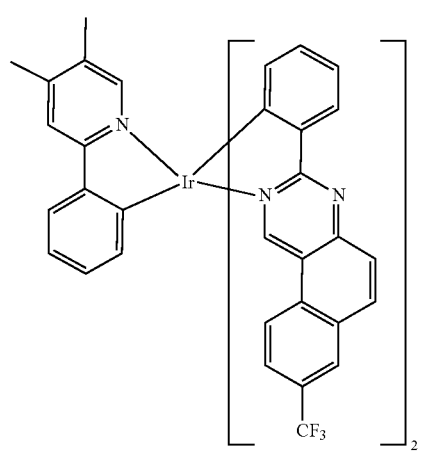
EX32
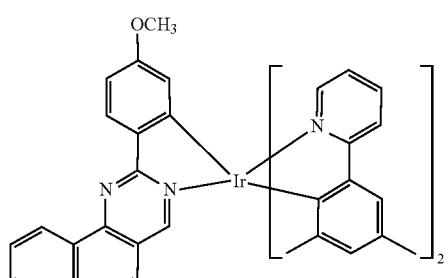
EX33
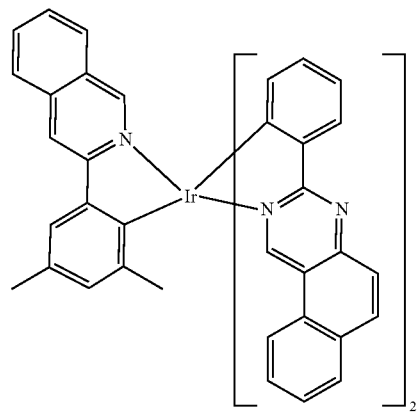
EX34

EX35
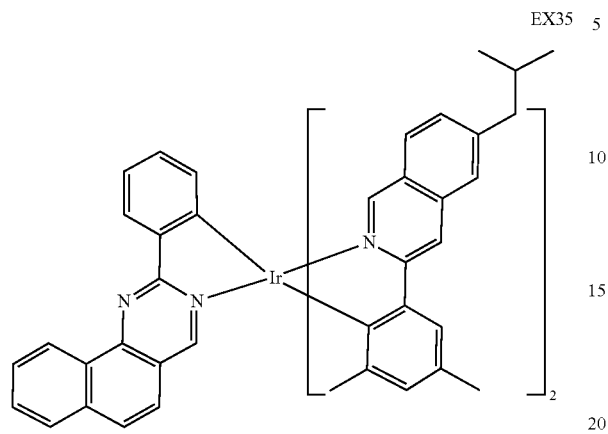
EX36
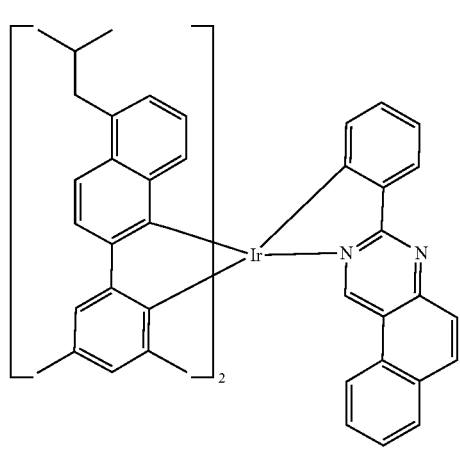
EX37
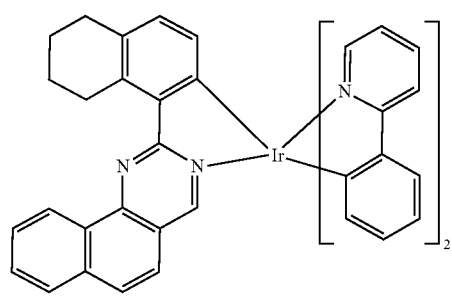
EX38
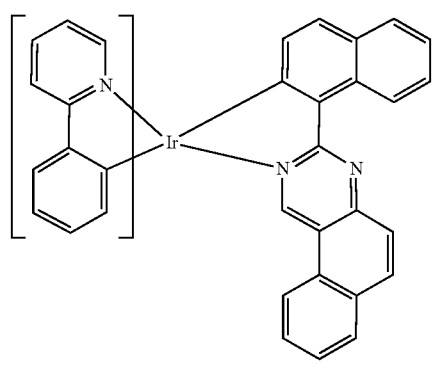
EX39
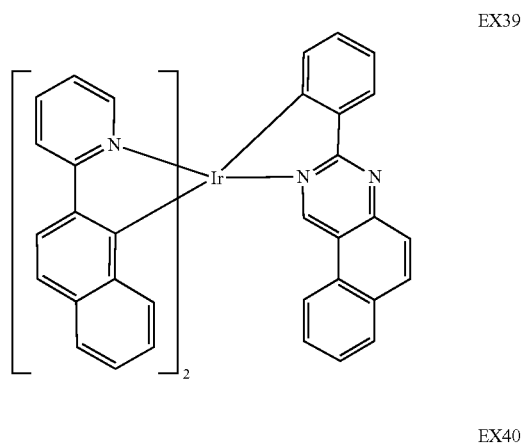
EX40
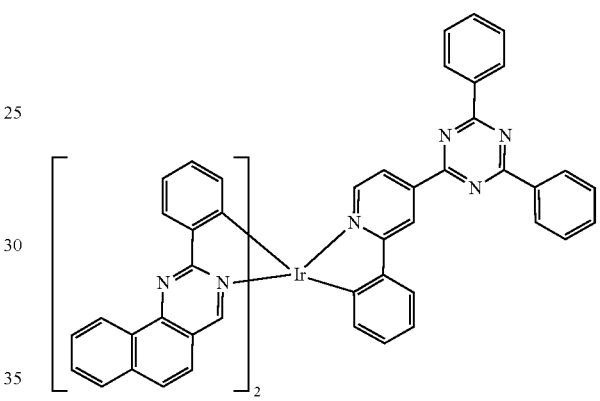
EX41
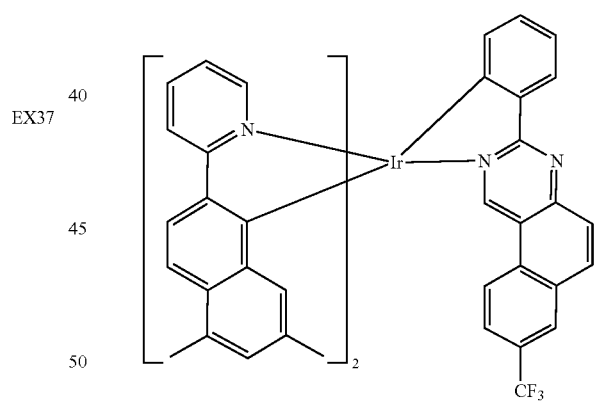
EX42
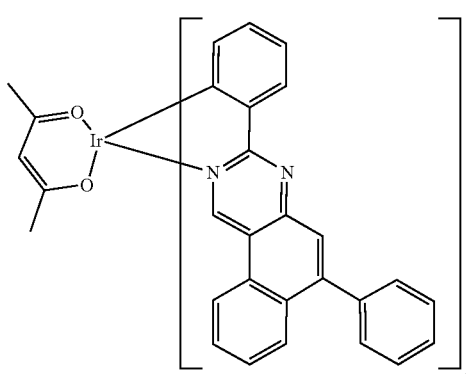

-continued
EX43
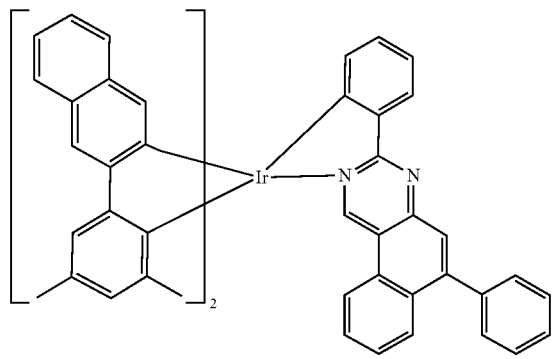
EX44
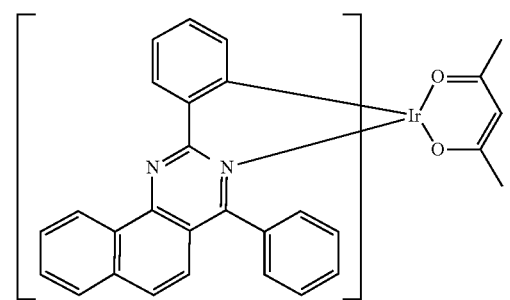
EX45
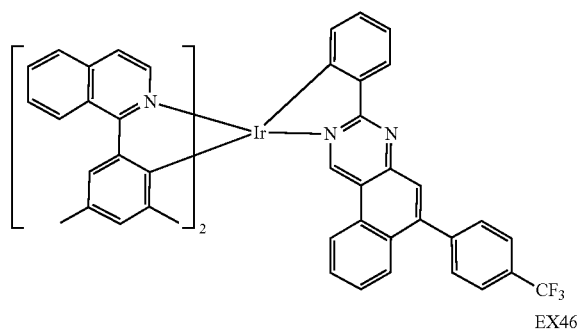
EX46
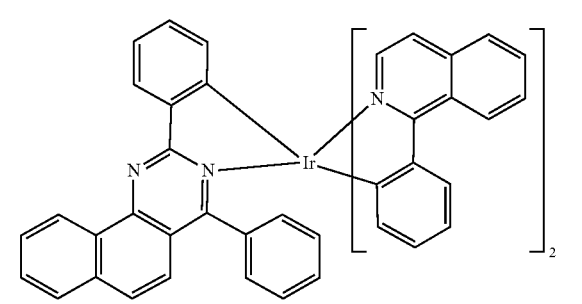
EX47
EX48
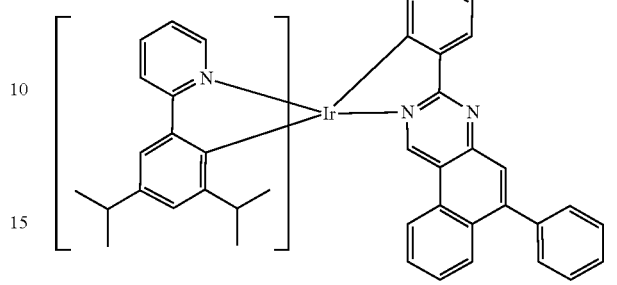
EX49
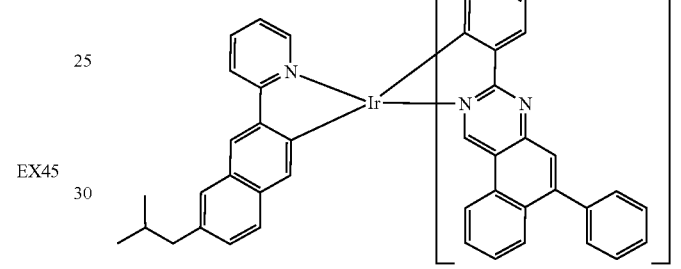
EX50
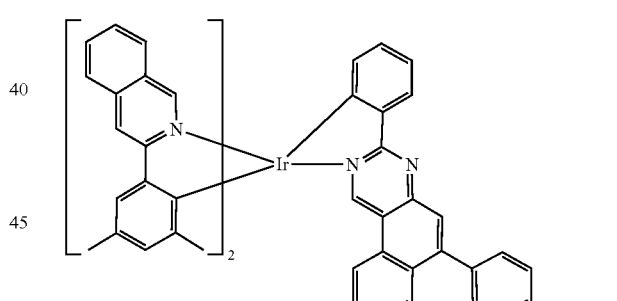
EX51
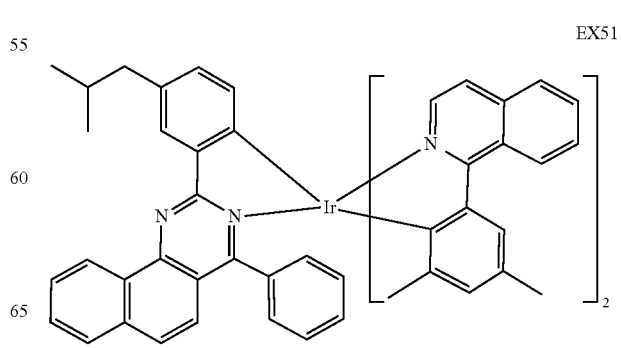

EX52 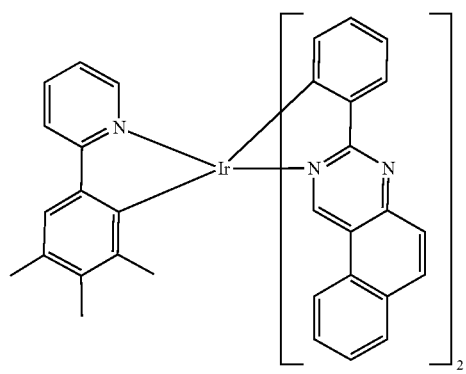
EX53 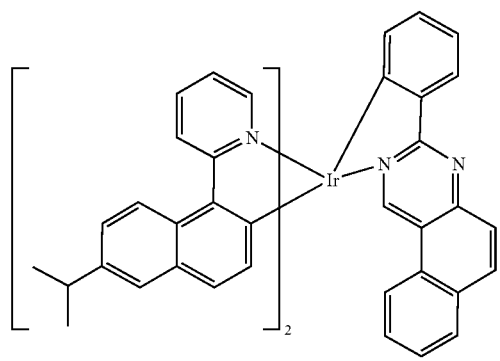
EX54 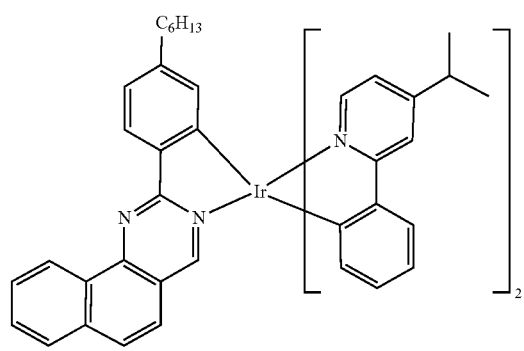
EX55 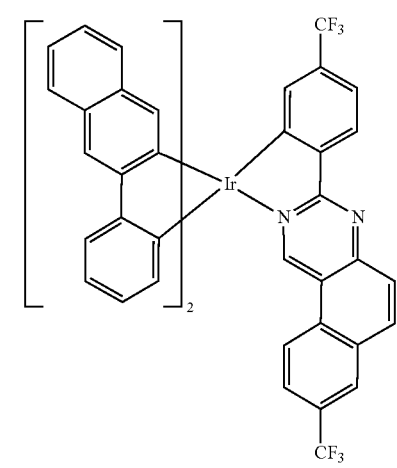
EX56 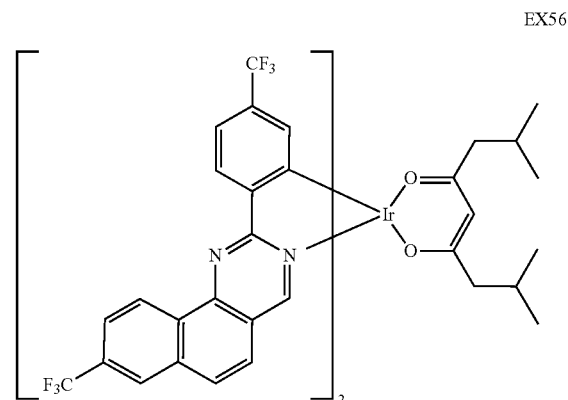
EX57 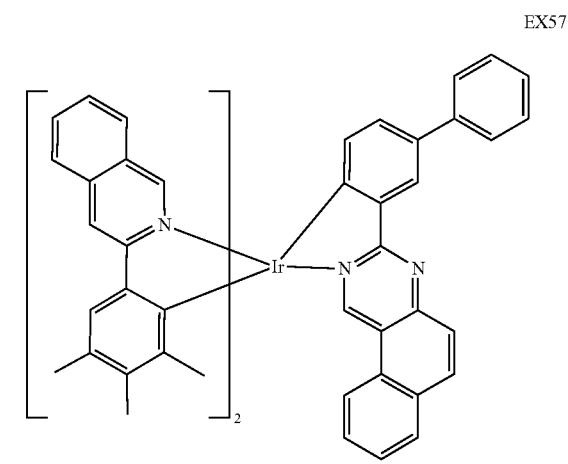
EX58 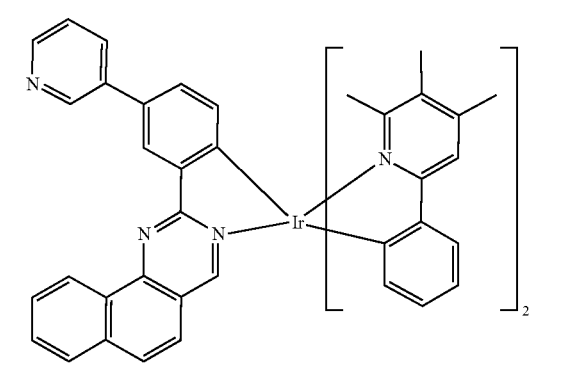
EX59 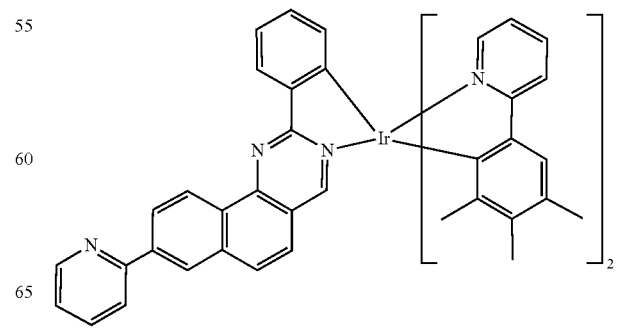

EX60
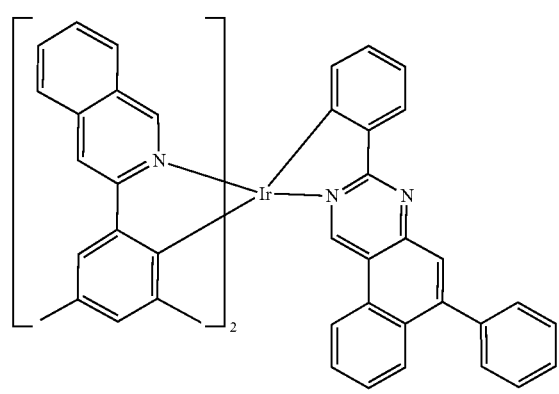
EX61
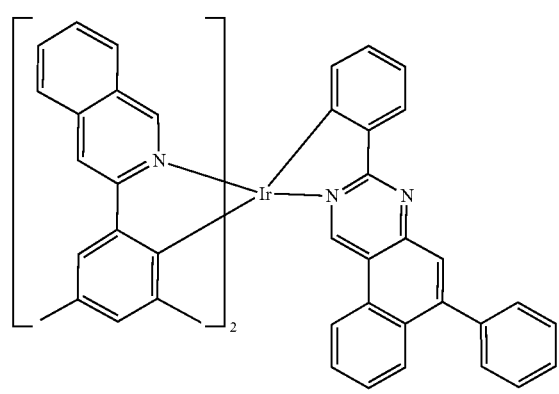
EX62
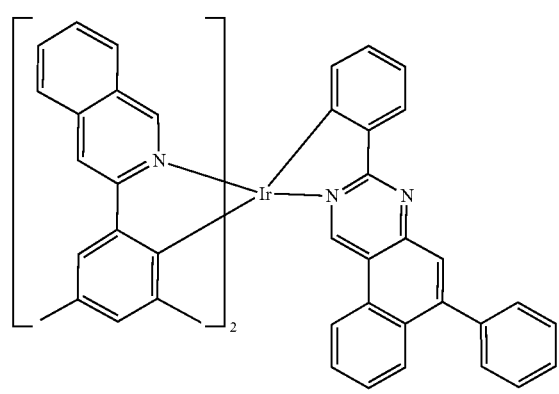
EX63
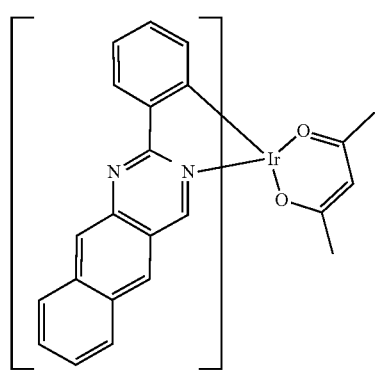
EX64
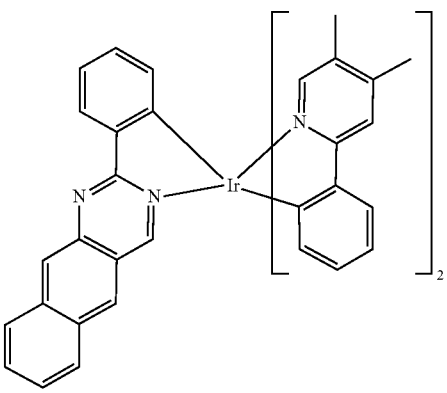
EX65
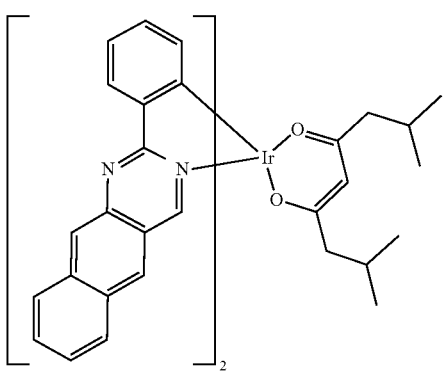
EX66
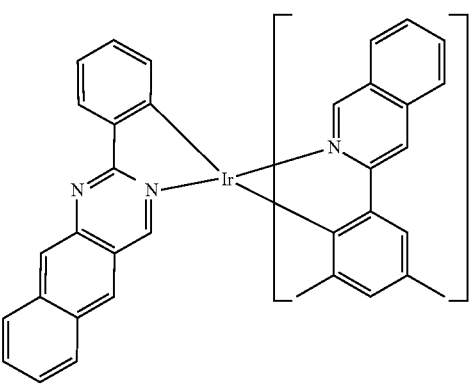
EX67
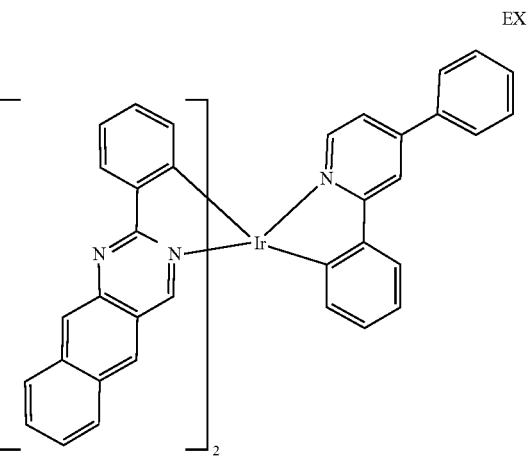

-continued
EX68
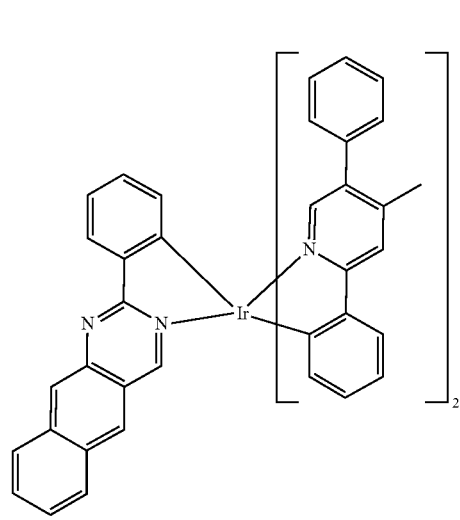
EX69
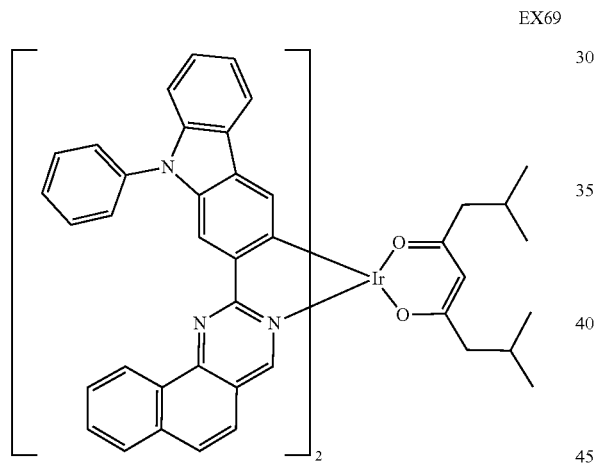
EX70
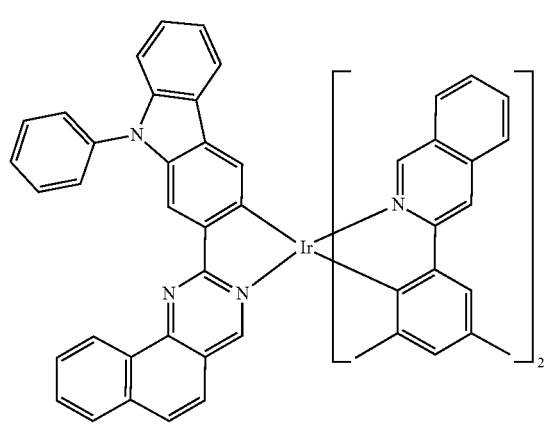
-continued
EX71
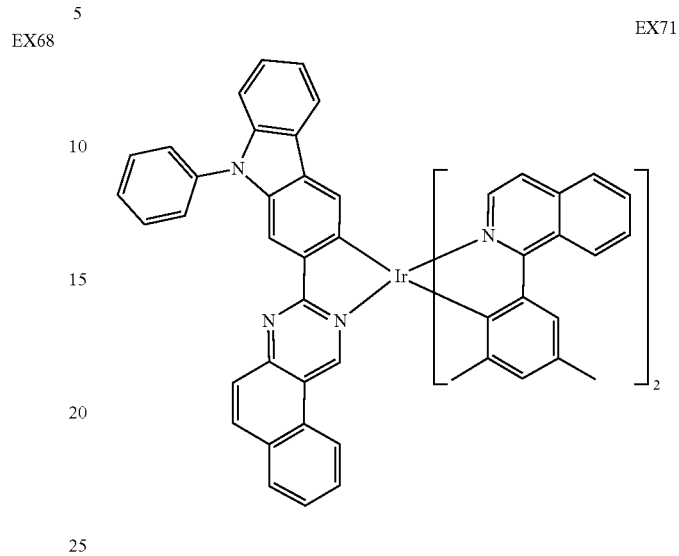
EX72
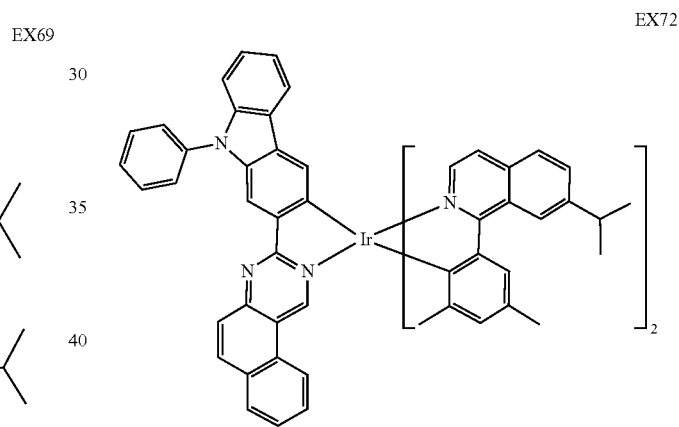
EX73
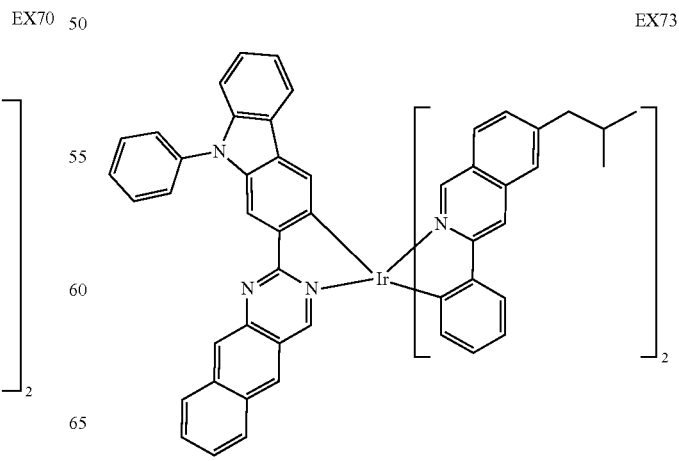

EX74
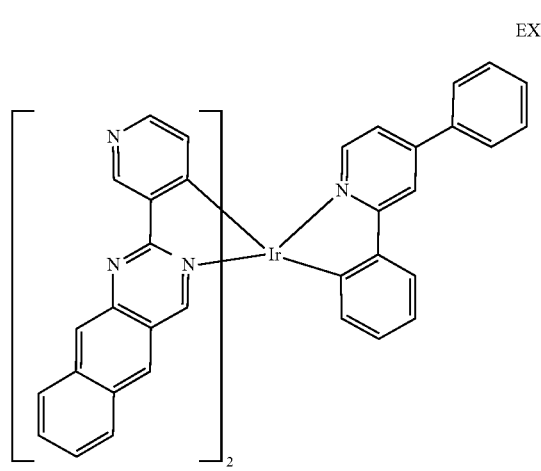
EX78
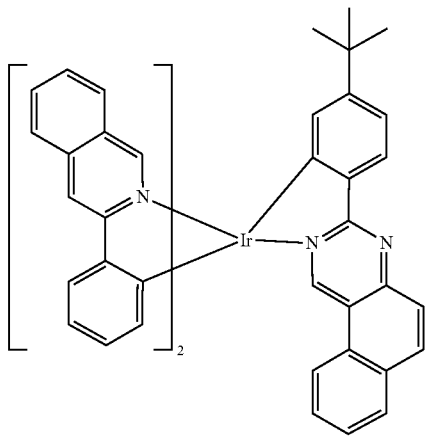
EX75
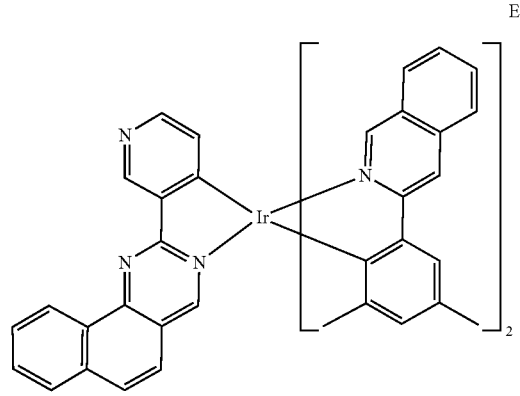
EX76
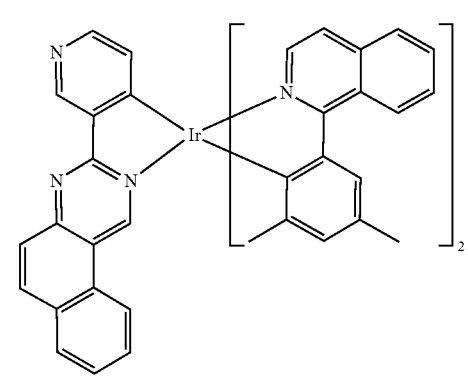
EX79
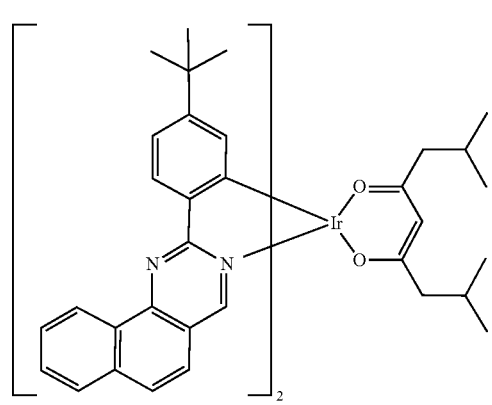
EX77
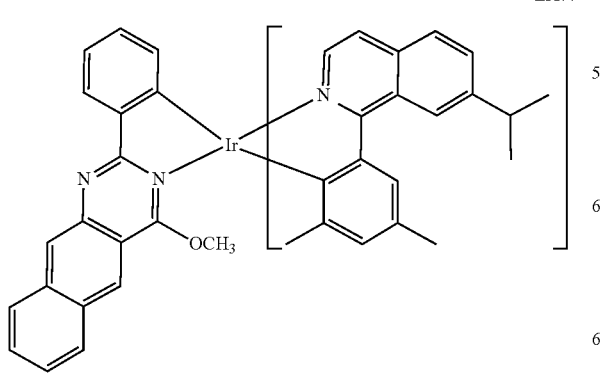
EX80
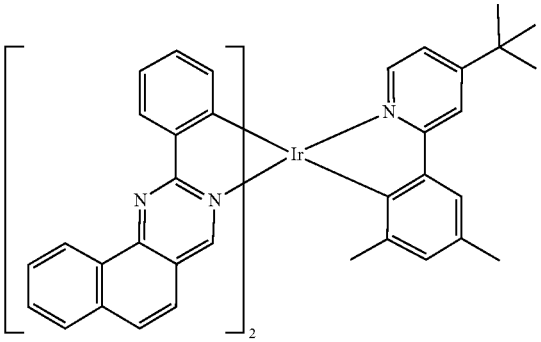

EX81
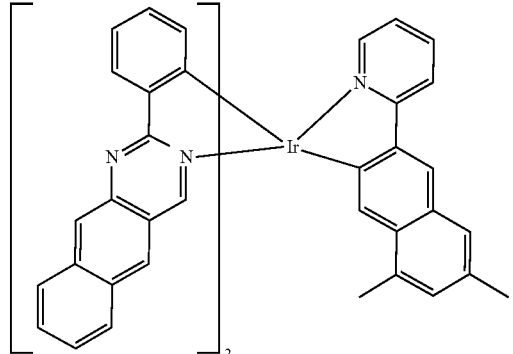
EX84
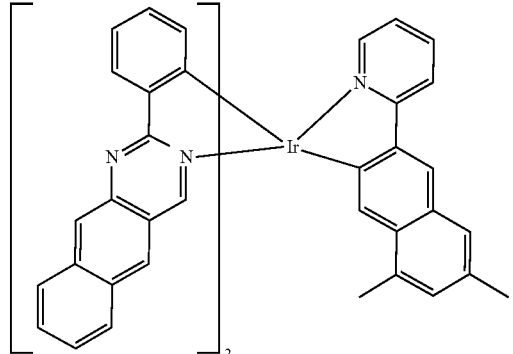
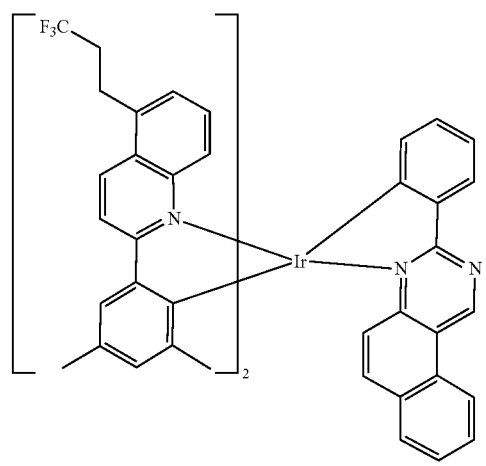
EX82
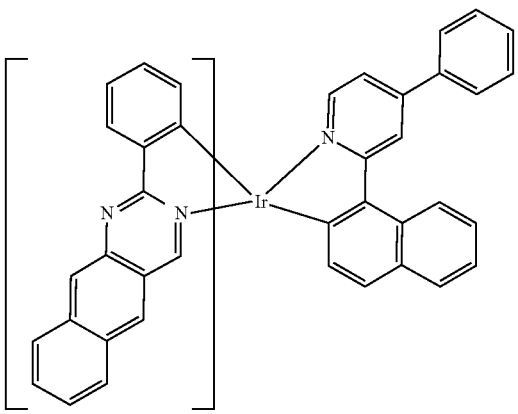
EX85
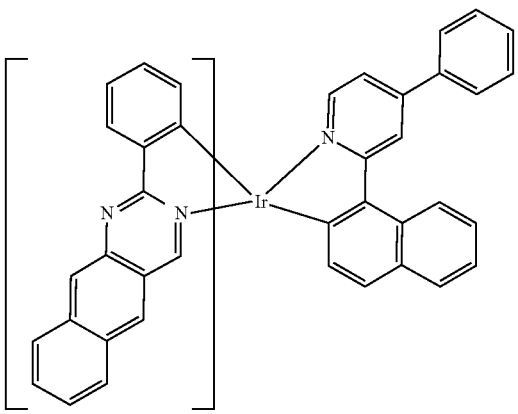
EX83
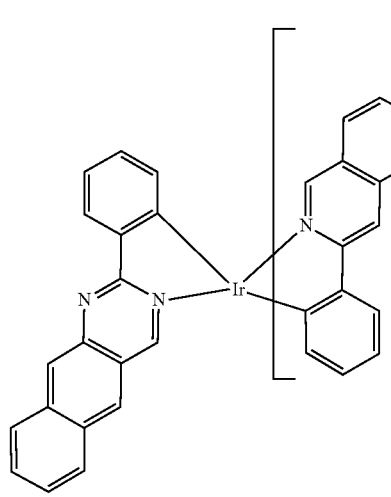
EX86
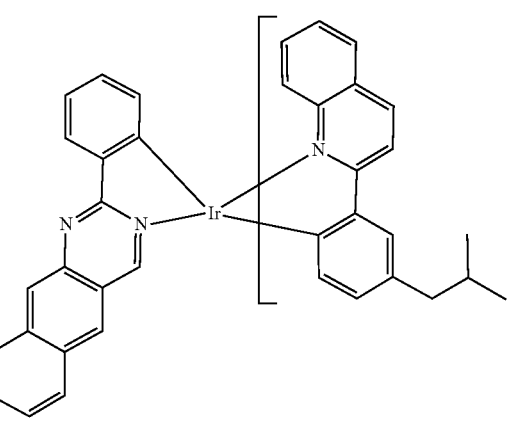
EX87
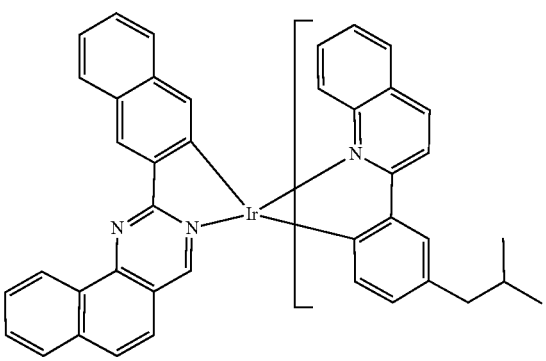

-continued
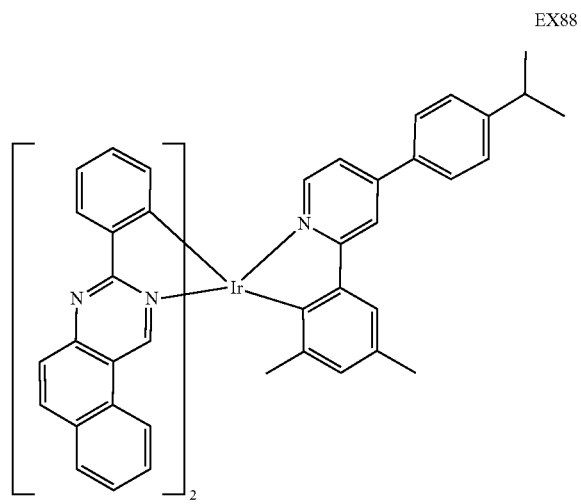
EX88
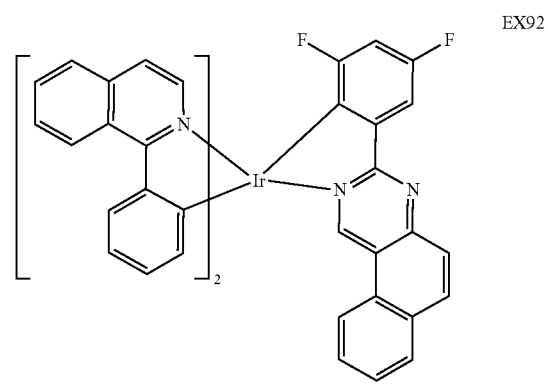
EX92
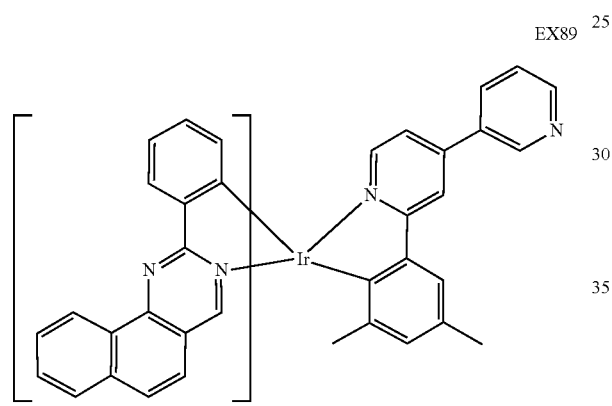
EX89
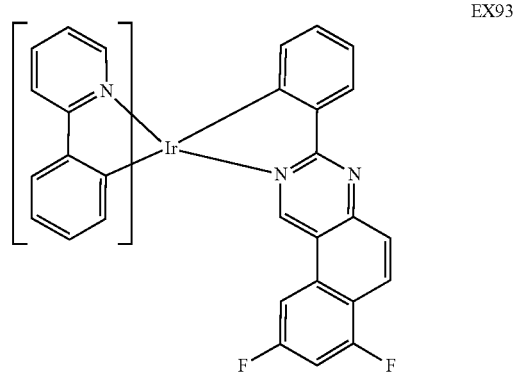
EX93
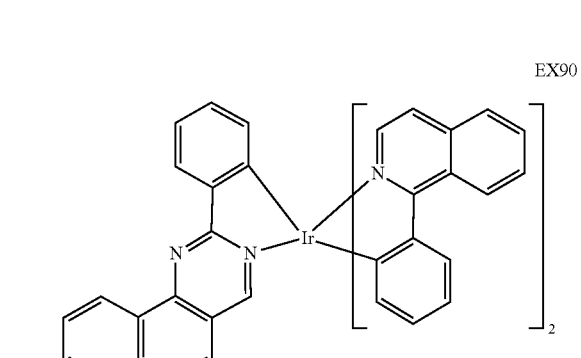
EX90
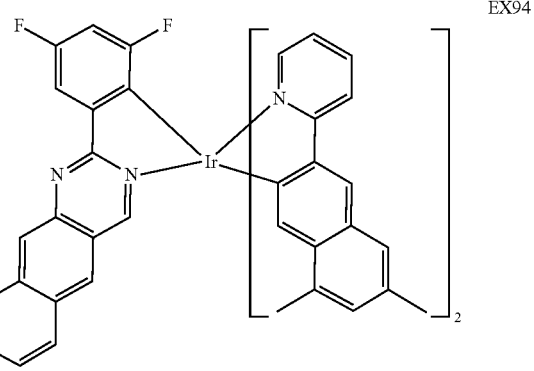
EX94
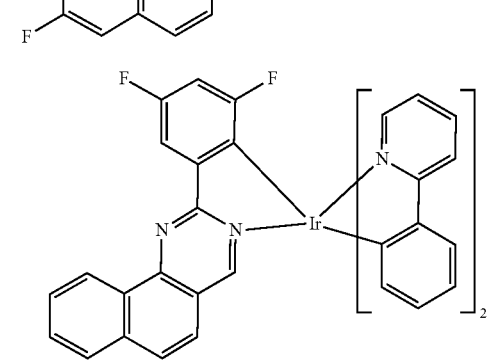
EX91
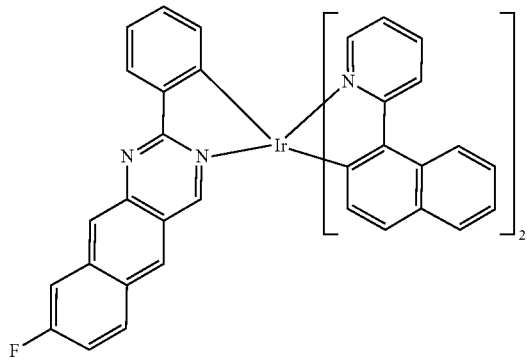
EX95

EX96
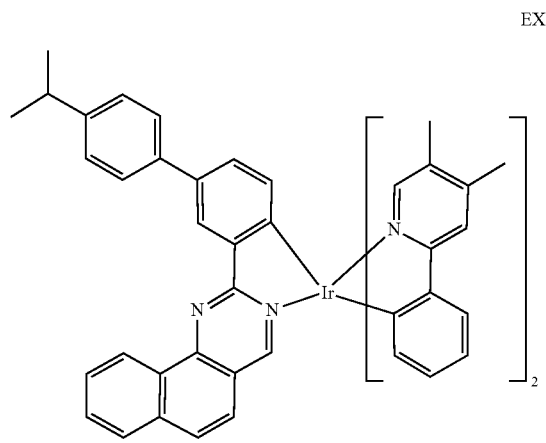
EX100
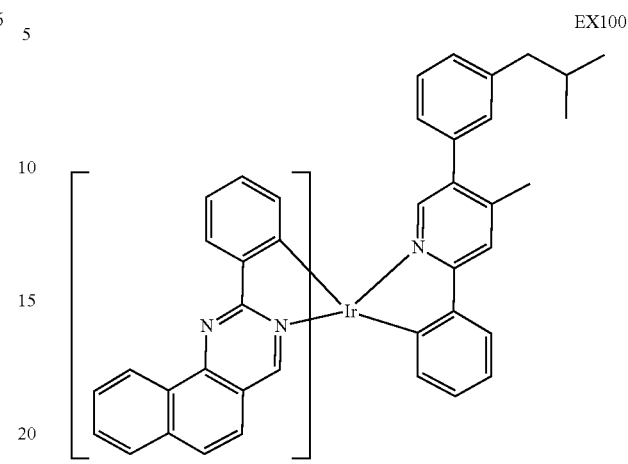
EX97
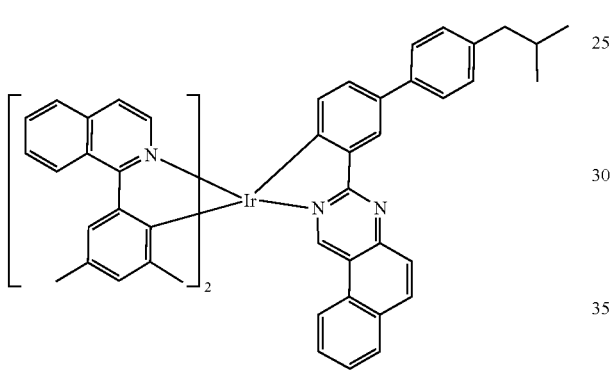
EX101
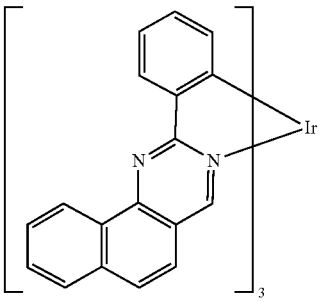
EX98
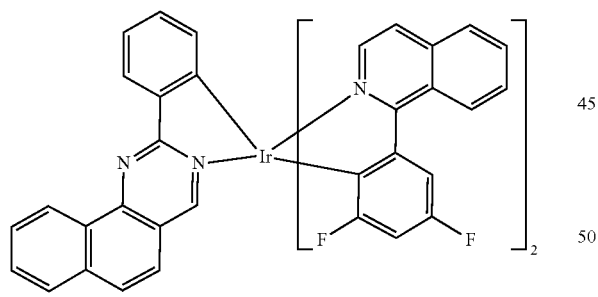
EX102
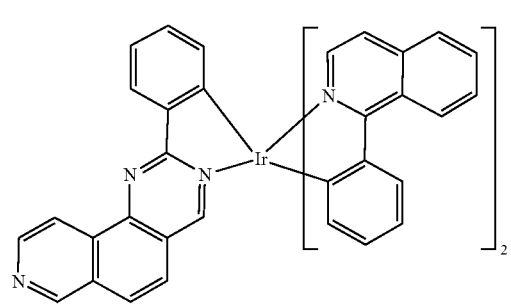
EX99
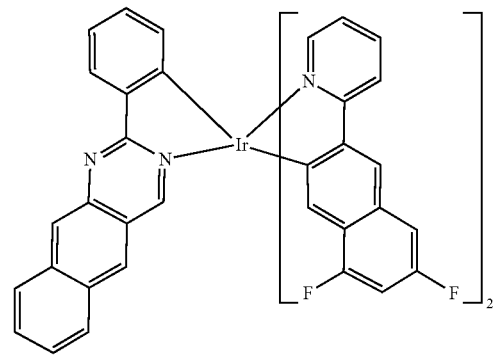
EX103

EX104 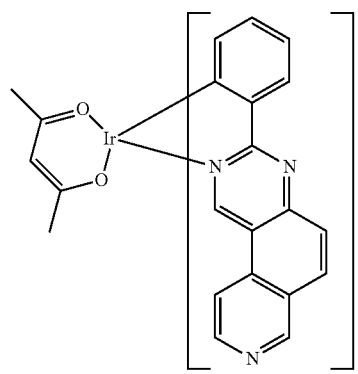
EX105 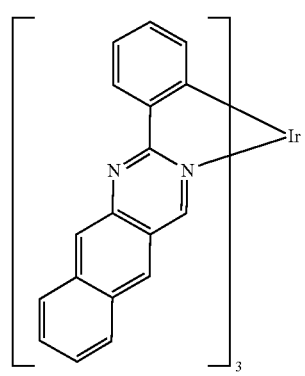
EX106 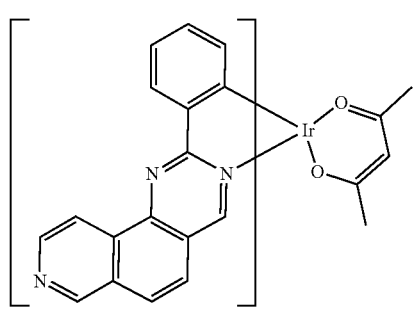
EX107 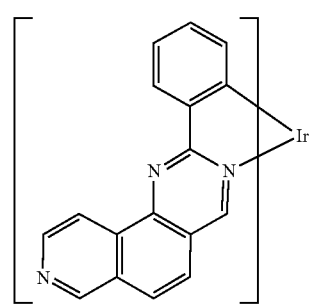
EX108 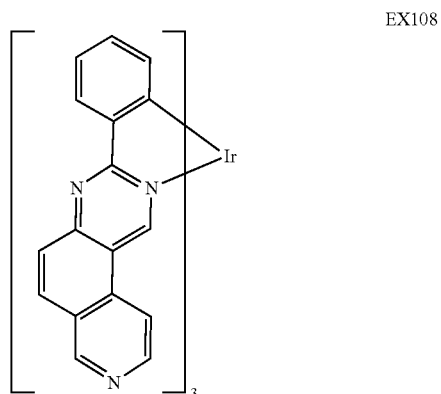
EX109 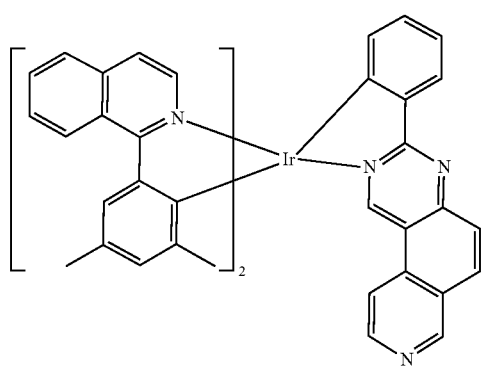
EX110 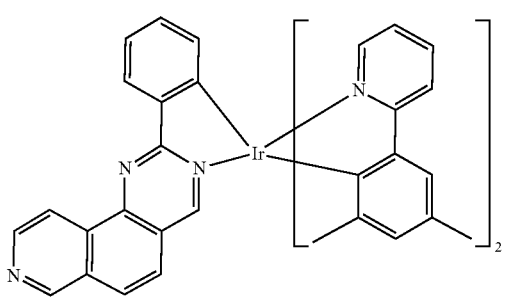
EX111 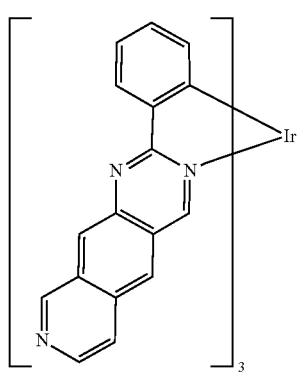

EX112
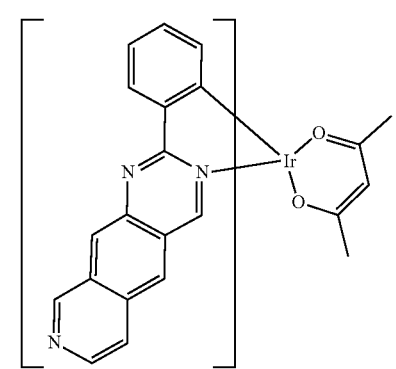
EX113
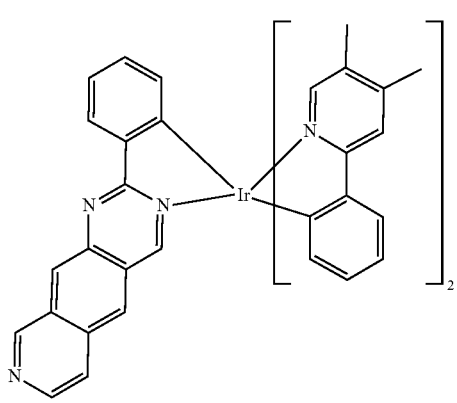
EX114
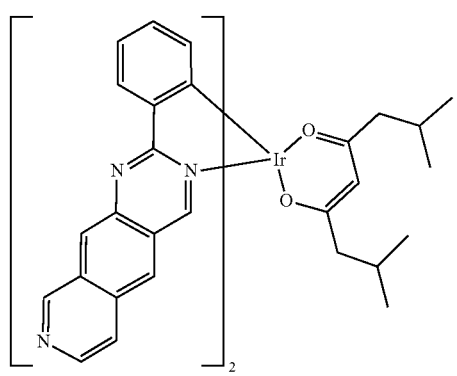
EX115
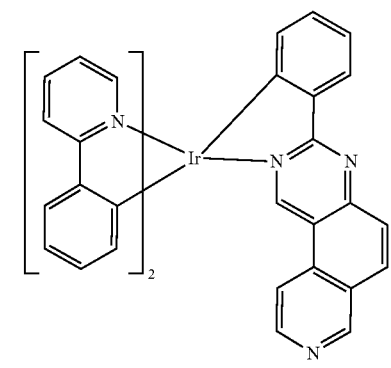
EX116
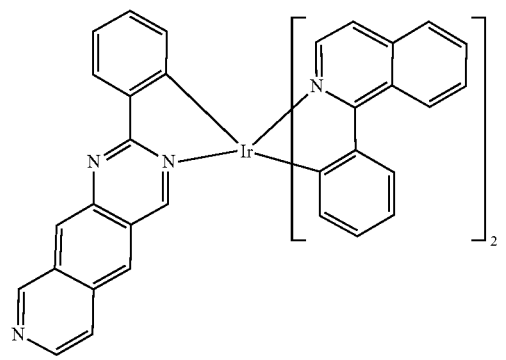
EX117
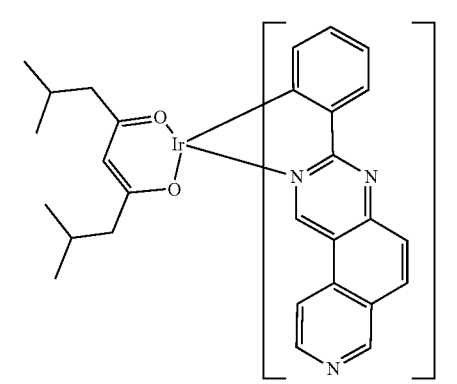
EX118
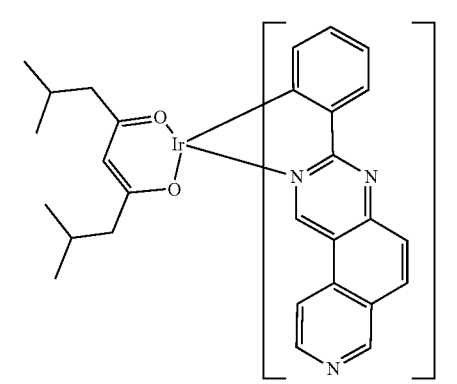
EX119
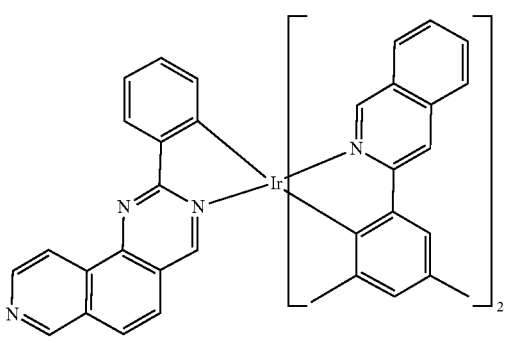

EX120
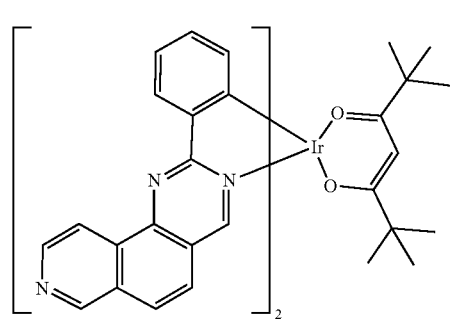
EX121
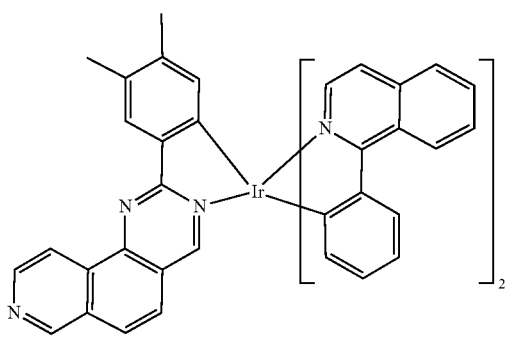
EX122
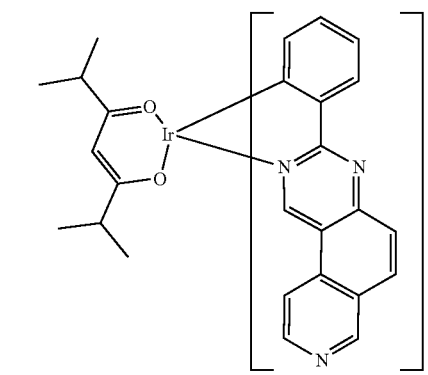
EX123
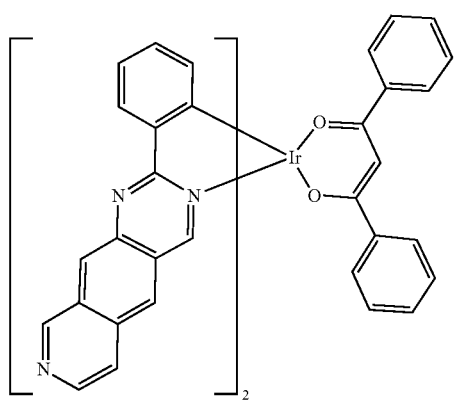
EX124
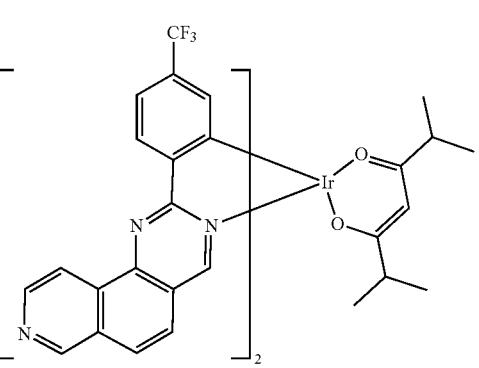
EX125
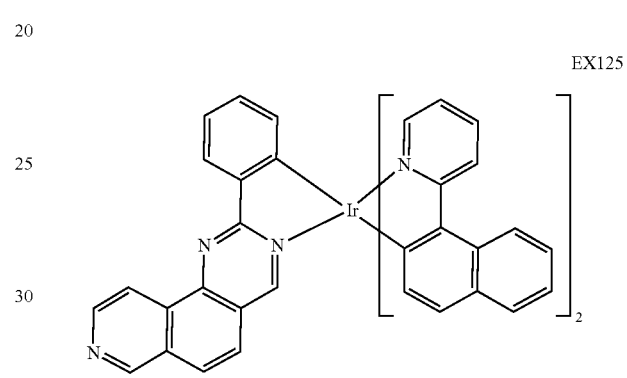
EX126
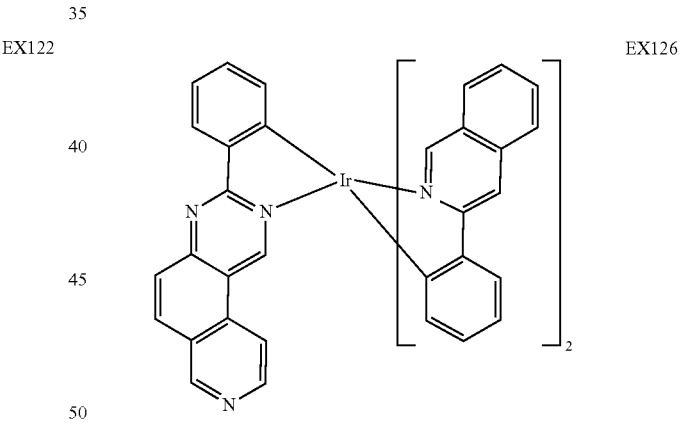
EX127
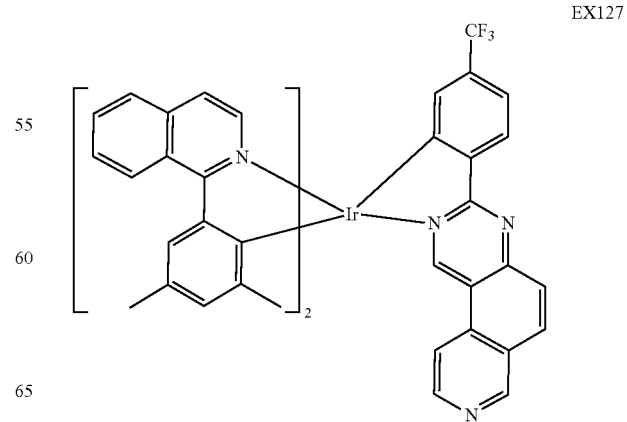

EX128
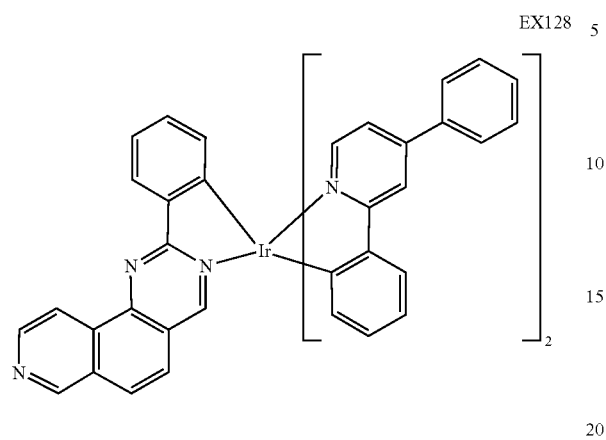
EX132
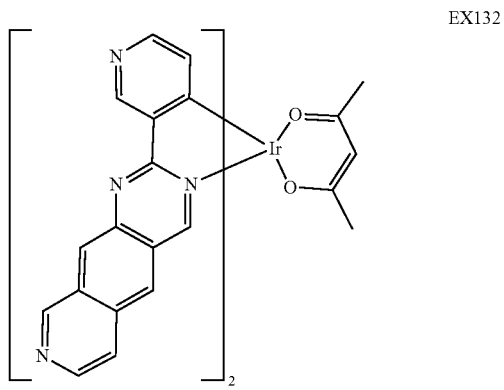
EX129
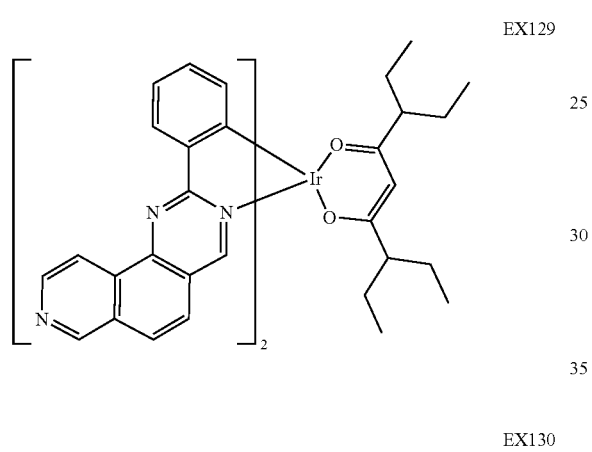
EX133
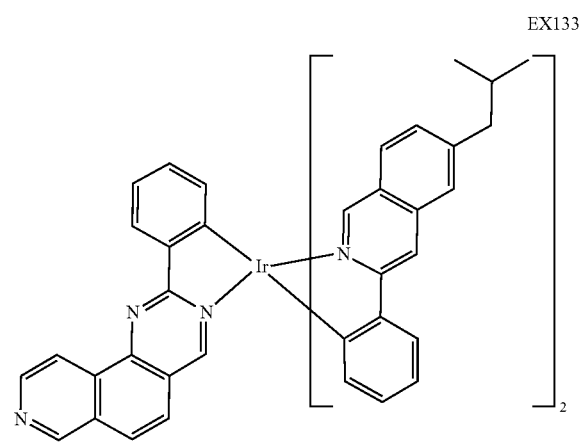
EX130
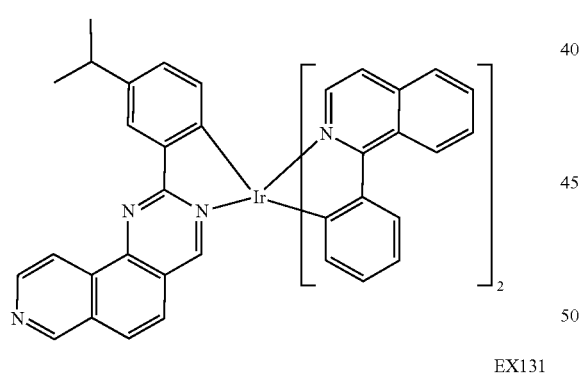
EX134
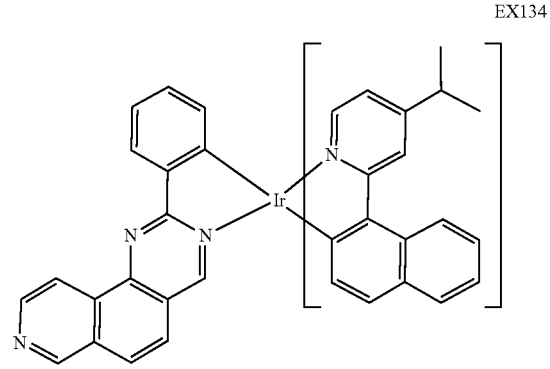
EX131
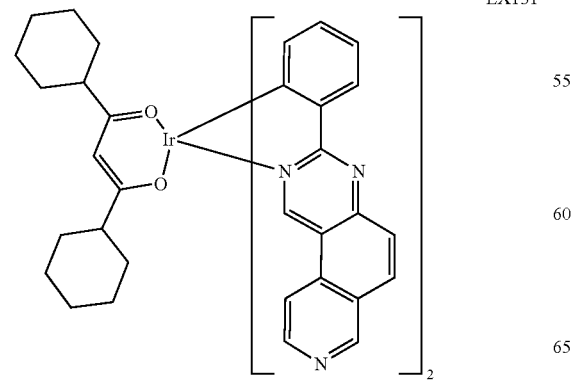
EX135
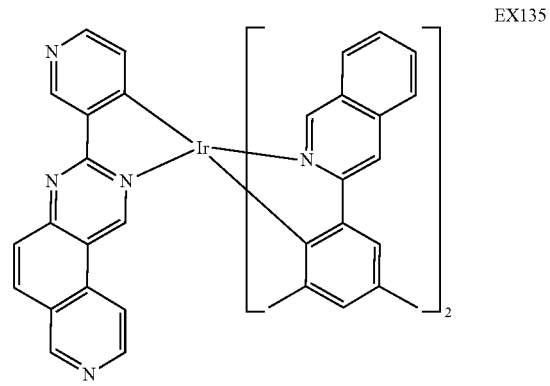

-continued

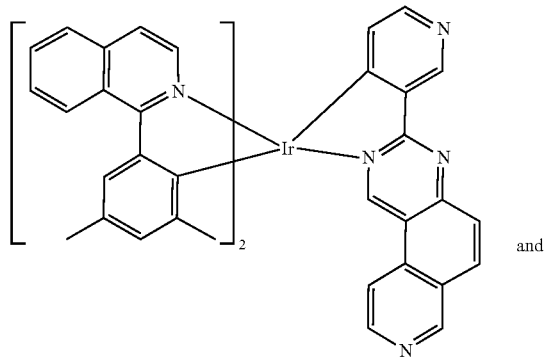

EX136 and

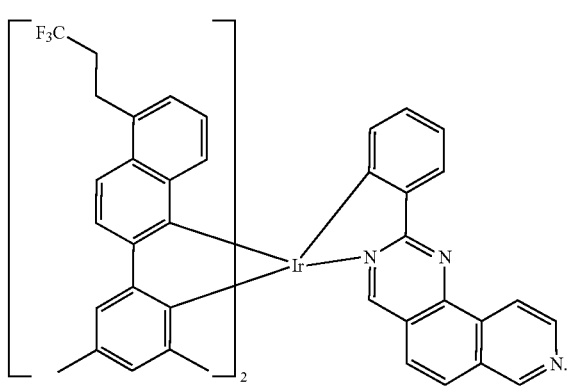

EX137

Referring to FIG. 1, the first organic EL device 510 may comprise an anode 310, a cathode 390 and one or more organic layers 320, 330, 340, 350E, 360, 370, 380 formed between the anode 310 and the cathode 390. From the bottom to the top, the one or more organic layers may comprise a hole injection layer 320, a hole transport layer 330, an electron blocking layer 340, an emissive layer 350E, a hole blocking layer 360, an electron transport layer 370 and an electron injection layer 380.

The emissive layer 350E may comprise a 15% the compound of formula (1) 350C and the co-host material (i.e. H2 and H3) doped with the compound of formula (1). The compound of formula (1) may be a green, yellow and red guest material for tuning the wavelength at which the emissive layer 350E emits light, so that the color of emitted light may be green, yellow and red. The compound of formula (1) may be a dopant 350C of the emissive layer 350E.

FIG. 2 is a cross-sectional view of an organic EL device without the compound of the present invention. Referring to FIG. 2, the organic EL device 400 may comprise an anode 310, a cathode 390 and one or more organic layers 320, 330, 340, 350, 360, 370, 380 formed between the anode 310 and the cathode 390. From the bottom to the top, the one or more organic layers may comprise a hole injection layer 320, a hole transport layer 330, an electron blocking layer 340, an emissive layer 350, a hole blocking layer 360, an electron transport layer 370 and an electron injection layer 380. The emissive layer 350 may comprise a 15% dopant D1 of Ir(2-phq)$_2$(acac), Ir(ppy)$_3$ or YD. The emissive layer 350 may further comprise an organic compound H2 and H3 doped with Ir(2-phq)$_2$(acac), Ir(ppy)$_3$ or YD. The dopant D1 may be a green guest material (Ir(ppy)$_3$), yellow guest material (YD) or a red guest material (Ir(piq)$_2$(acac)). The organic compound H2 and H3 is a co-host of the emissive layer 350.

To those organic EL devices of FIG. 1 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 1 and FIG. 2 may be summarized in Table 1 below. The half-life is defined as the time that the initial luminance of 1000 cd/m$^2$ has dropped to half.

TABLE 1

| Host | Dopant Material | Driving Voltage (V) | Current Efficiency (cd/A) | Color | Half-life (hours) |
|---|---|---|---|---|---|
| H2 + H3 | Ir(piq)$_2$(acac) | 4.9 | 16.1 | Red | 370 |
| H2 + H3 | EX1 | 3.8 | 22.7 | Red | 795 |
| H2 + H3 | EX2 | 3.7 | 24.0 | Red | 830 |
| H2 + H3 | EX4 | 3.8 | 22.5 | Red | 780 |
| H2 + H3 | EX9 | 3.8 | 22.8 | Red | 795 |
| H2 + H3 | EX10 | 3.9 | 21.9 | Red | 765 |
| H2 + H3 | EX11 | 3.7 | 23.4 | Red | 810 |
| H2 + H3 | EX13 | 3.9 | 21.5 | Red | 740 |
| H2 + H3 | EX14 | 4.0 | 21.1 | Red | 720 |
| H2 + H3 | EX27 | 3.5 | 25.8 | Red | 895 |
| H2 + H3 | EX35 | 3.6 | 25.4 | Red | 880 |
| H2 + H3 | EX36 | 3.6 | 24.8 | Red | 855 |
| H2 + H3 | EX44 | 4.1 | 20.0 | Red | 655 |
| H2 + H3 | EX55 | 4.3 | 19.1 | Red | 625 |
| H2 + H3 | EX56 | 4.4 | 18.5 | Red | 590 |
| H2 + H3 | EX71 | 4.5 | 16.9 | Red | 550 |
| H2 + H3 | EX75 | 4.0 | 20.7 | Red | 695 |
| H2 + H3 | EX92 | 4.5 | 17.4 | Red | 575 |
| H2 + H3 | EX98 | 4.4 | 17.9 | Red | 580 |
| H2 + H3 | EX103 | 3.8 | 22.0 | Red | 770 |
| H2 + H3 | EX106 | 4.1 | 20.3 | Red | 670 |
| H2 + H3 | EX117 | 4.2 | 19.8 | Red | 650 |
| H2 + H3 | EX119 | 3.8 | 22.3 | Red | 780 |
| H2 + H3 | Ir(ppy)$_3$ | 4.2 | 45.3 | Green | 700 |
| H2 + H3 | EX22 | 3.9 | 53.4 | Green | 910 |
| H2 + H3 | EX102 | 3.8 | 56.3 | Green | 980 |
| H2 + H3 | EX107 | 4.0 | 49.8 | Green | 870 |
| H2 + H3 | YD | 4.9 | 38.1 | Yellow | 340 |
| H2 + H3 | EX7 | 4.3 | 46.3 | Yellow | 470 |
| H2 + H3 | EX28 | 4.4 | 44.8 | Yellow | 445 |
| H2 + H3 | EX33 | 4.6 | 42.1 | Yellow | 380 |
| H2 + H3 | EX47 | 4.4 | 45.4 | Yellow | 455 |
| H2 + H3 | EX58 | 4.6 | 43.2 | Yellow | 405 |
| H2 + H3 | EX91 | 4.5 | 43.7 | Yellow | 430 |

According to Table 1, in the first organic EL device 510, the compound of formula (1) comprised as a dopant 350C of FIG. 1 exhibits performance better than a prior art organic EL material Ir(piq)$_2$(acac).

A method of producing the first organic EL device 510 of FIG. 1 and the organic EL device 400 of FIG. 2 is described. ITO-coated glasses with 9~12 ohm/square in resistance and 120~160 nm in thickness are provided (hereinafter ITO substrate) and cleaned in a number of cleaning steps in an ultrasonic bath (e.g., detergent, deionized water).

Before vapor deposition of the organic layers, cleaned ITO substrates may be further treated by UV and ozone. All pre-treatment processes for ITO substrate are under clean room (class 100), so that an anode 310 may be formed.

One or more organic layers 320, 330, 340, 350 (FIG. 2), 350E (FIG. 1), 360, 370, 380 are applied onto the anode 310 in order by vapor deposition in a high-vacuum unit (10$^{-7}$ Torr), such as resistively heated quartz boats. The thickness of the respective layer and the vapor deposition rate (0.1~0.3 nm/sec) are precisely monitored or set with the aid of a quartz-crystal monitor. It is also possible, as described above, each of the organic layers may comprise more than one organic compound. For example, an emissive layer 350E or 350 may be formed of a dopant and a host doped with the dopant. An emissive layer 350E or 350 may also be formed of a co-host and a host co-deposited with the co-host. This may be successfully achieved by co-vaporization from two or more sources. Accordingly, the compounds for the organic layers of the present invention are thermally stable.

Referring to FIG. 1 and FIG. 2, onto the anode 310, Dipyrazino[2,3-f:2,3-]quinoxaline-2,3,6,7,10,11-hexacarbonitrile (HAT-CN) may be applied to form a hole injection layer (HIL) 320 having a thickness of about 20 nm in the organic EL device 510 or 400. N,N-Bis(naphthalene-1-yl)-N,N-bis(phenyl)-benzidine (NPB) may be applied to form a hole transporting layer (HTL) 330 having a thickness of about 110 nm, N-(biphenyl-4-yl)-9,9-dimethyl-N-(4'-phenyl-biphenyl-4-yl)-9H-fluoren-2-amine (EB2) may be applied to form an electron blocking layer (EBL) 340 having a thickness of about 5 nm.

Referring to FIG. 1 and FIG. 2, in the organic EL device 510 (FIG. 1) or 400 (FIG. 2), an emissive layer (EML) 350E or 350 may be formed to have a thickness of about 30 nm.

Referring to FIG. 2, in the organic EL device 400, the iridium complex (i.e., Ir(piq)$_2$(acac) of paragraph [0002]) may be applied to form a dopant of an emissive layer 350 of FIG. 2. The emissive layer 350 may further comprise H2 and H3 as a host, also a green, yellow and red guest of the emissive layer 350.

On the emissive layer 350 having a thickness of about 30 nm, a compound HB3 may be a hole blocking material (HBM) to form a hole blocking layer (HBL) 360 having a thickness of about 10 nm. 2-(10,10-dimethyl-10H-indeno[2,1-b]triphenylen-12-yl)-4,6-diphenyl-1,3,5-triazine (ET2) may be applied as an electron transporting material to co-deposit with 8-hydroxyquinolato-lithium (LiQ) at a ratio of 6:4, thereby forming an electron transporting layer 370 of the organic EL device 510 or 400. The electron transporting layer (ETL) 370 may have a thickness of about 35 nm. Table 2 shows the layer thickness and materials of the organic EL device 510 (FIG. 1) or 400 (FIG. 2).

TABLE 2

| Layer | Material | Thickness (nm) |
|---|---|---|
| Cathode | Al | 160 |
| EIL | LiQ | 1 |
| ETL | LiQ (40%):ET2 (60%) | 35 |
| HBL | HB3 | 10 |
| EML | H2 and H3 (85%):350C (15%) | 30 |
| EBL | EB2 | 5 |
| HTL | NPB | 110 |
| HIL | HAT-CN | 20 |
| Anode | ITO substrate | 120-160 |

The organic compounds ET2, HB3, H2, H3, Ir(2-phq)$_2$(acac), Ir(ppy)$_3$, YD, EB2, NPB and HAT-CN for producing the organic EL device 400 or 510 in this invention may have the formulas as follows:

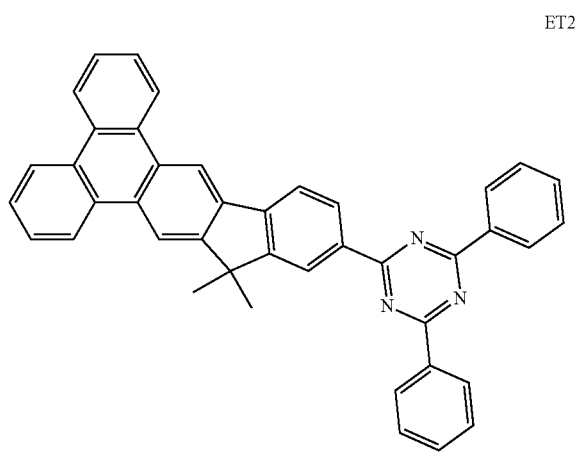

ET2

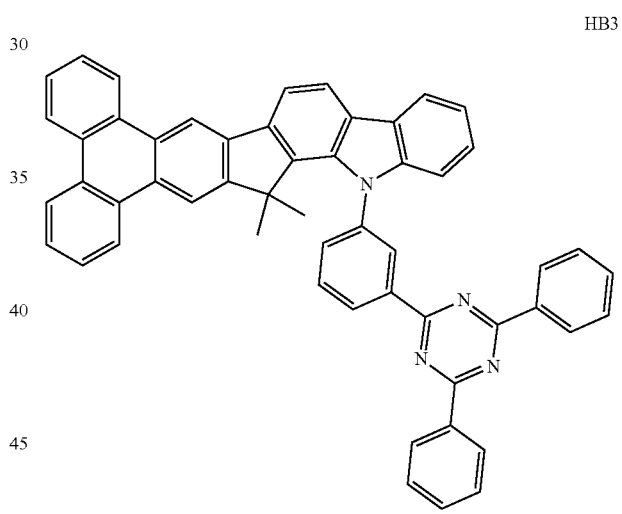

HB3

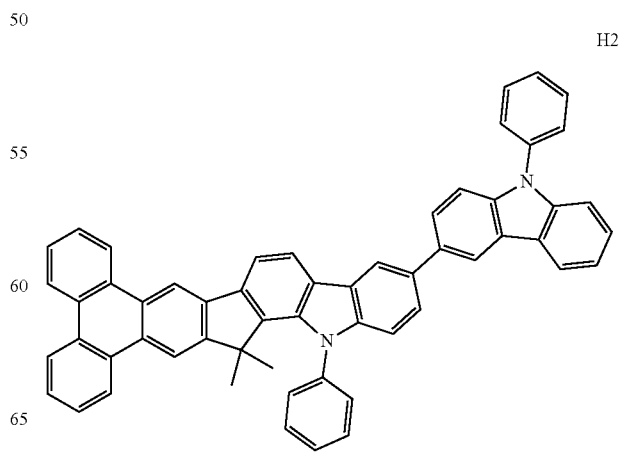

H2

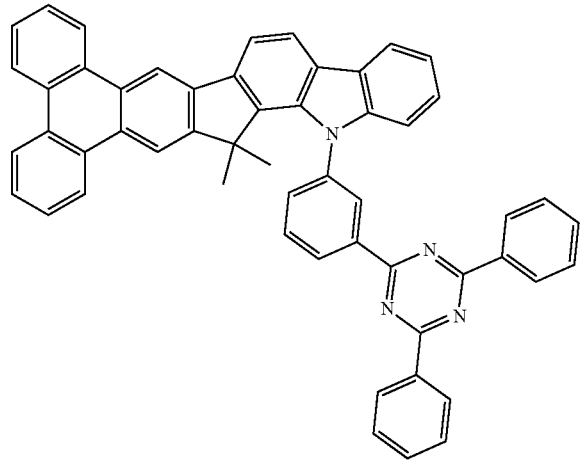

H3

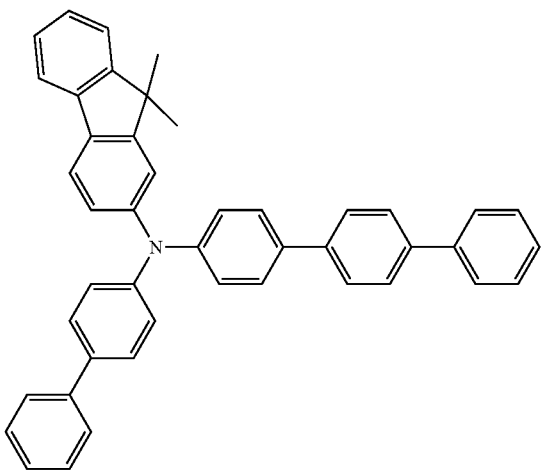

EB2

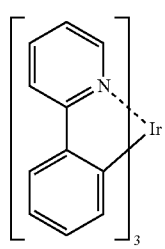

Ir(piq)2(acac)

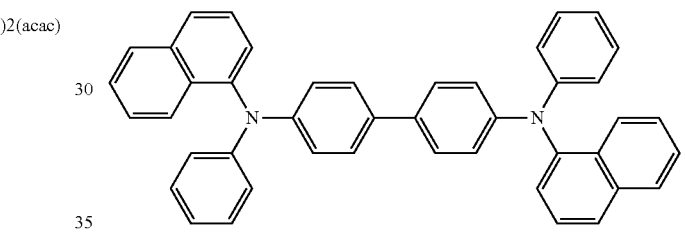

NPB

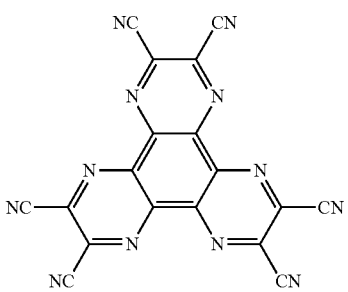

Ir(ppy)3

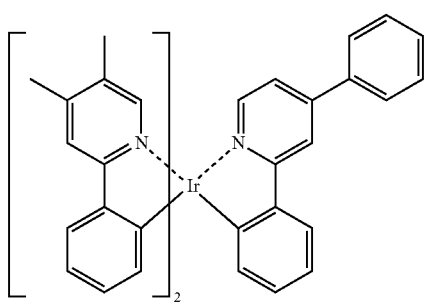

YD

HAT-CN

Referring to FIG. 1 and FIG. 2, the organic EL device 510 or 400 may further comprise a low work function metal, such as Al, Mg, Ca, Li or K, as a cathode 390 by thermal evaporation. The cathode 390 having a thickness of about 160 nm may help electrons injecting the electron transporting layer 370 from cathode 390. Between the cathode 390 (e.g., Al in Table 2) and the electron transporting layer 370, a thin electron injecting layer (EIL) 380 of LiQ is introduced. The electron injecting layer (EIL) 380 has a thickness of about 1 nm is to reduce the electron injection barrier and to improve the performance of the organic EL device 510 or 400. The material of the electron injecting layer 380 may alternatively be metal halide or metal oxide with low work function, such as LiF, MgO, or $Li_2O$.

Detailed preparation of the organic compounds of the present invention will be clarified by exemplary embodiments below, but the present invention is not limited thereto. EXAMPLES 1 to 29 show the preparation of the organic compounds of the present invention.

Example 1

Synthesis of EX1

Synthesis of Intermediate 1a

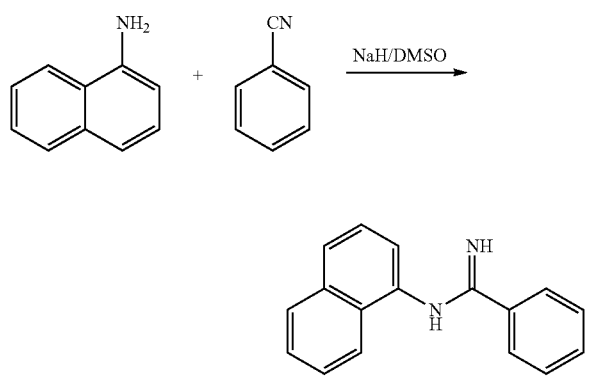

A mixture of Sodium hydride (7.2 g, 300 mmol), 1-Naphthylamine (31.5 g, 220 mmol), Benzonitrile (22.7 g, 220 mmol), 100 ml of DMSO was stirred at −10° C. The reaction mixture was stirred at 0° C. for 1 hours, and then warmed to room temperature for 3 hours. The reaction was finished, and then diluted with 1000 mL of water. The crude precipitate was purified by column chromatography on silica to afford Intermediate 1a (39.6 g, 73%) as a white solid.

Synthesis of Intermediate 1b to 1j

Synthesis of Intermediate 1b to 1j was prepared according to the synthesis method of Intermediate 1a.

Synthesis of Intermediate 2a

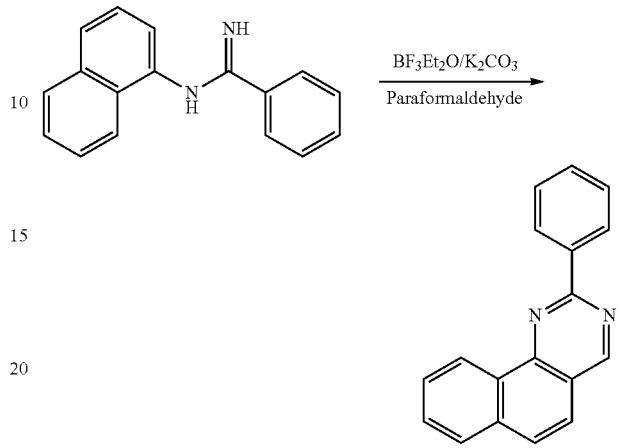

A mixture of Intermediate 1a (39.6 g, 160.6 mmol), Boron trifluoride diethyl etherate (1.2 g, 8.0 mmol), Potassium carbonate (22.2 g, 160.6 mmol), Paraformaldehyde (14.4 g, 481.8 mmol), 640 ml of DMSO. The mixture was sealed under $O_2$ and stirred at 140° C. for 24 hrs. After the reaction finished, the mixture was allowed to cool to room temperature. The solution was extracted with dichloromethane and water. The organic layer was dried with anhydrous magnesium sulfate and then the solvent was evaporated under reduced pressure. The residue was purified by column chromatography on silica to afford Intermediate 2a (36.6 g, 89%) as a light yellow solid.

Synthesis of Intermediate 2b to 2j

Synthesis of Intermediate 2b to 2j were according to the synthesis method of Intermediate 2a.

| Reactant structure | Product structure | Weight Yield |
|---|---|---|
| 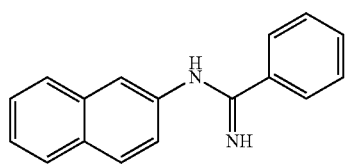 [SMILES: N=C(Nc1ccc2ccccc2c1)c1ccccc1]<br>1b (39.6 g, 160.6 mmol) | 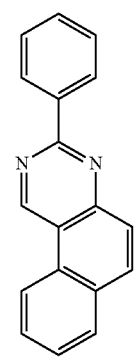<br>2b | 35.8 g<br>87% |

-continued

| Reactant structure | Product structure | Weight Yield |
|---|---|---|
| 1c (50.5 g, 160.6 mmol) | 2c | 43.2 g 83% |
| 1d (61.4 g, 160.6 mmol) | 2d | 51.0 g 81% |
| 1e (61.4 g, 160.6 mmol) | 2e | 51.0 g 81% |

-continued

| Reactant structure | Product structure | Weight Yield |
|---|---|---|
| 1f (66.1 g, 160.6 mmol) | 2f | 50.8 g 75% |
| 1g (45.3 g, 160.6 mmol) | 2g | 40.4 g 86% |
| 1h (45.3 g, 160.6 mmol) | 2h | 39.9 g 85% |
| 1i (39.7 g, 160.6 mmol) | 2i | 33.5 g 81% |

-continued

| Reactant structure | Product structure | Weight Yield |
|---|---|---|
| 1j (39.7 g, 160.6 mmol) | 2j | 33.9 g 82% |

Synthesis of Intermediate 3a

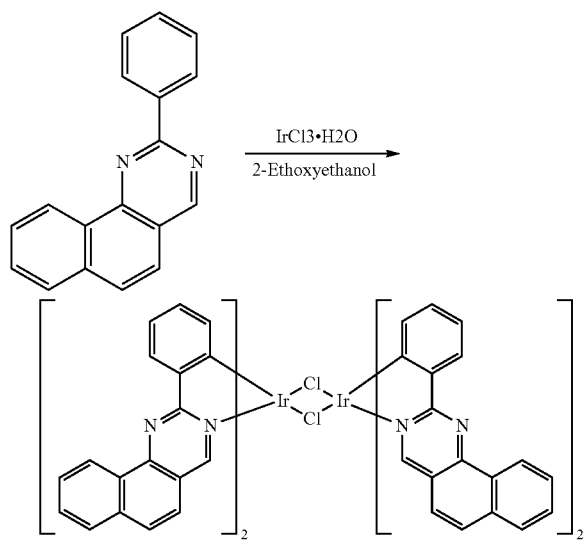

A mixture of 7.3 g (28.4 mmol) of Intermediate 2a, 4.7 g (12.9 mmol) of Iridium(III) chloride hydrate, 75 ml of 2-Ethoxyethanol and 25 ml of water was degassed and placed under nitrogen, and then heated at 120° C. overnight. After the reaction finished, the mixture was allowed to cool to room temperature. The precipitated product was filtered off with suction and washed with water. Afterwards, 250 ml of water was added and stirred for 1 hr, and then the precipitated product was filtered off with suction. Subsequently, 100 ml of EtOH was added and stirred for 1 hr, and then the precipitated product was filtered off with suction, yielding 5.4 g of Intermediate 3a as brown solid (56%).

Synthesis of Intermediate 3b to 3k

Synthesis of Intermediate 3b to 3k were according to the synthesis method of Intermediate 3a.

| Reactant structure | Product structure | Weight Yield |
|---|---|---|
| 2b (7.3 g, 28.4 mmol) | 3b | 5.1 g 54% |

-continued
| Reactant structure | Product structure | Weight Yield |
|---|---|---|
| 2e (11.1 g, 28.4 mmol) | 3e | 6.4 g 49% |
| 2i (7.3 g, 28.4 mmol) | 3i | 5.3 g 51% |
| 2k (7.3 g, 28.4 mmol) | 3k | 5.9 g 47% |
Synthesis of EX1
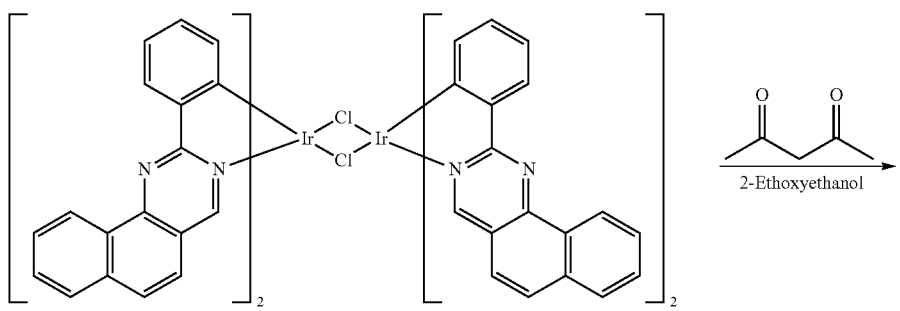

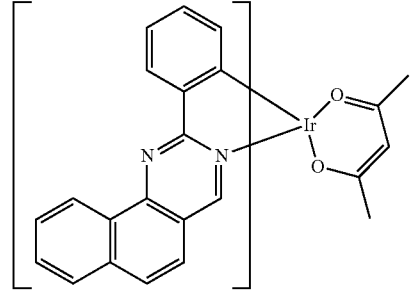

A mixture of 4.0 g (2.7 mmol) of Intermediate A, 2.8 g (27.6 mmol) of Acetylacetone, 2.9 g (27.6 mmol) of Sodium carbonate, and 28 ml of 2-Ethoxy-ethanol was degassed and placed under nitrogen, and then heated at 120° C. overnight. After the reaction finished, the mixture was allowed to cool to room temperature. The precipitated product was filtered off with suction and washed with water. Afterwards, 150 ml of water was added and stirred for 1 hr, and then the precipitated product was filtered off with suction. Subsequently, 80 ml of EtOH was added and stirred for 1 hr, and then the precipitated product was filtered off with suction, yielding 2.2 g of EX1 as red solid (51%).
MS (m/z, EI$^+$): 800.9

Example 2 to 10

Synthesis of Compound EX4, EX9, EX10, EX13, EX14, EX44, EX56, EX106 and EX117.

Synthesis of Compound EX4, EX9, EX10, EX13, EX14, EX44, EX56, EX106 and EX117 were prepared according to the synthesis method of Compound EX1.

-continued

| Reactant structure | | Product structure | Weight Yield |
|---|---|---|---|
| 3a (4.0 g, 2.7 mmol) | (5.9 g, 27.6 mmol) | EX13 MS (m/z, EI⁺): 913.1 | 2.3 g 47% |
| 3b (4.0 g, 2.7 mmol) | (4.3 g, 27.6 mmol) | EX14 MS (m/z, EI⁺): 857.0 | 2.6 g 56% |
| 3k (4.8 g, 2.7 mmol) | (2.8 g, 27.6 mmol) | EX44 MS (m/z, EI⁺): 954.1 | 2.61 g 41% |
| 3e (5.4 g, 2.7 mmol) | (5.1 g, 27.6 mmol) | EX56 MS (m/z, EI⁺): 1157.0 | 2.6 g 42% |
| 3i (4.0 g, 2.7 mmol) | (2.8 g, 27.6 mmol) | EX106 MS (m/z, EI⁺): 802.9 | 2.2 g 50% |

| Reactant structure | Product structure | Weight Yield |
|---|---|---|
| 3i (4.0 g, 2.7 mmol) | (5.1 g, 27.6 mmol) → EX117 MS (m/z, EI⁺): 887.0 | 2.5 g 52% |

Example 11

Synthesis of EX2

Synthesis of Intermediate 4a

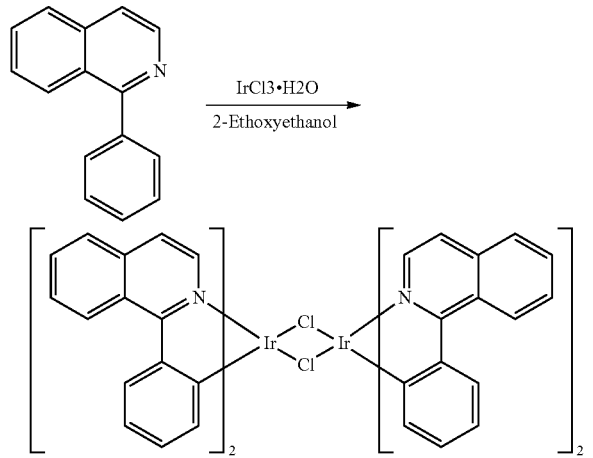

A mixture of 15.0 g (73.0 mmol) of 1-phenylisoquinoline, 12.0 g (33.2 mmol) of Iridium(III) chloride hydrate, 240 ml of 2-Ethoxyethanol and 60 ml of water was degassed and placed under nitrogen, and then heated at 120° C. overnight. After the reaction finished, the mixture was allowed to cool to room temperature. The precipitated product was filtered off with suction and washed with water. Afterwards, 750 ml of water was added and stirred for 1 hr, and then the precipitated product was filtered off with suction. Subsequently, 300 ml of EtOH was added and stirred for 1 hr, and then the precipitated product was filtered off with suction, yielding 12.8 g of Intermediate 4a as brown solid (55%).

Synthesis of Intermediate 4b to 4i

Synthesis of Intermediate 4b to 4i were according to the synthesis method of Intermediate 4a.

| Reactant structure | Product structure | Weight Yield |
|---|---|---|
| (17 g, 73 mmol) | 4b | 14.9 g 59% |
| (13.4 g, 73 mmol) | 4c | 13.6 g 63% |

-continued
| Reactant structure | Product structure | Weight Yield |
|---|---|---|
| 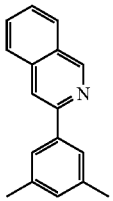  (17 g, 73 mmol) | 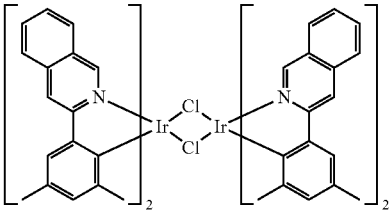  4d | 14.7 g 58% |
| 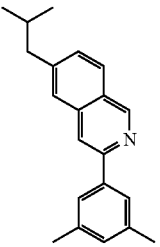 [SMILES: Cc1cc(C)cc(-c2cc3cc(CC(C)C)ccc3cn2)c1]  (21.1 g, 73 mmol) | 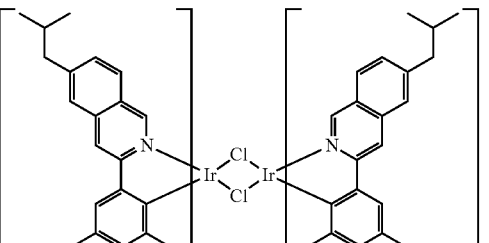  4e | 14.7 g 50% |
| 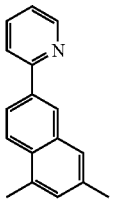  (17 g, 73 mmol) | 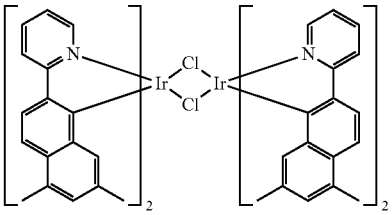  4f | 13.4 g 53% |
| 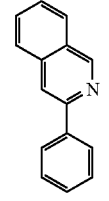  (15 g, 73 mmol) | 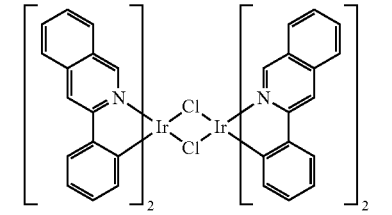  4g | 11.8 g 51% |
| 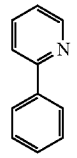  (11.3 g, 73 mmol) | 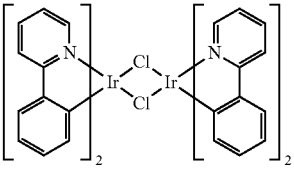  4h | 11.9 g 61% |
|   (17.6 g, 73 mmol) | 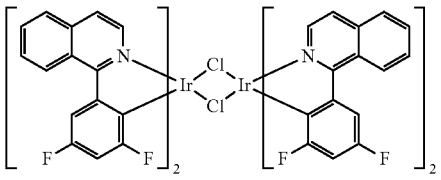  4i | 11.9 g 46% |

Synthesis of Intermediate 5a

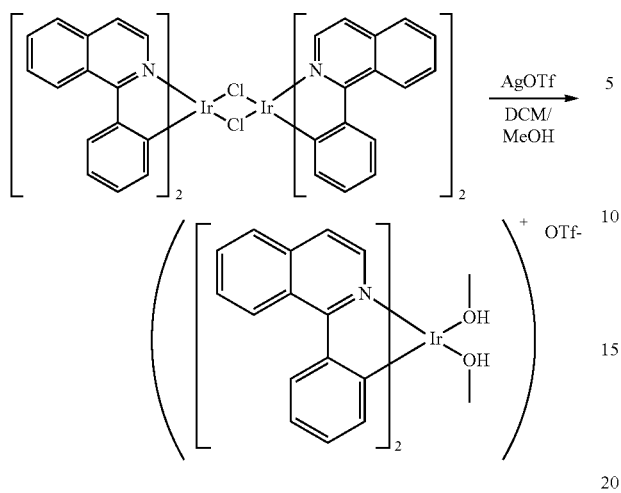

A mixture of 11.6 g (9.1 mmol) of Intermediate 4a, 5.3 g (20.9 mmol) of silver triflate, 460 ml of dichloromethane and 25 ml of methanol was placed under nitrogen, and then stirred overnight. After the reaction finished, the silver chloride was filtered off and the solvent was evaporated to obtain 14.5 g of iridium triflate precursor, which was used directly in the next step without purification.

Synthesis of Intermediate 5b to 5i

Synthesis of Intermediate 5b to 5i were according to the synthesis method of Intermediate 5a.

| Reactant structure | Product structure | Weight Yield |
|---|---|---|
| 4b (14.9 g, 10.7 mmol) | 5b | 13.8 g |
| 4C (13.6 g, 11.5 mmol) | 5c | 13.5 g |
| 4d (14.7 g, 10.6 mmol) | 5d | 14.4 g |

-continued

| Reactant structure | Product structure | Weight Yield |
|---|---|---|
| 4e (14.7 g, 9.1 mmol) | 5e | 13.7 g |
| 4f (13.4 g, 9.7 mmol) | 5f | 13.9 g |
| 4g (11.8 g, 9.3 mmol) | 5g | 14.7 g |
| 4h (11.9 g, 11.1 mmol) | 5h | 14.9 g |
| 4i (11.9 g, 8.4 mmol) | 5i | 13.5 g |

Synthesis of EX2

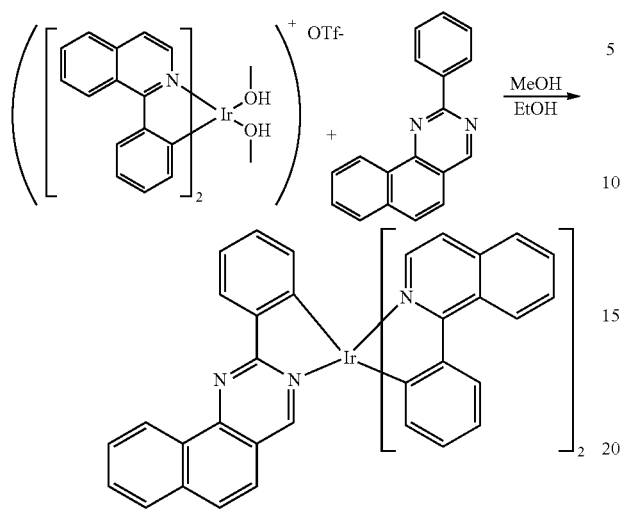

A mixture of 4.0 g (4.9 mmol) of Intermediate 5a, 3.8 g (14.7 mmol) of Intermediate 2a, 90 ml of EtOH and 90ml of MeOH was placed under nitrogen, and then heated to reflux overnight. After the reaction finished, the mixture was allowed to cool to room temperature. The orange-red precipitate formed was filtered under vacuum, washed with ethanol and hexane, and then purified by vacuum sublimation to give 2.0 g (49%) of orange-red product EX15. MS (m/z , EI+):856.0

EXAMPLE 12 to 26

Synthesis of Compound EX7, EX11, EX27, EX35, EX36, EX41, EX43, EX55, EX71, EX75, EX91, EX92, EX98, EX103 and EX119.

Synthesis of Compound EX7, EX11, EX27, EX35, EX36, EX41, EX43, EX55, EX71, EX75, EX91, EX92, EX98, EX103 and EX119 were prepared according to the synthesis method of Compound EX2.

| Reactant structure | | Product structure | Weight Yield |
|---|---|---|---|
| 5c (3.8 g, 4.9 mmol) | 2a (3.8 g, 14.7 mmol) | EX7 MS (m/z, EI+): 811.0 | 2 g 50% |
| 5b (4.1 g, 4.9 mmol) | 2b (3.8 g, 14.7 mmol) | EX11 MS (m/z, EI+): 911.1 | 2.1 g 47% |
| 5d (4.1 g, 4.9 mmol) | 2a (3.8 g, 14.7 mmol) | EX27 MS (m/z, EI+): 911.2 | 2.4 g 53% |

-continued

| Reactant structure | Product structure | Weight Yield |
|---|---|---|
| 5e (4.8 g, 4.9 mmol); 2a (3.8 g, 14.7 mmol) | EX35  MS (m/z, EI+): 1024.3 | 2.2 g  43% |
| 5e (4.8 g, 4.9 mmol); 2b (3.8 g, 14.7 mmol) | EX36  MS (m/z, EI+): 1024.3 | 2.3 g  45% |
| 5f (4.1 g, 4.9 mmol); 2c (4.8 g, 14.7 mmol) | EX41  MS (m/z, EI+): 979.1 | 2.3 g  47% |
| 5d (4.1 g, 4.9 mmol); 2j (4.9 g, 14.7 mmol) | EX43  MS (m/z, EI+): 987.2 | 2.0 g  41% |

-continued

| Reactant structure | Product structure | Weight Yield |
|---|---|---|
| 5g (4.0 g, 4.9 mmol) | 2d (5.8 g, 14.7 mmol) / EX55 MS (m/z, EI+): 991.0 | 1.8 g 37% |
| 5b (4.1 g, 4.9 mmol) | 2f (6.2 g, 14.7 mmol) / EX71 MS (m/z, EI+): 1076.3 | 1.7 g 32% |
| 5d (4.1 g, 4.9 mmol) | 2j (3.8 g, 14.7 mmol) / EX75 MS (m/z, EI+): 912.1 | 2.0 g 44% |
| 5h (3.5 g, 4.9 mmol) | 2g (4.3 g, 14.7 mmol) / EX91 MS (m/z, EI+): 790.8 | 1.7 g 45% |

-continued

| Reactant structure | | Product structure | Weight Yield |
|---|---|---|---|
| 5a (4.0 g, 4.9 mmol) | 2h (4.3 g, 14.7 mmol) | EX92 MS (m/z, EI+): 891.0 | 1.8 g 41% |
| 5i (4.3 g, 4.9 mmol) | 2a (3.8 g, 14.7 mmol) | EX98 MS (m/z, EI+): 926.9 | 2.1 g 47% |
| 5a (4.0 g, 4.9 mmol) | 2i (3.8 g, 14.7 mmol) | EX103 MS (m/z, EI+): 856.0 | 2.0 g 49% |
| 5d (4.1 g, 4.9 mmol) | 2i (3.8 g, 14.7 mmol) | EX119 MS (m/z, EI+): 912.1 | 2.4 g 53% |

Example 27

Synthesis of EX22
Synthesis of EX22

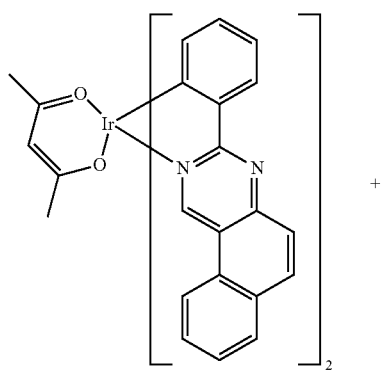

+

A mixture of 3.7 g (4.6 mmol) of EX4, 3.5 g (13.8 mmol) of Intermediate 2b, and 250 ml of glycerol was degassed and placed under nitrogen, and then heated at 200° C. overnight. After the reaction finished, the mixture was allowed to cool to room temperature. After the reaction finished, the mixture was allowed to cool to room temperature. Afterwards, 1000 ml of water was added and stirred for 1 hr, and then the precipitated product was filtered off with suction. The crude solid was purified by column chromatography on silica, yielding 2.4 g of EX22 as yellow solid (55%). MS (m/z, EI+): 957.1

Example 28 to 29

Synthesis of Compound EX102 and EX107.

Synthesis of Compound EX102 and EX107 were prepared according to the synthesis method of Compound EX22.

-continued

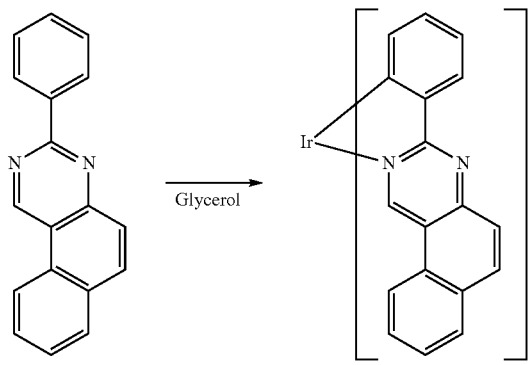

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound comprising a first ligand of the following formula:

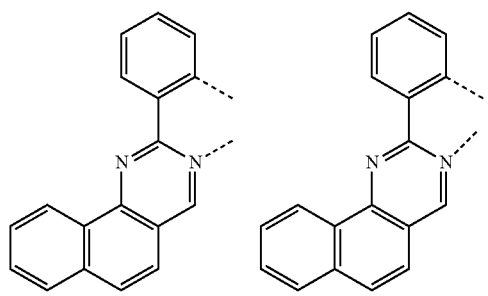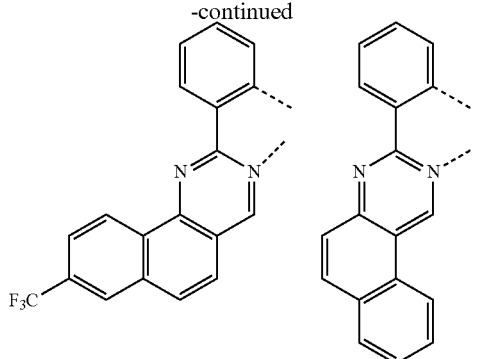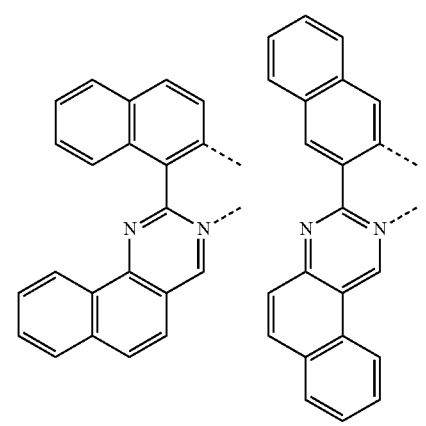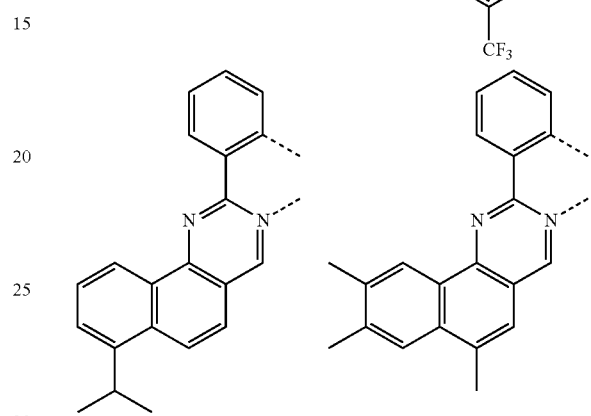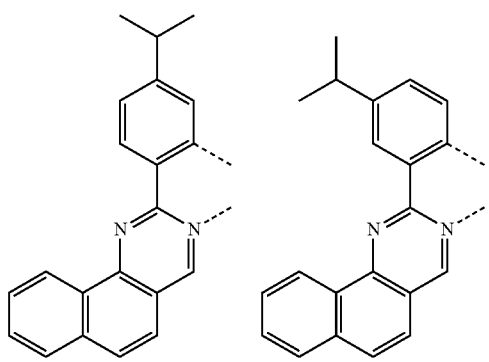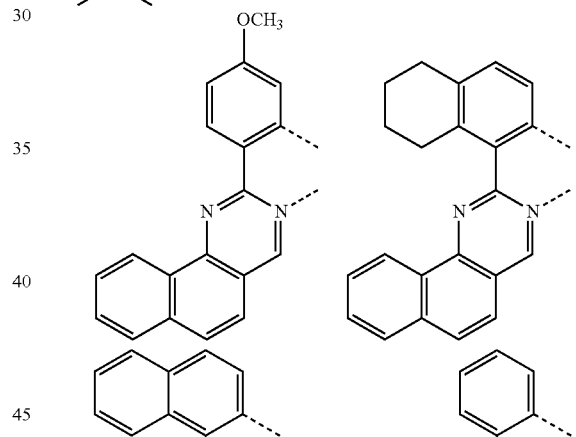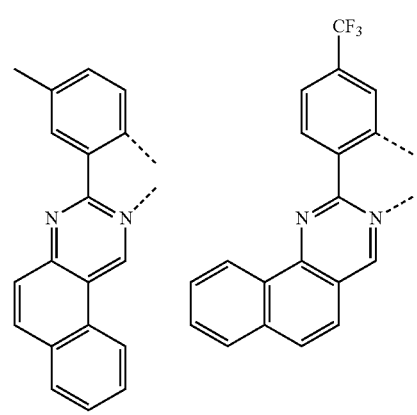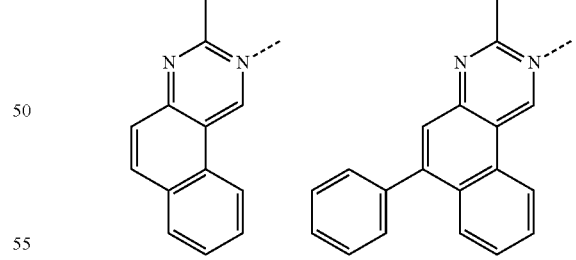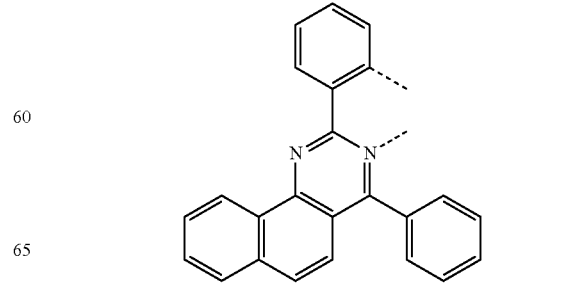

99
-continued
100
-continued
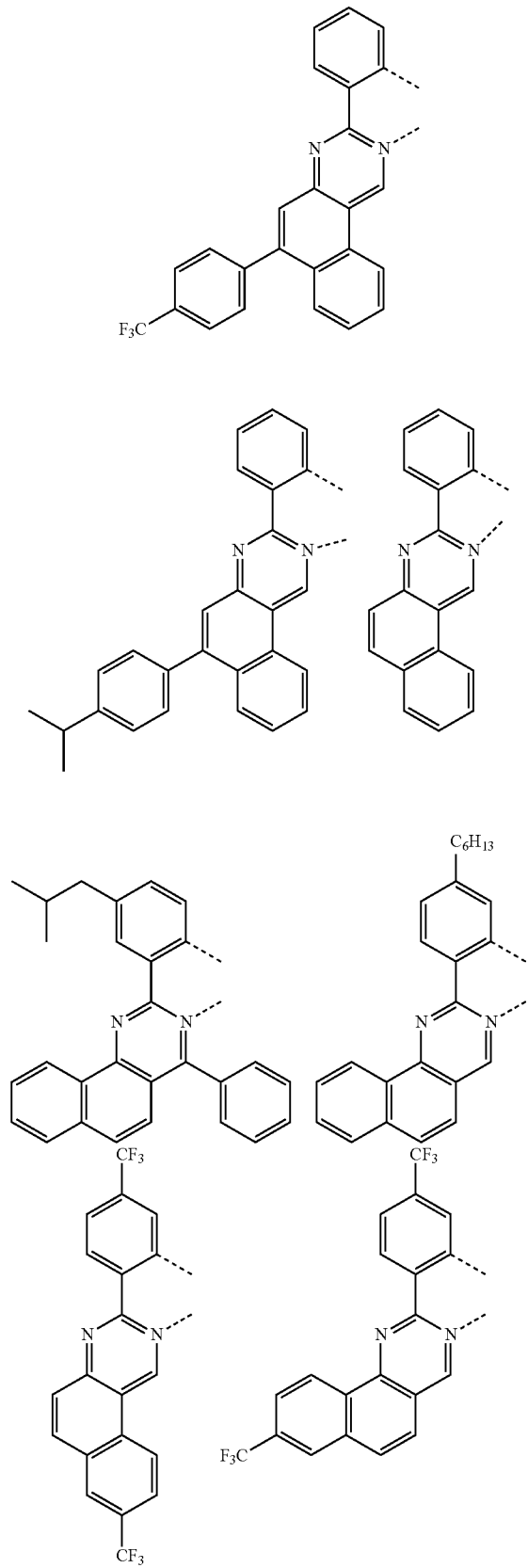
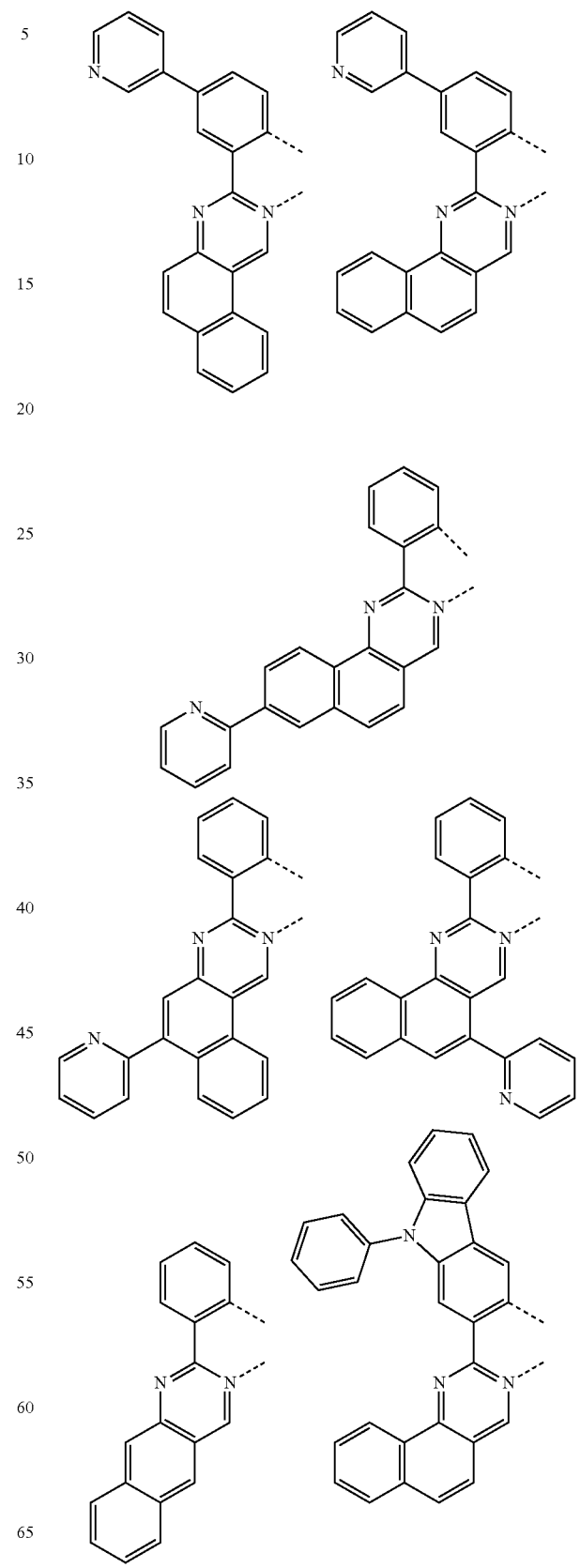

101
-continued
102
-continued
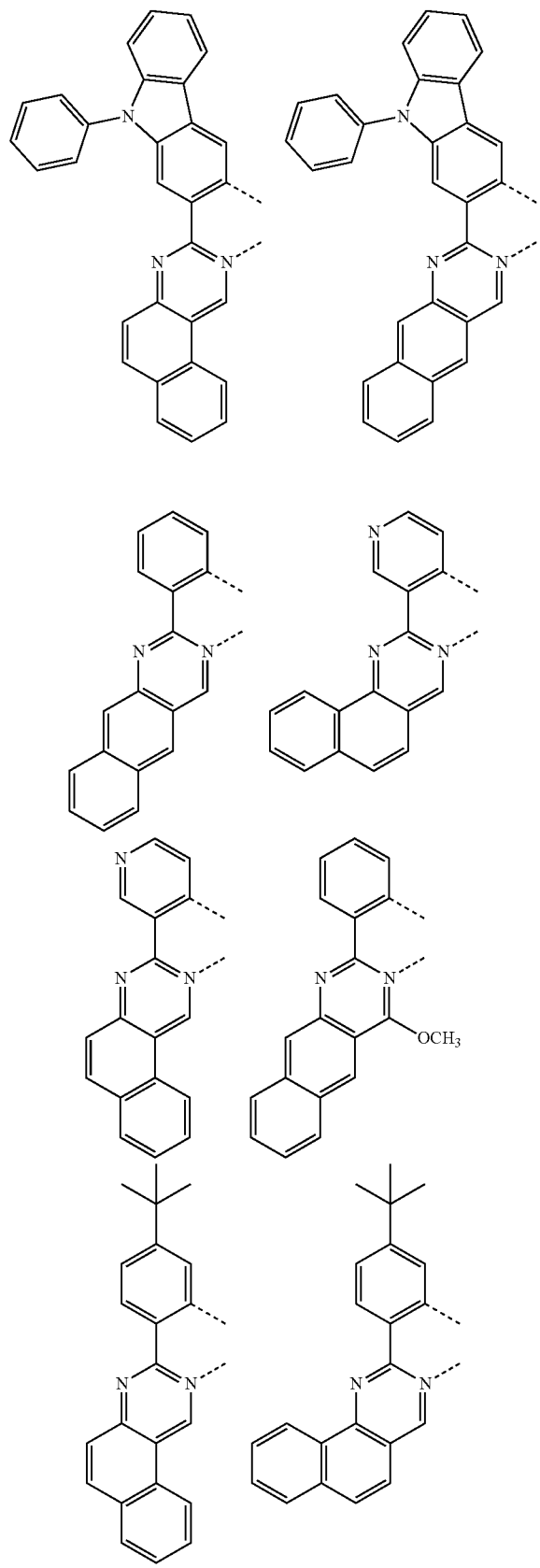
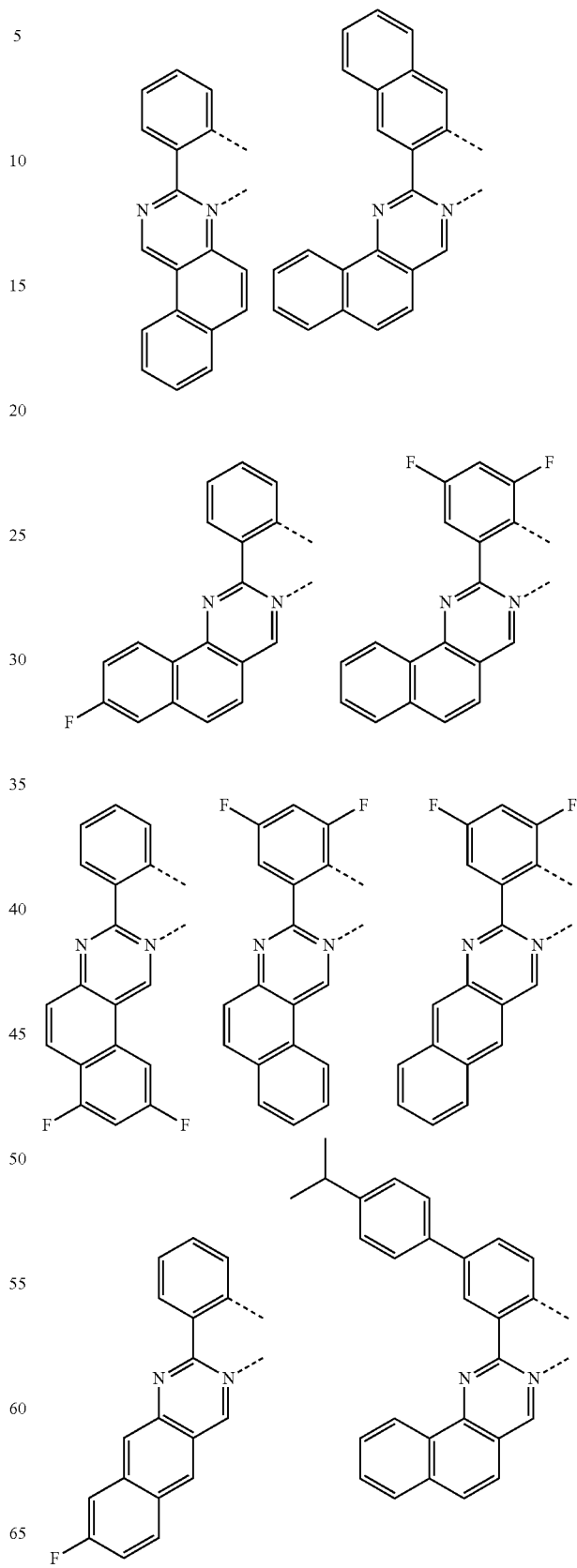

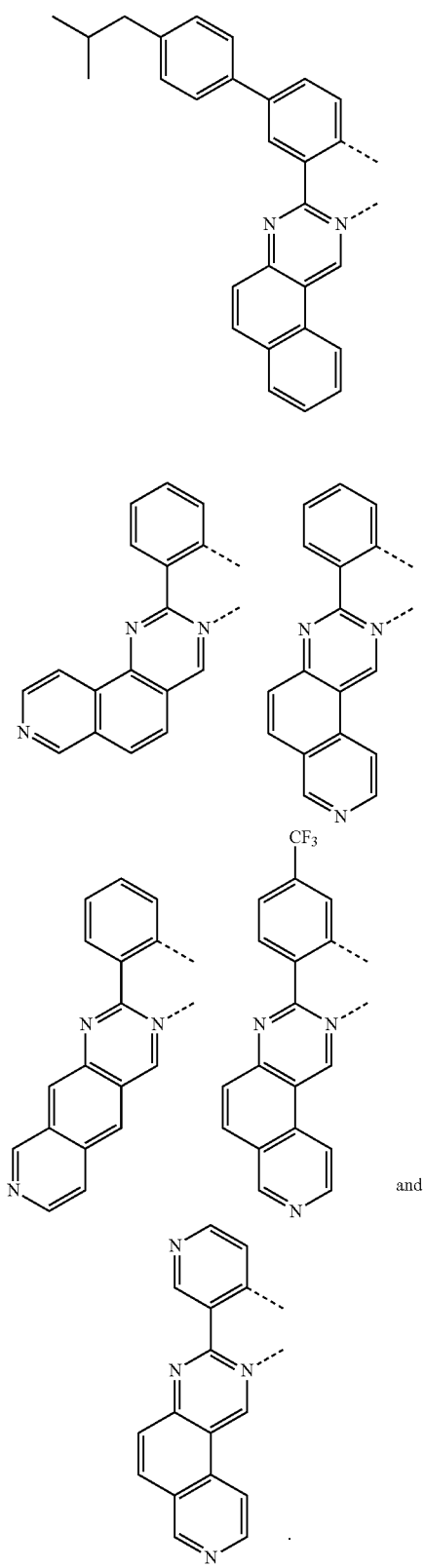

2. The compound of claim 1, wherein the second ligand is a bidentate ligand of the following formula:

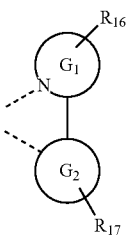

or a tautomer thereof;

wherein $G_1$ represents a hetero-monocyclic aromatic group or a hetero-polycyclic aromatic group having N as the heteroatom;

wherein $G_2$ represents a carbo-monocyclic aromatic group or a carbo polycyclic aromatic group;

wherein $R_{16}$ and $R_{17}$ independently represent mono to a maximum possible number of substitutions, or no substitution; and wherein each of $R_{16}$ or $R_{17}$ substitutions are independently selected from the group consisting of halogen, alkyl, alkoxy, aralkyl, heteroaryl, and combinations thereof.

3. The compound of claim 2, wherein the second ligand is a bidentate ligand having one of the following formulae:

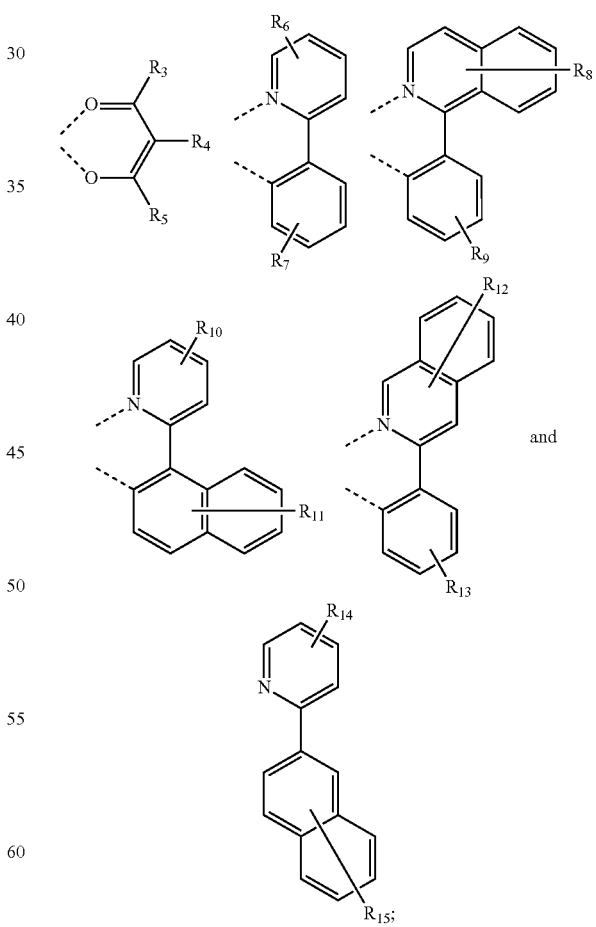

wherein $R_3$ to $R_{15}$ independently represent mono, di, tri, tetra, penta, or hexa substitutions, or no substitution; and wherein each of R₃ to R₁₅ substitutions are independently selected from the group consisting of halogen, alkyl, alkoxy, aralkyl, heteroaryl, and combinations thereof.

4. The compound of claim 3, wherein each of $R_3$ to $R_{15}$ is independently selected from the group consisting of hydrogen, alkyl having 30 or fewer carbon atoms, alkoxy having 30 or fewer carbon atoms, aryl having 30 or fewer carbon atoms, aralkyl having 30 or fewer carbon atoms, heteroaryl having 30 or fewer carbon atoms, and combinations thereof.

5. The compound of claim 4, wherein each of $R_3$ to $R_{15}$ substitutions are independently selected from the group consisting of a halogen, a methyl group, an isopropyl group, an isobutyl group, a cyclopentyl group, a hexyl group, a cyclohexyl group, a phenyl group, and combinations thereof.

6. The compound of claim 1, wherein the compound is selected from the group consisting of:

EX1
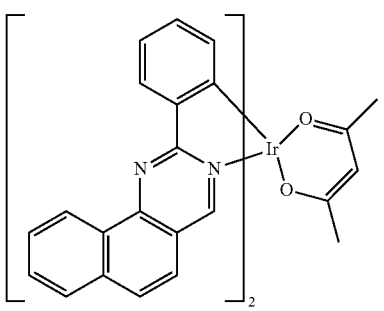

EX2
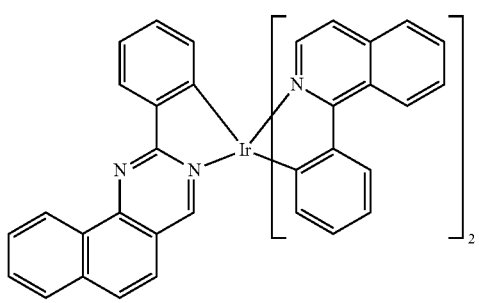

EX3
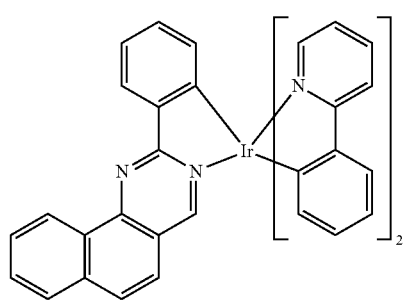

EX4
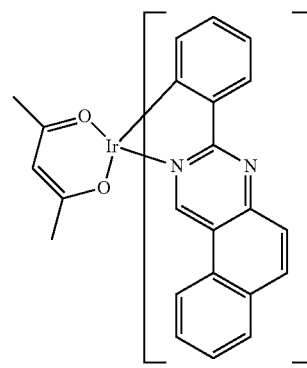

EX5
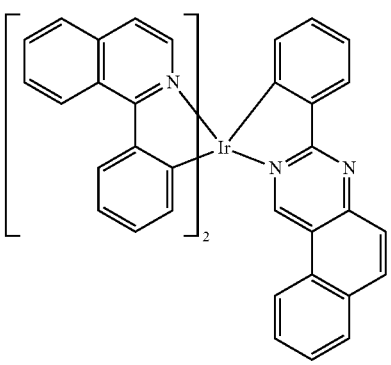

EX6
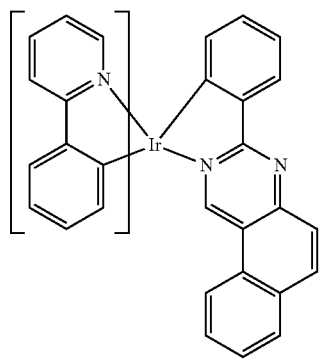

EX7
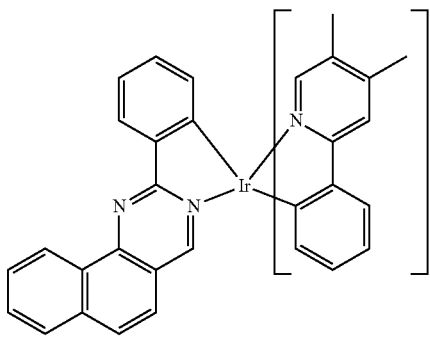

EX8
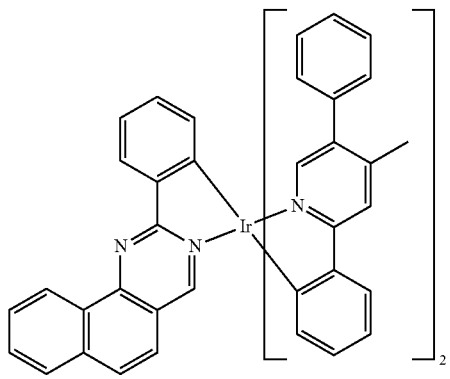
EX9
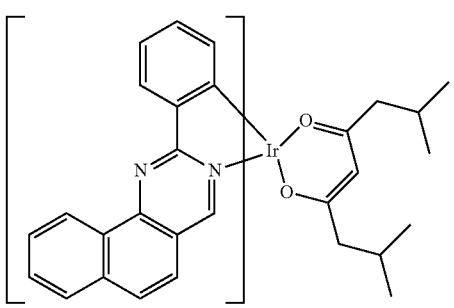
EX10
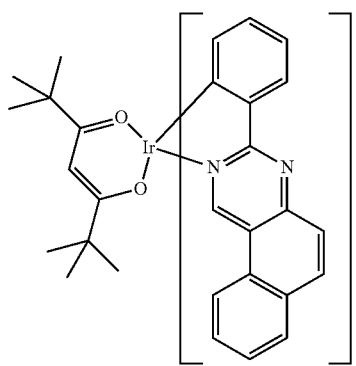
EX11
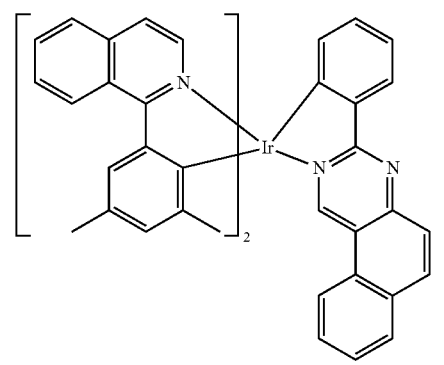
EX12
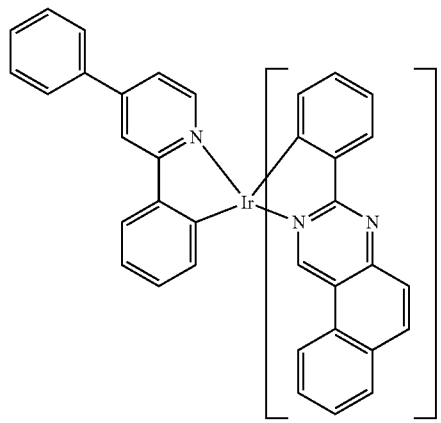
EX13
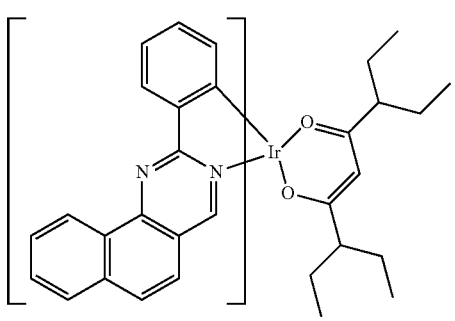
EX14
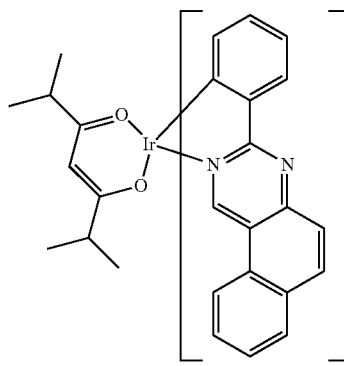
EX15
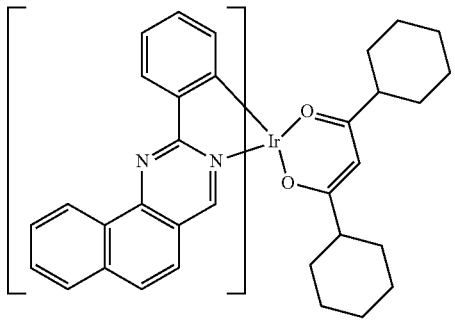

EX16
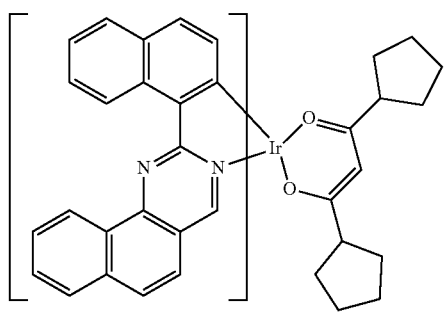
EX20
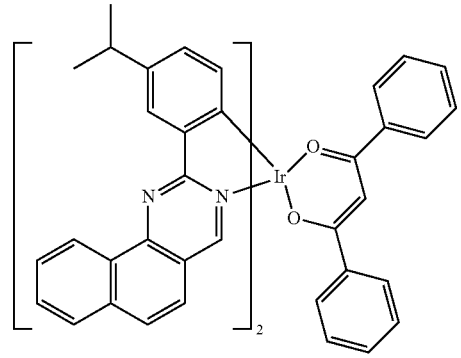
EX17
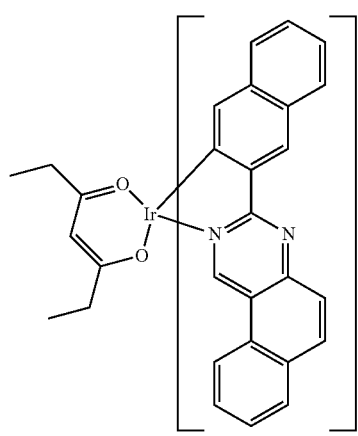
EX21
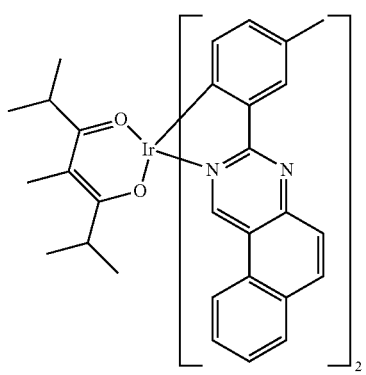
EX18
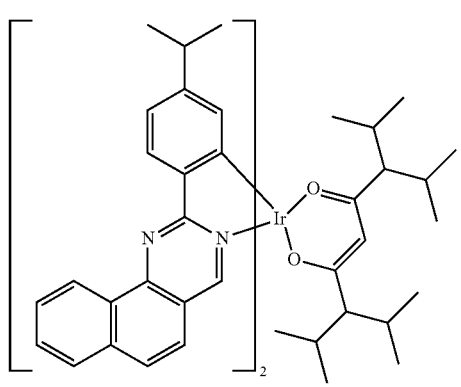
EX22
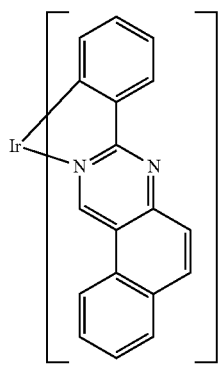
EX19
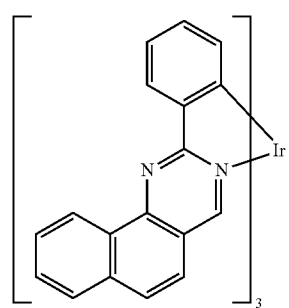
EX23
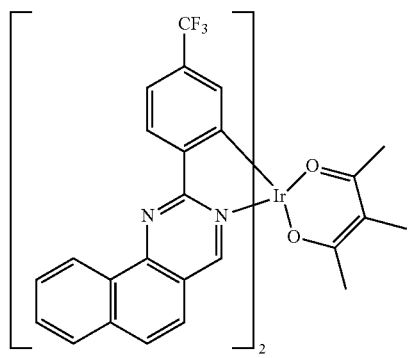

EX24
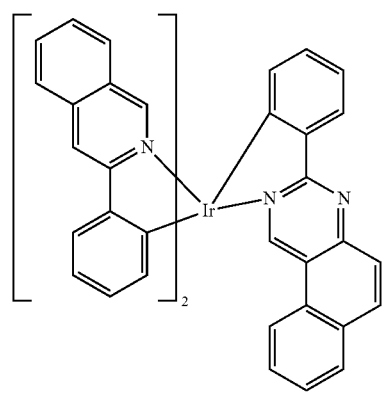
EX25
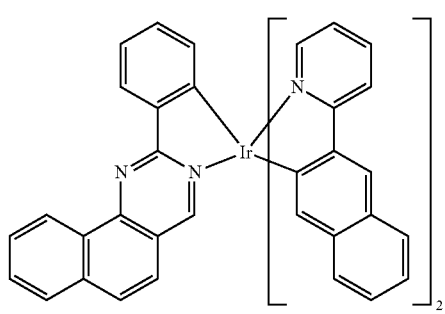
EX26
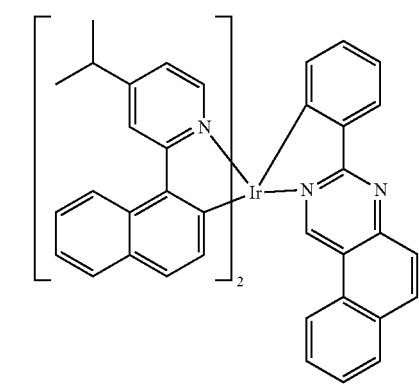
EX27
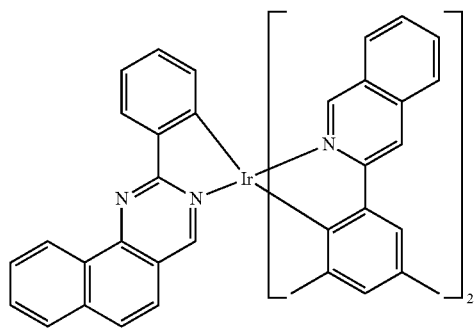
EX28
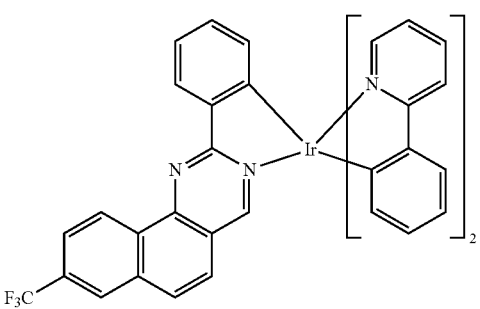
EX29
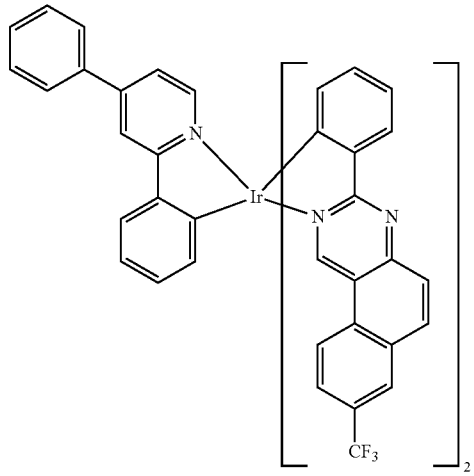
EX30
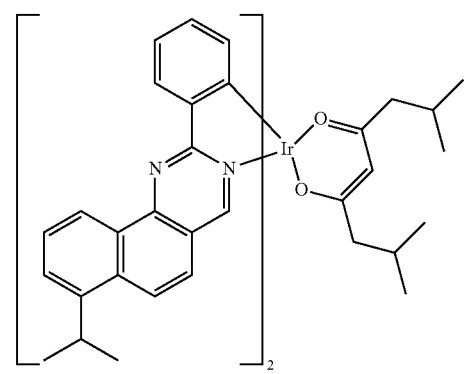
EX31
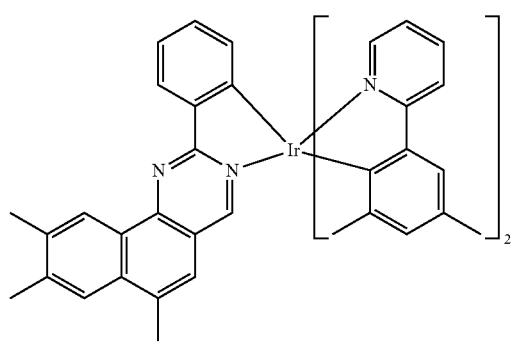

EX32
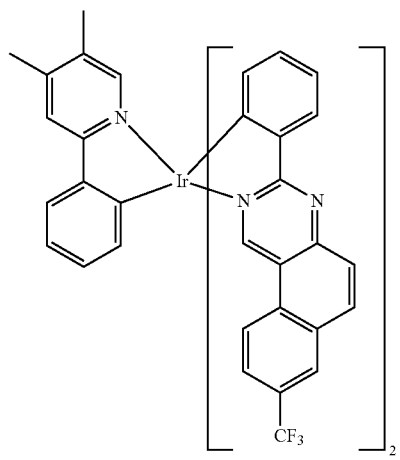
EX33
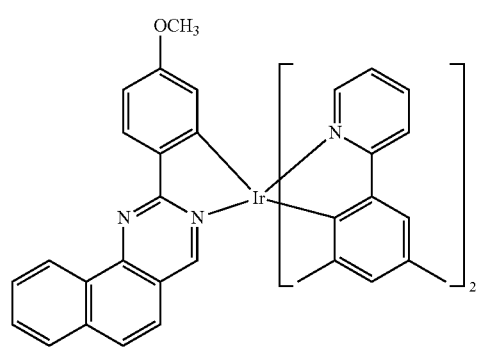
EX34
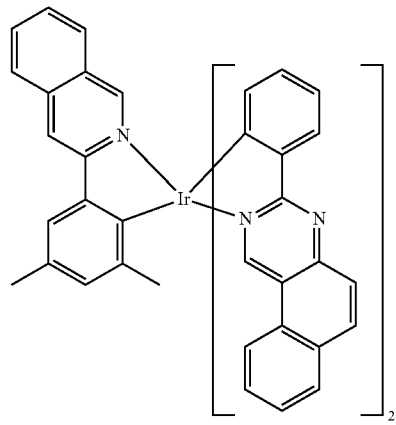
EX35
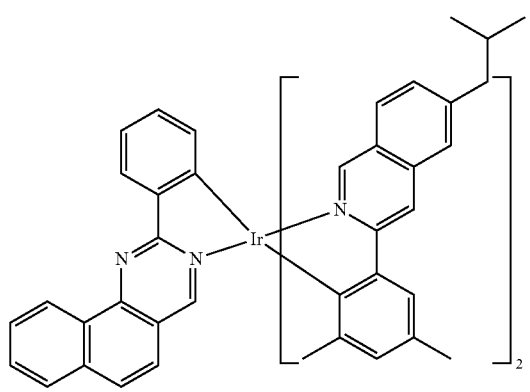
EX36
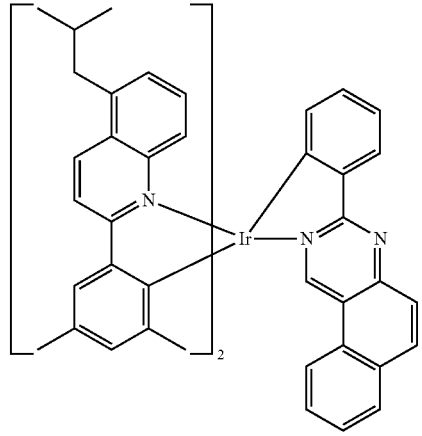
EX37
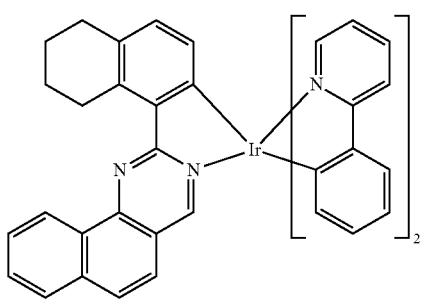
EX38
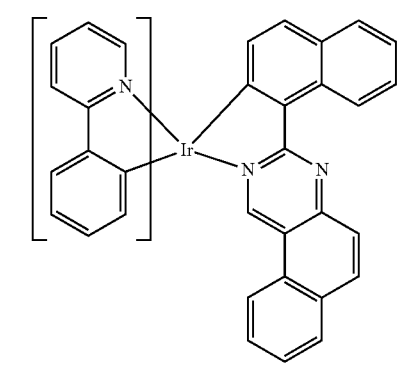
EX39
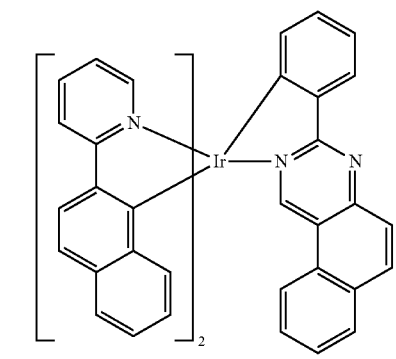

EX40
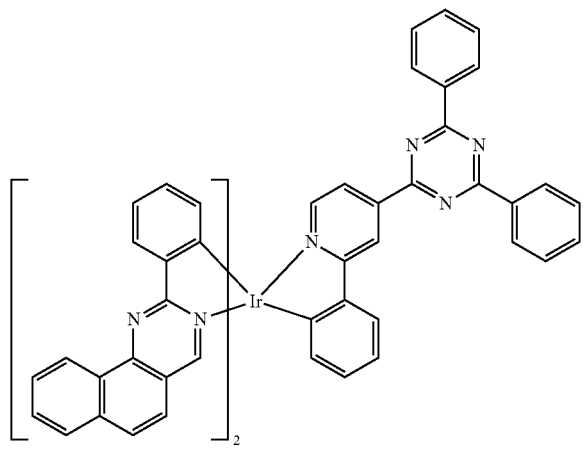
EX41
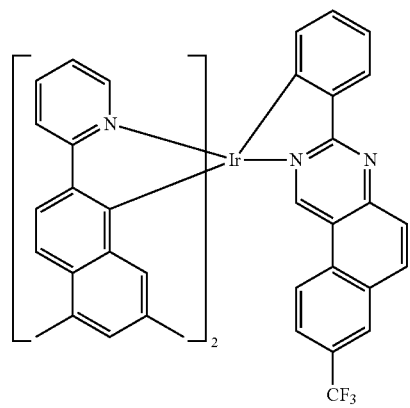
EX42
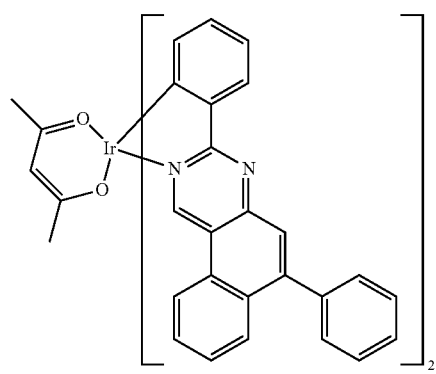
EX43
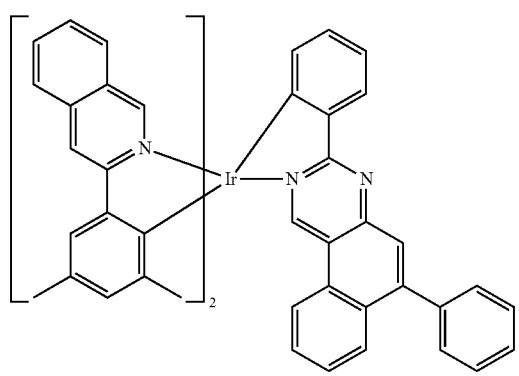
EX44
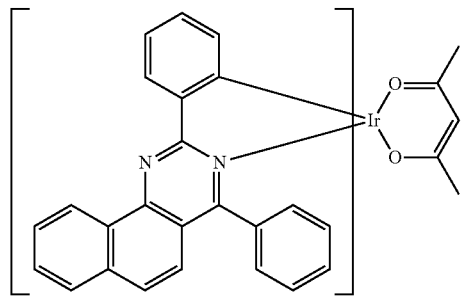
EX45
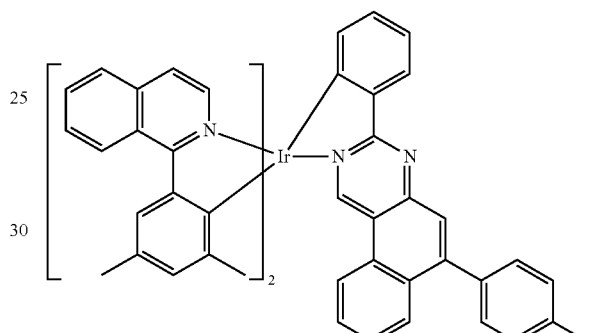
EX46
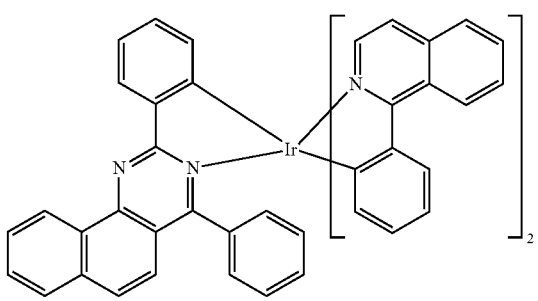
EX47
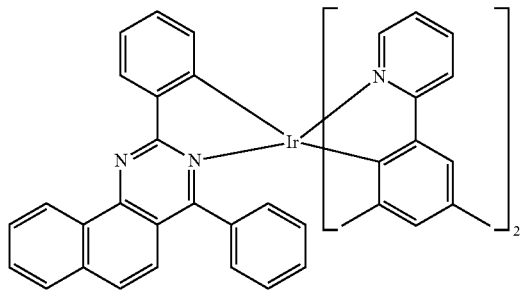

EX48
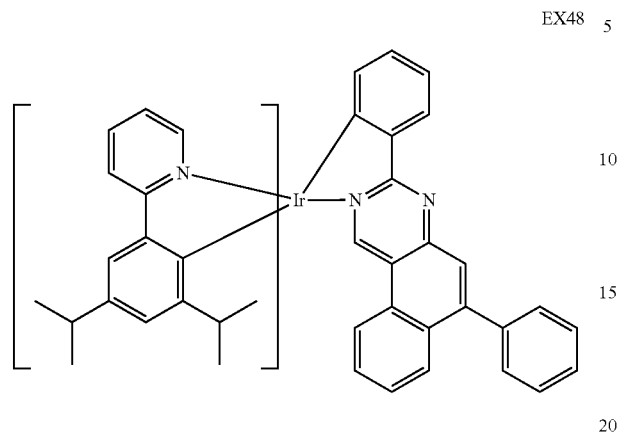
EX49
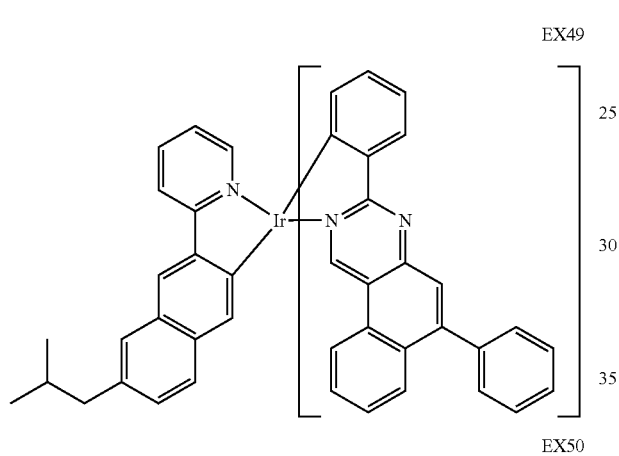
EX50
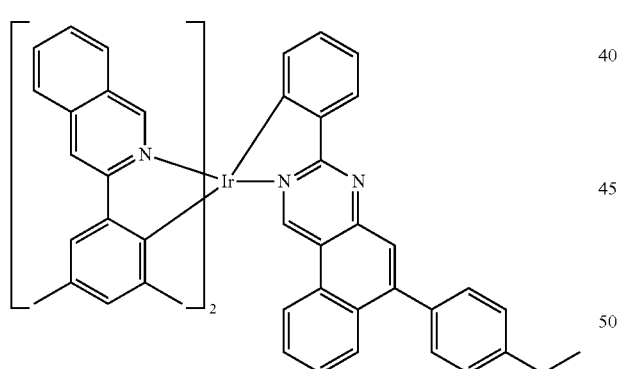
EX51
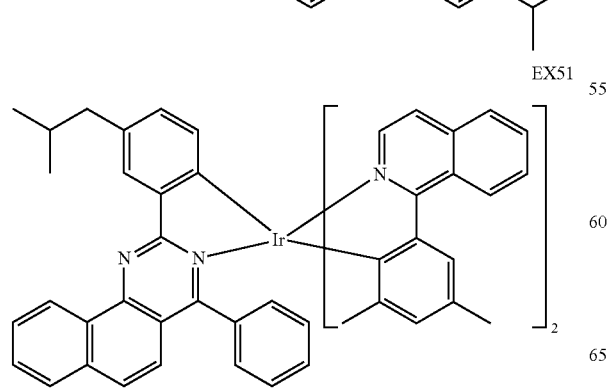
EX52
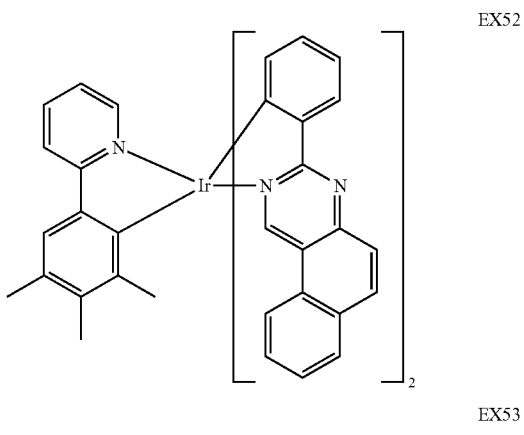
EX53
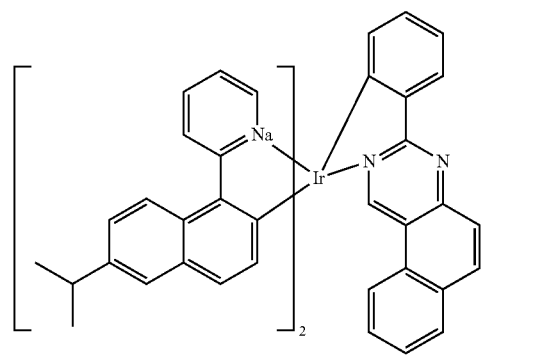
EX54
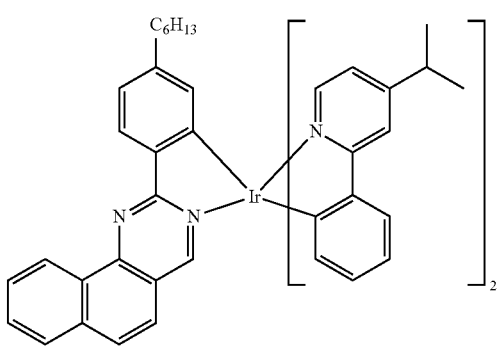
EX55

EX56
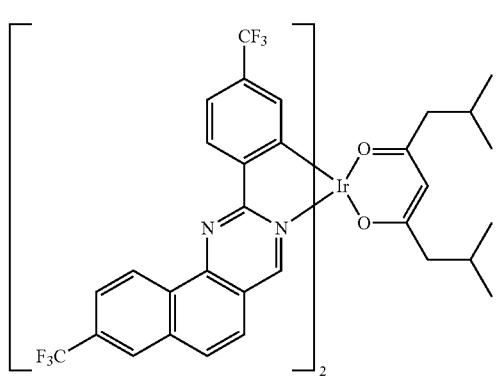
EX60
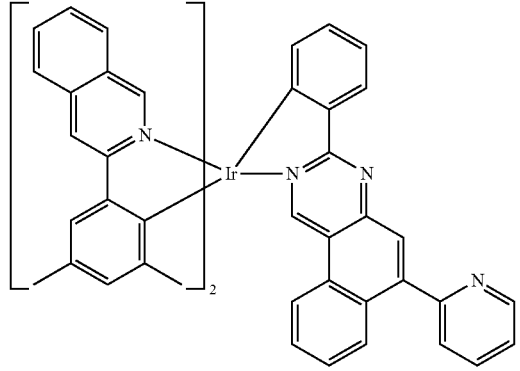
EX57
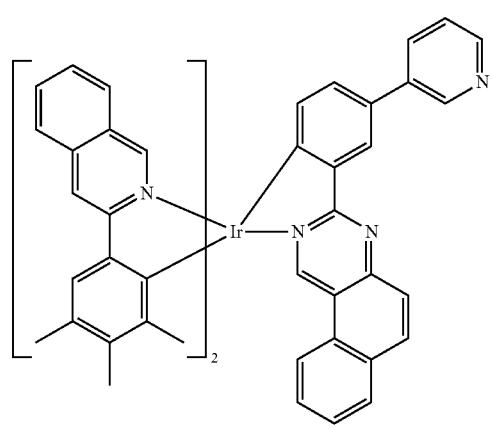
EX61
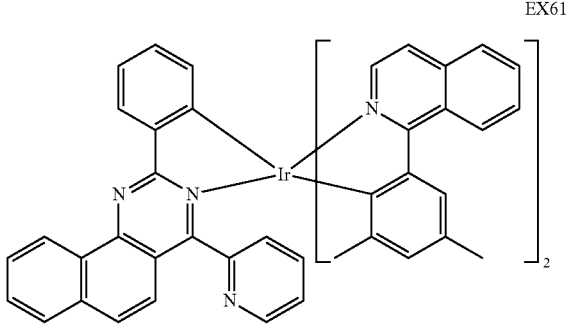
EX58
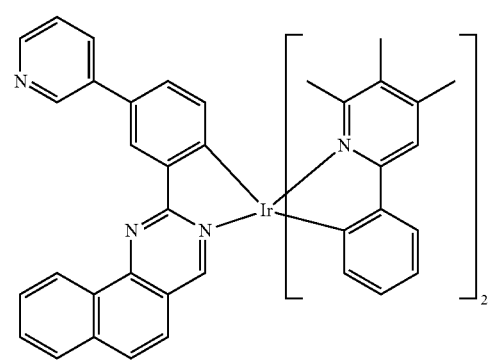
EX62
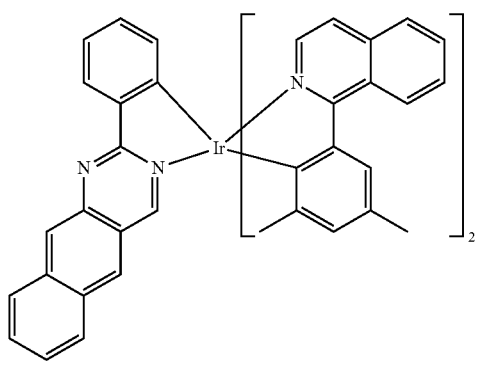
EX59
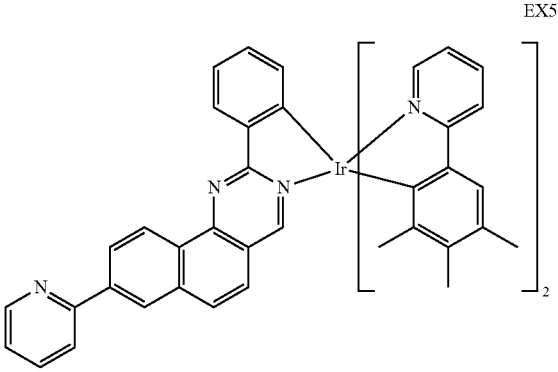
EX63
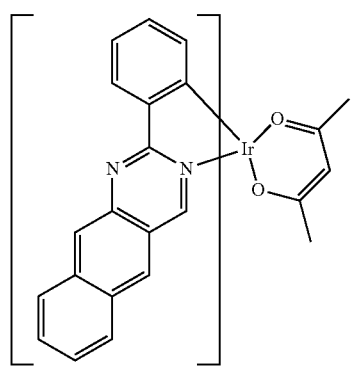

EX64
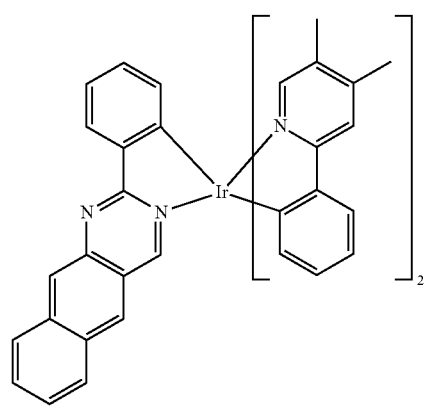
EX65
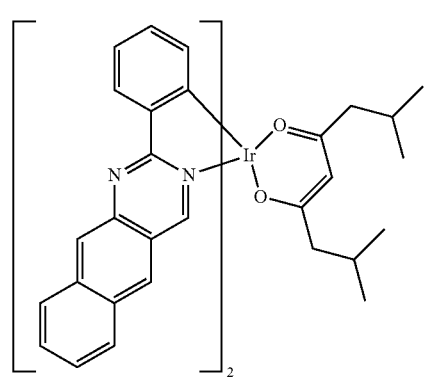
EX66
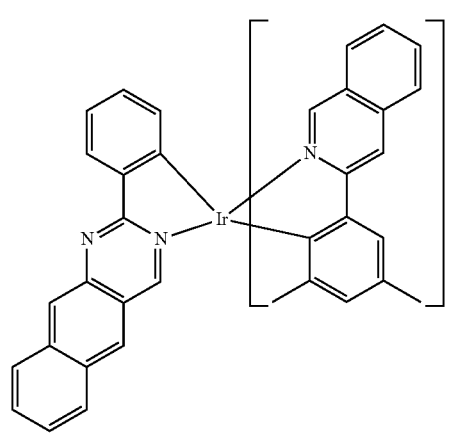
EX67
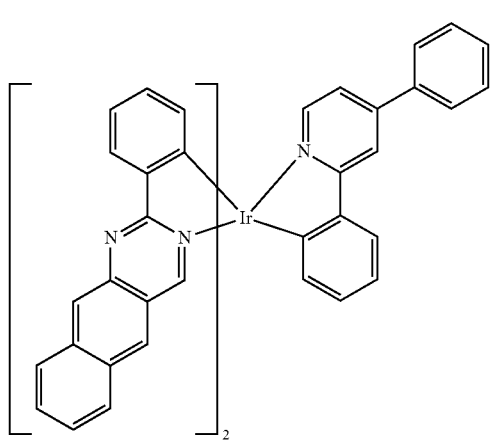
EX68
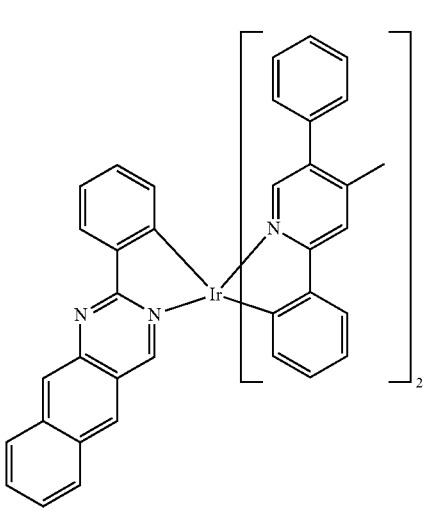
EX69
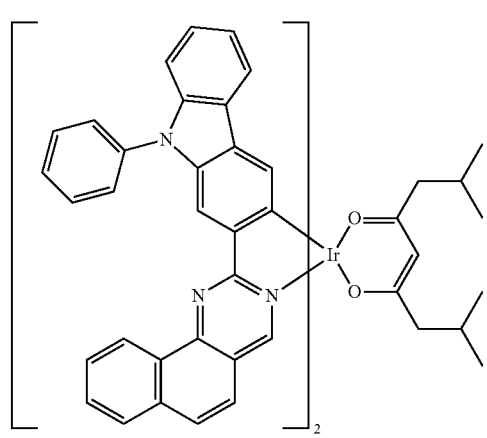
EX70
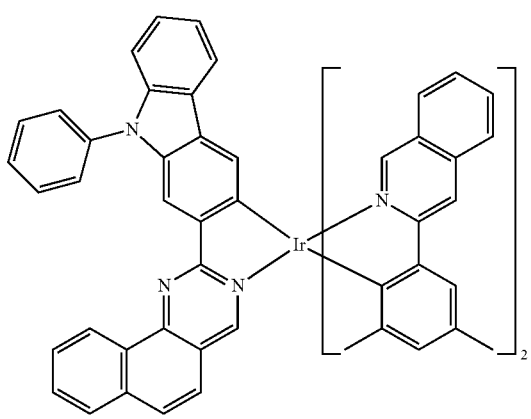

123
-continued
EX71
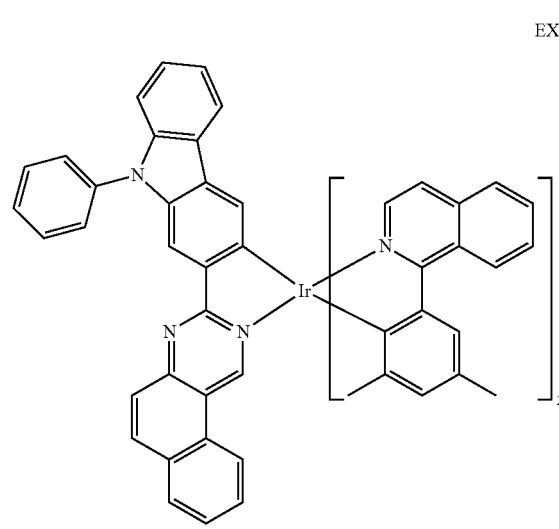
EX72
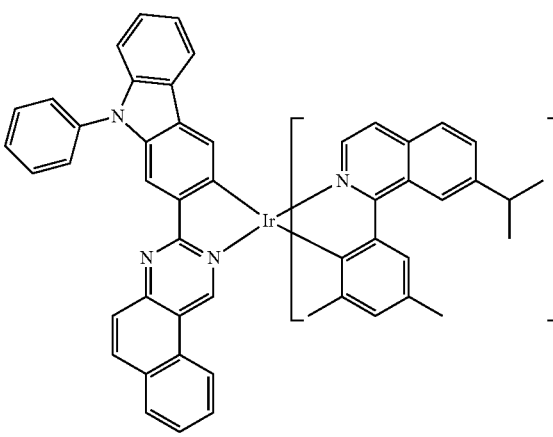
EX73
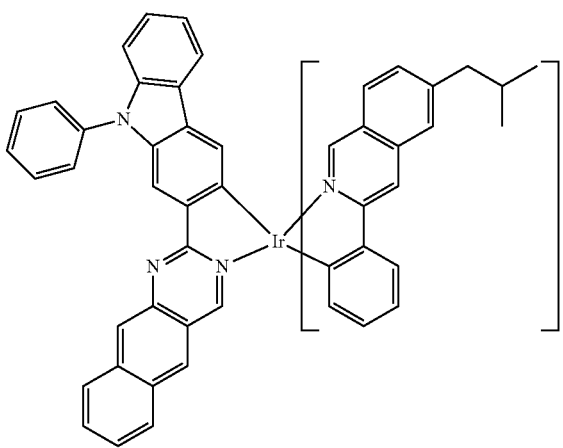
124
-continued
EX74
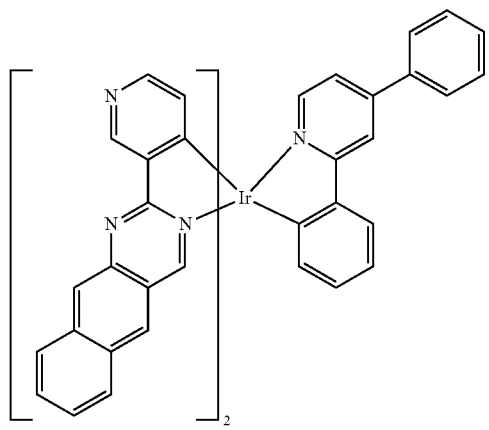
EX75
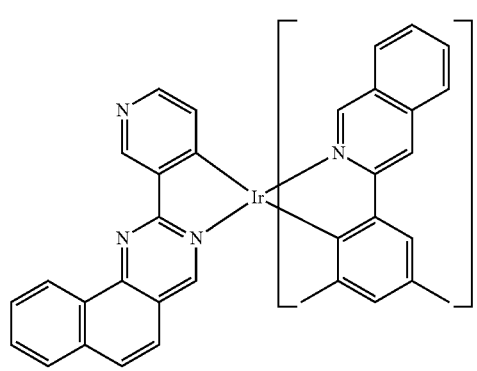
EX76
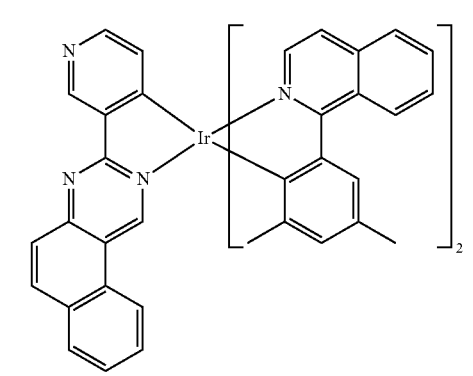
EX77
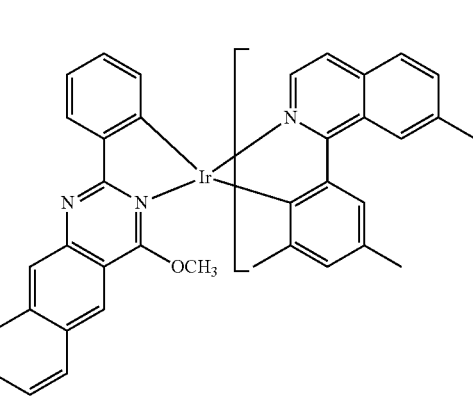

EX78
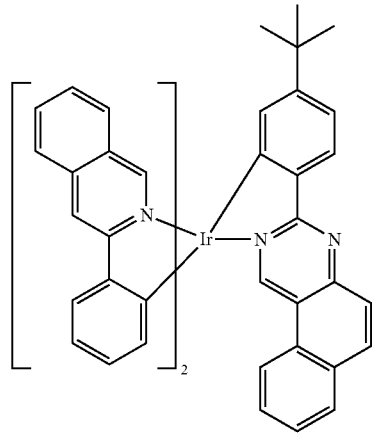
EX79
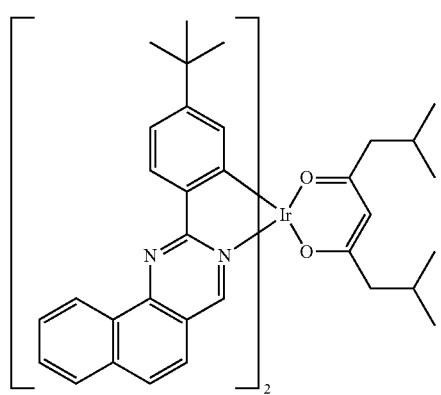
EX80
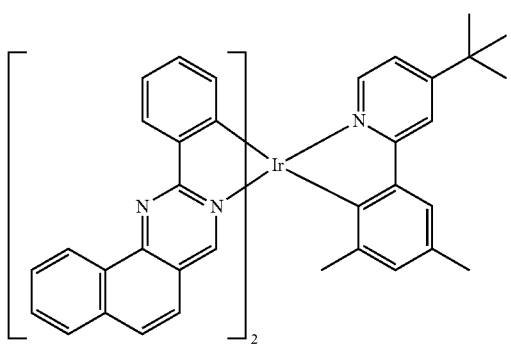
EX81
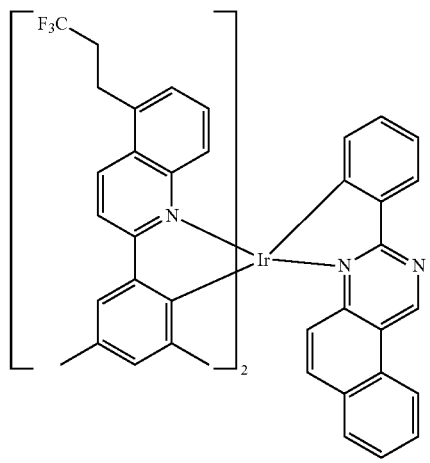
EX82
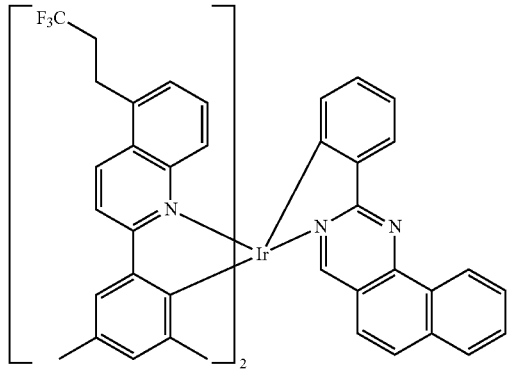
EX83
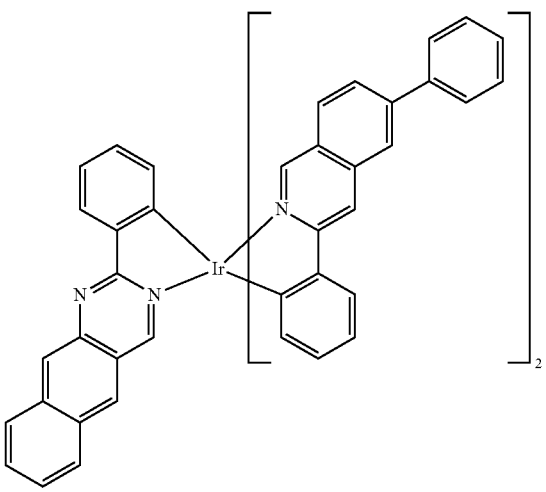
EX84
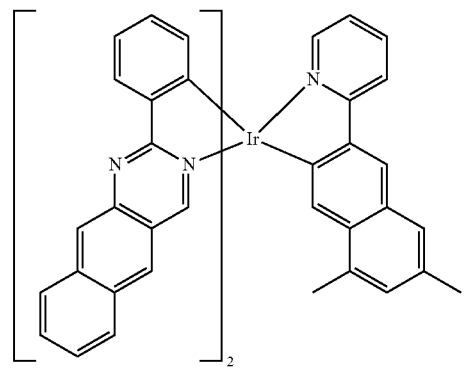

-continued
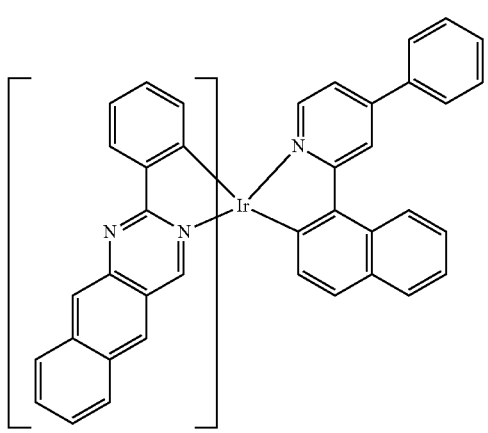
EX85
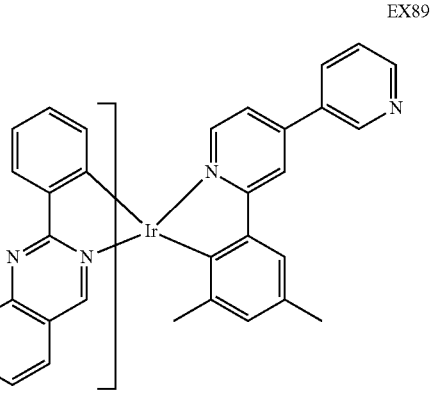
EX89
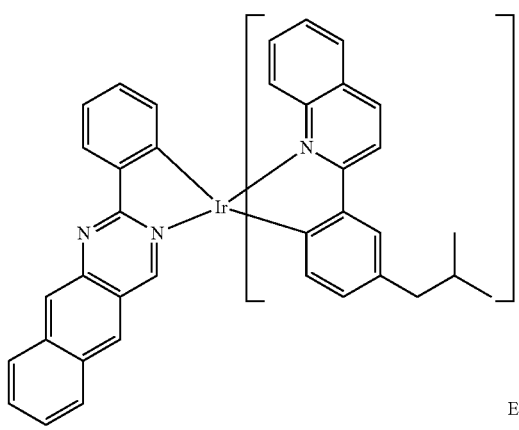
EX86
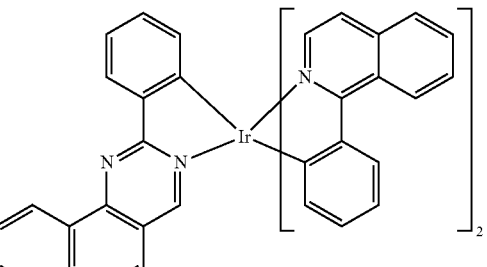
EX90
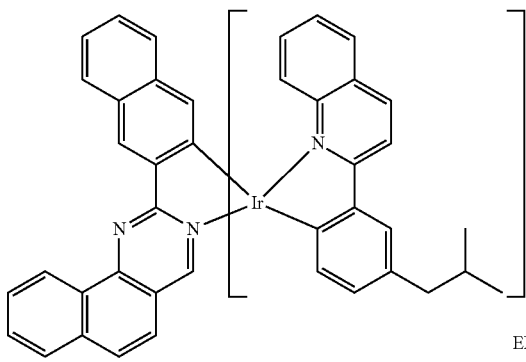
EX87
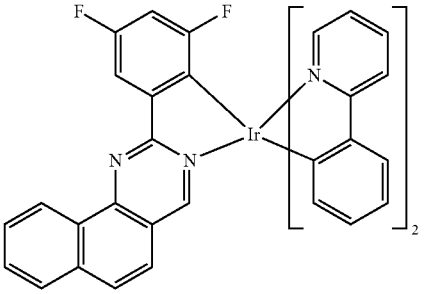
EX91
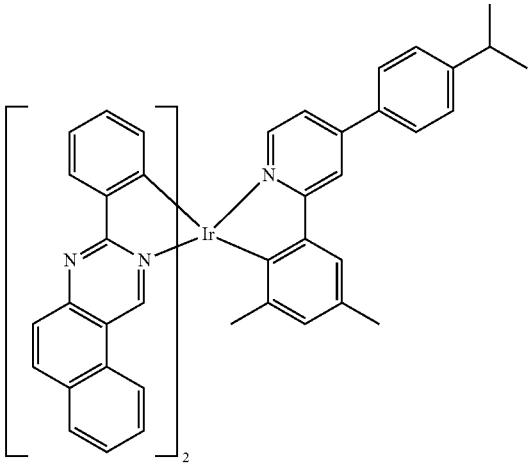
EX88
EX92

EX93
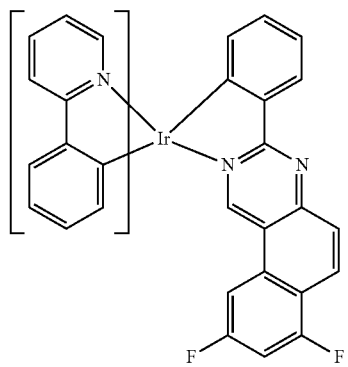
EX94
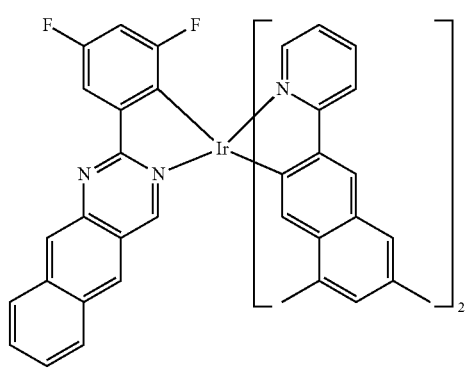
EX95
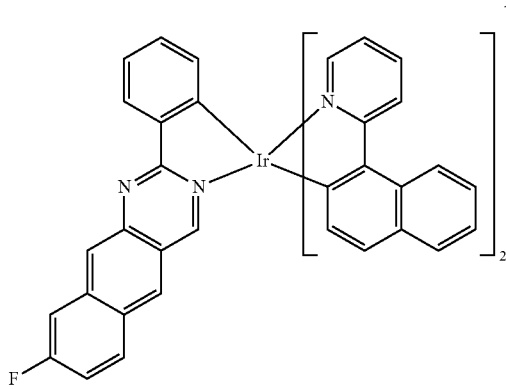
EX96
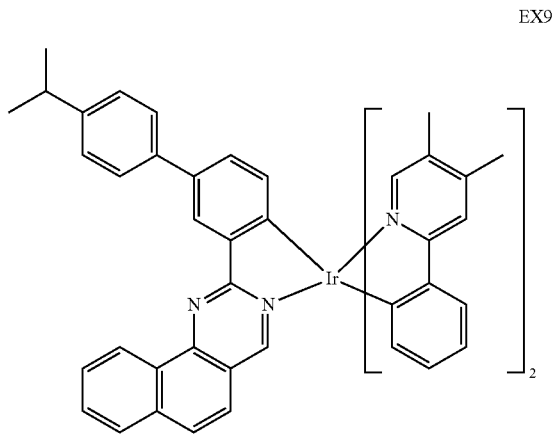
EX97
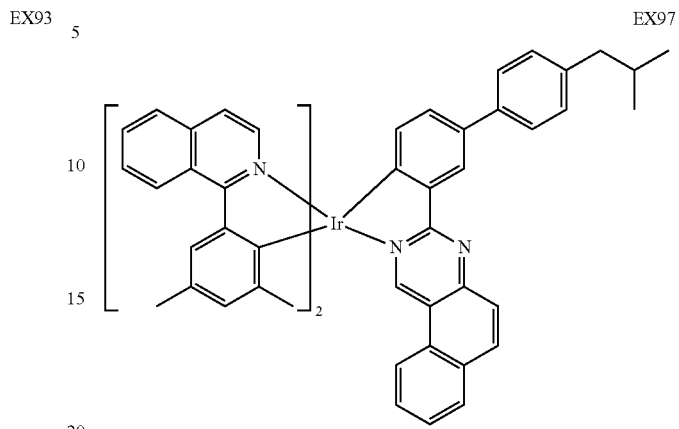
EX98
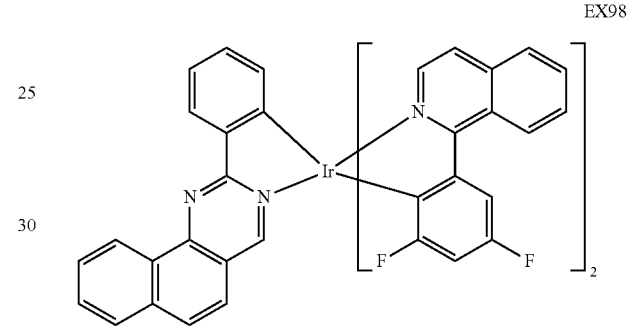
EX99
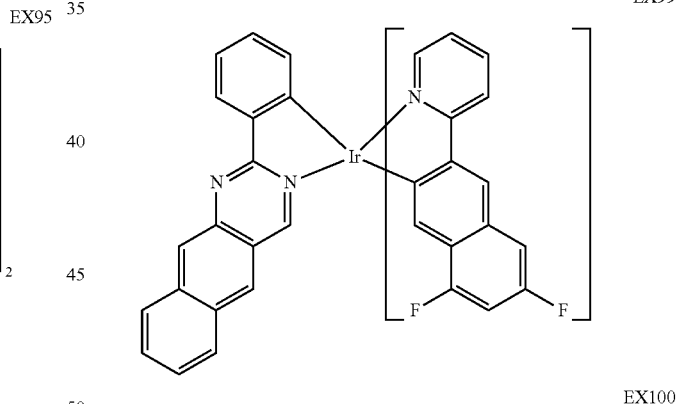
EX100
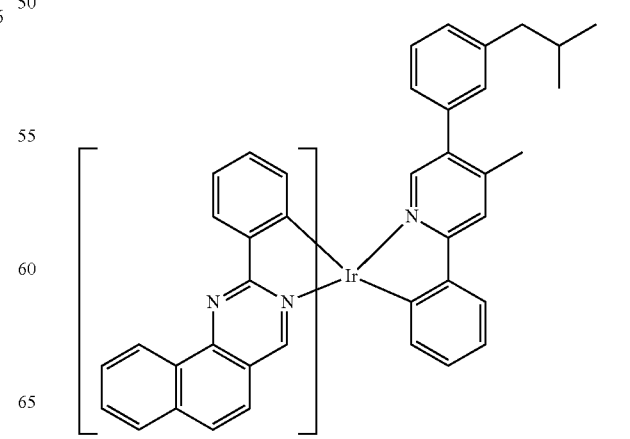

EX101 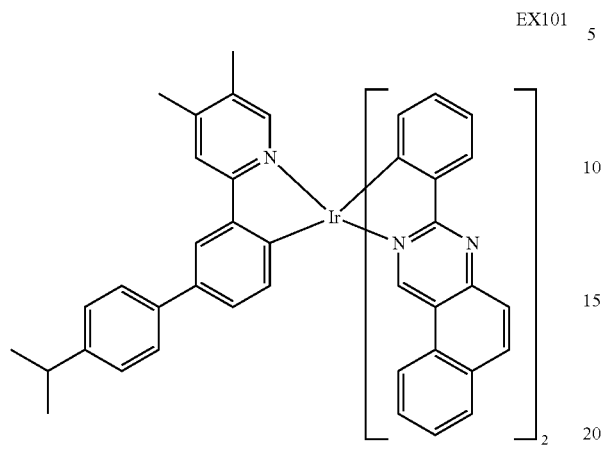
EX102 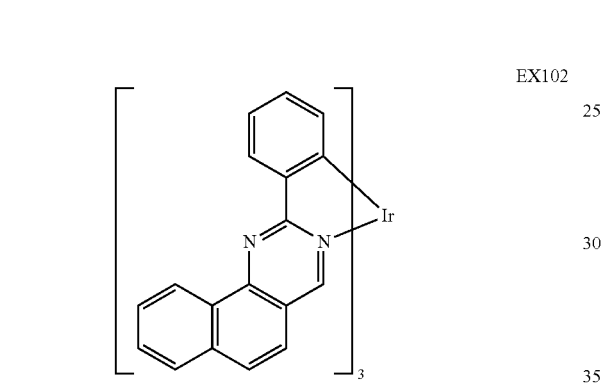
EX103 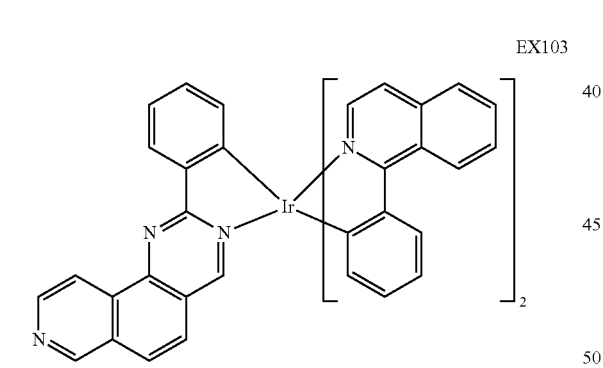
EX104 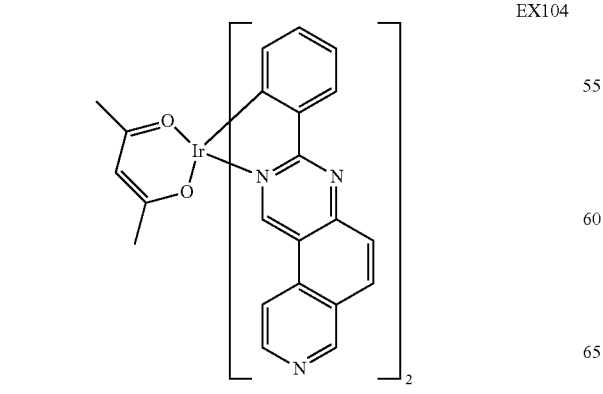
EX105 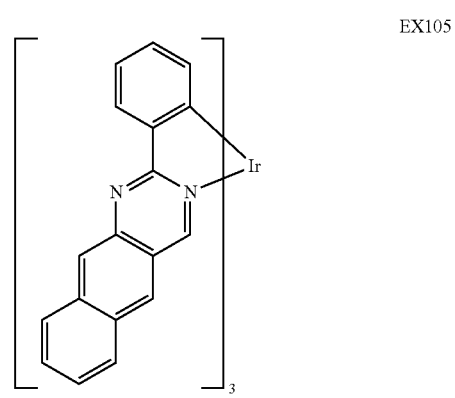
EX106 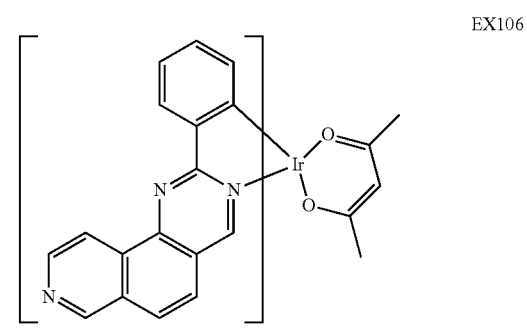
EX107 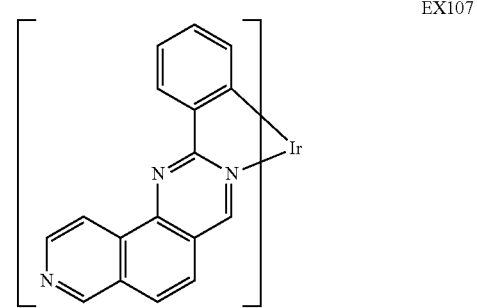
EX108 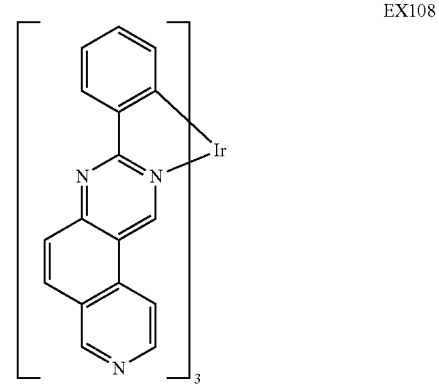

EX109
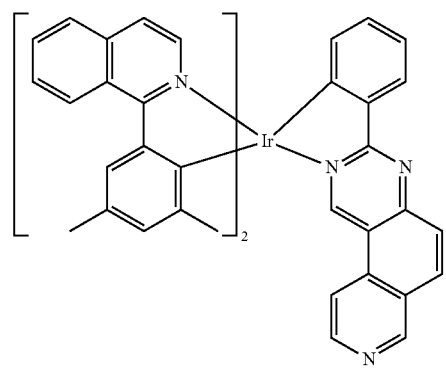
EX110
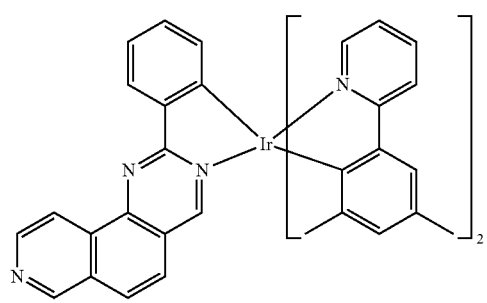
EX111
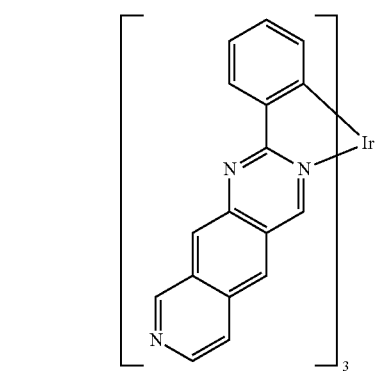
EX112
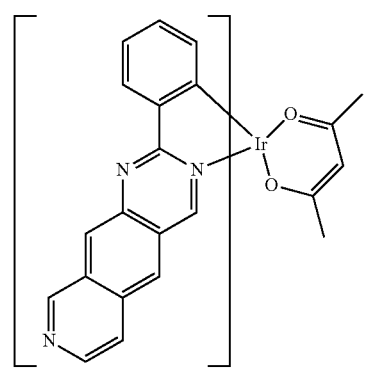
EX113
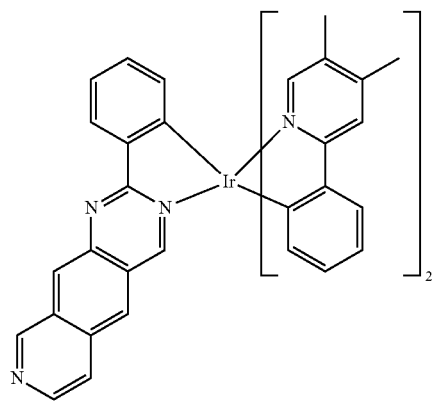
EX114
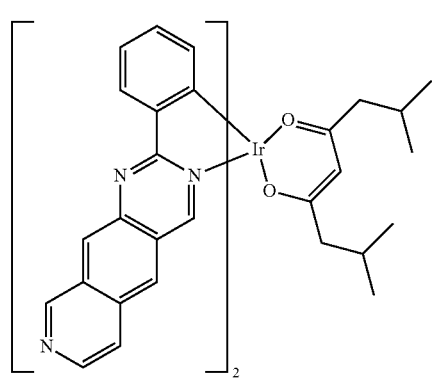
EX115
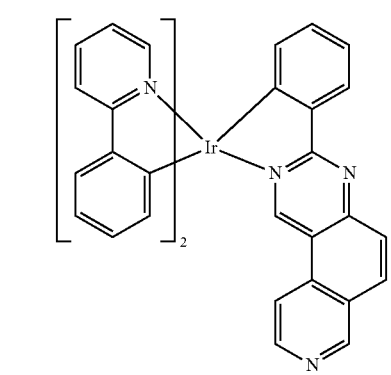
EX116
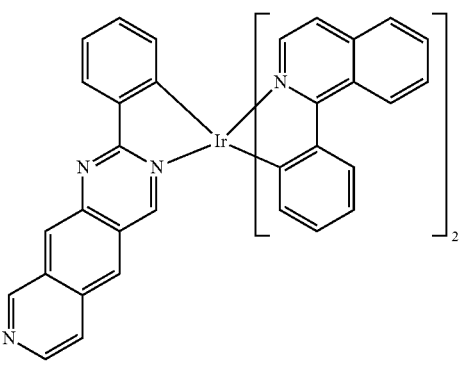

-continued
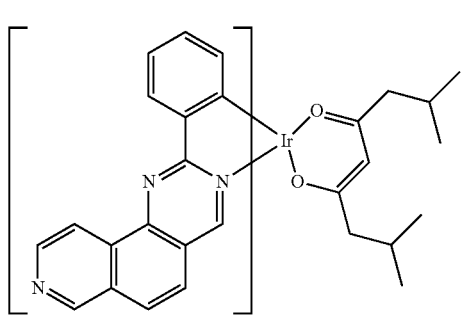
EX117
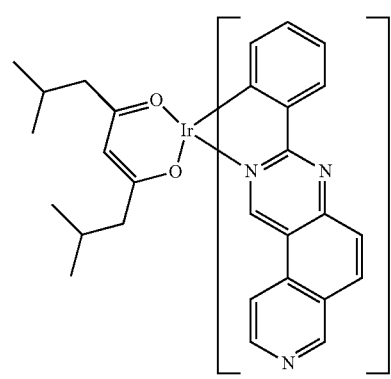
EX118
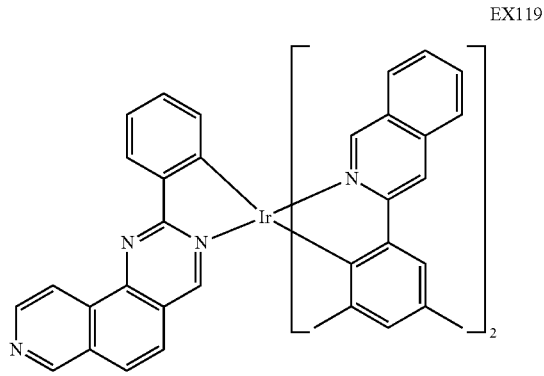
EX119
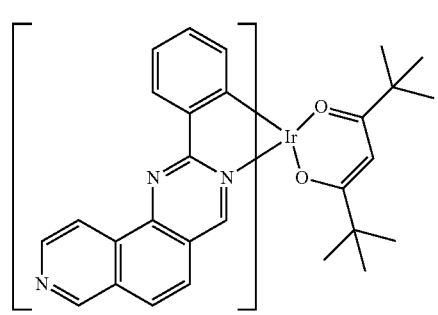
EX120
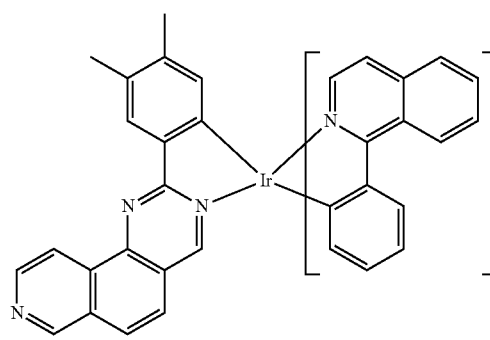
EX121
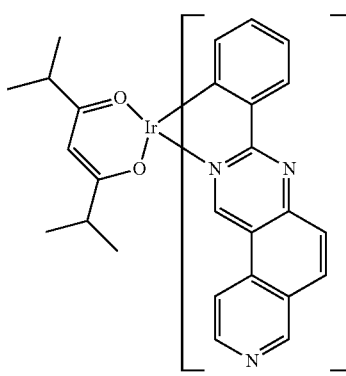
EX122
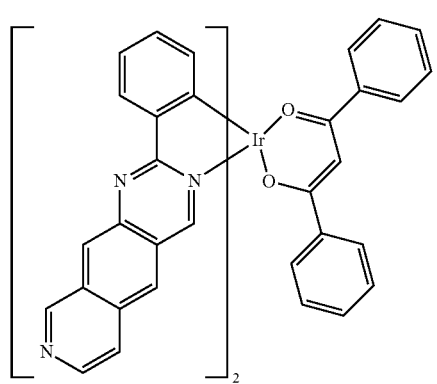
EX123
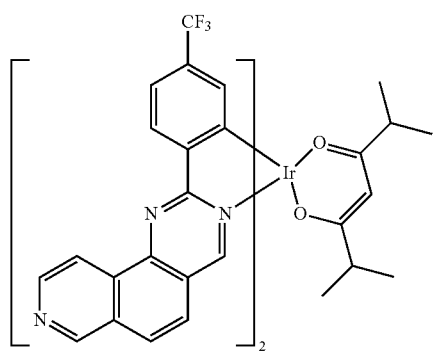
EX124

EX125
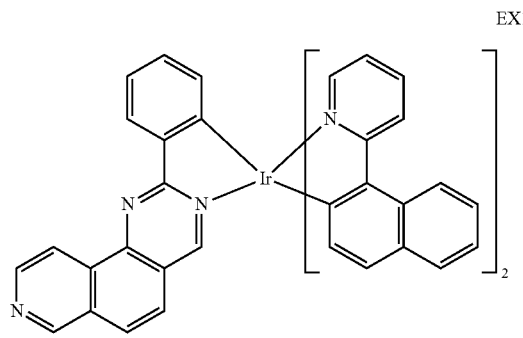
EX129
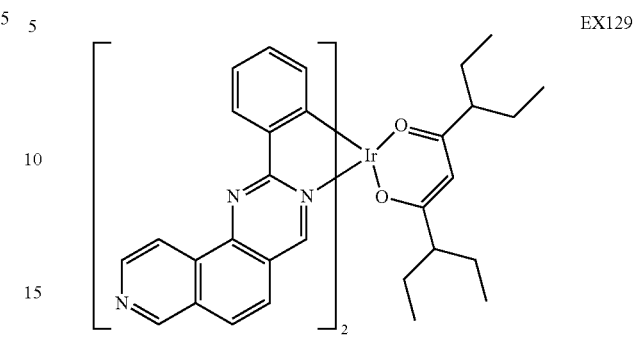
EX126
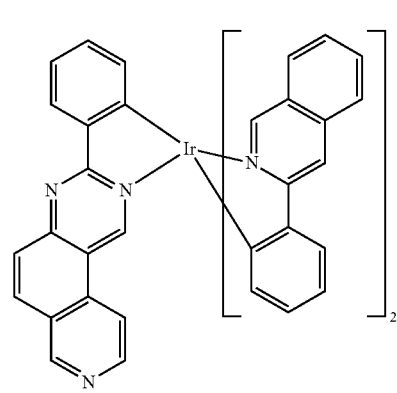
EX130
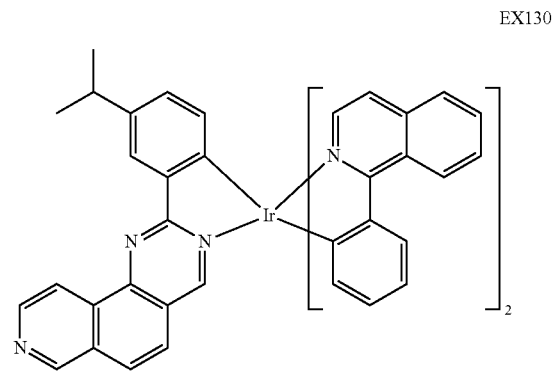
EX127
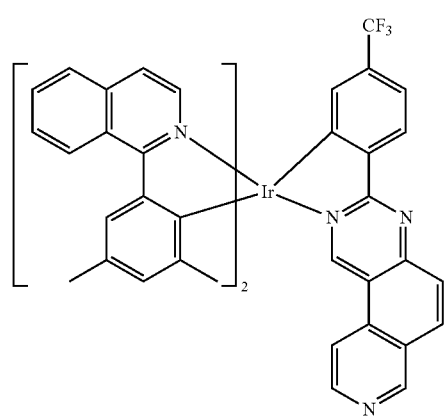
EX131
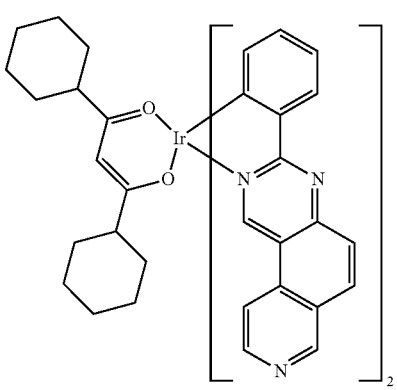
EX128
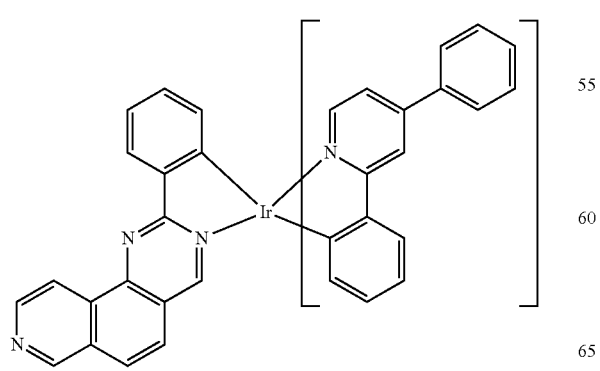
EX132
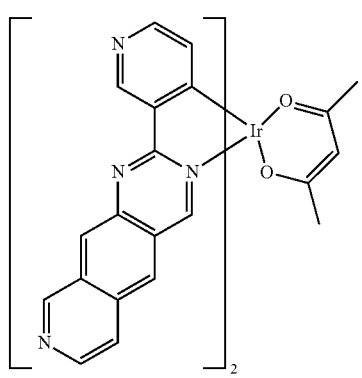

EX133

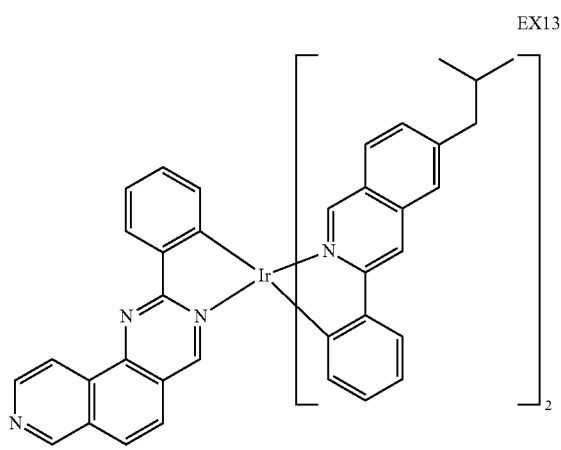

EX134

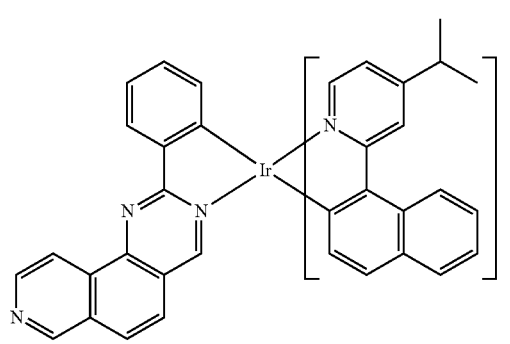

EX135

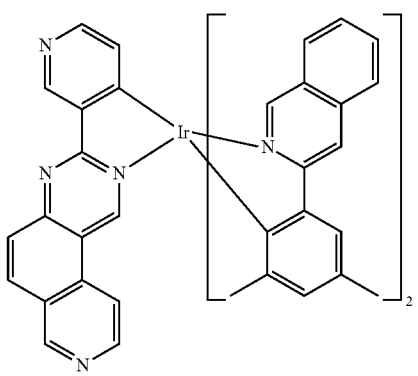

EX136

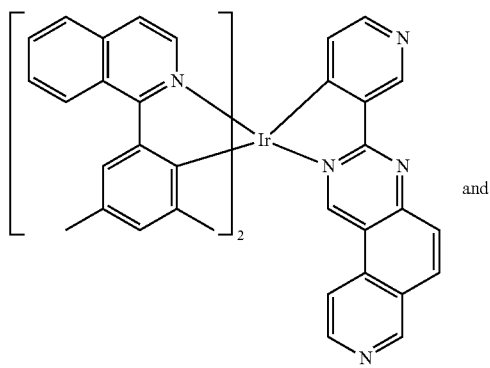

and

EX137

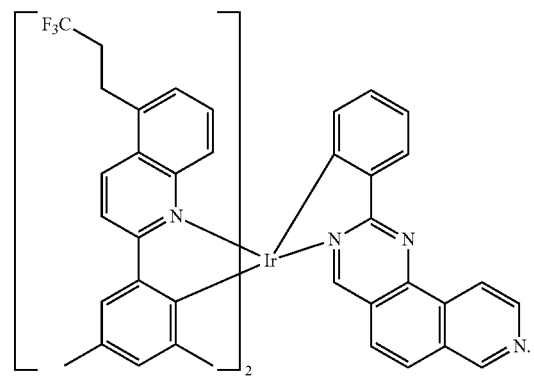

7. An organic electroluminescence device comprising a cathode, an anode and one or more organic layers formed between the anode and the cathode, wherein at least one of the organic layers comprises the compound of claim 1.

8. The organic electroluminescence device of claim 7, wherein the compound is comprised as a phosphorescent dopant material.

9. The organic electroluminescence device of claim 7, wherein the one of the organic layers comprising the compound is an emissive layer emitting green, yellow or red phosphorescence.

10. The organic electroluminescence device of claim 7, wherein the organic electroluminescence device is a panel free of blue wavelengths.

11. The organic electroluminescence device of claim. 7, wherein the organic electroluminescence device is a lighting panel.

12. The organic electroluminescence device of claim 7, wherein the organic electroluminescence device is a backlight panel.

13. An organic electroluminescence device comprising a cathode, an anode and one or more organic layers formed between the anode and the cathode, wherein at least one of the organic layers comprises an compound comprising a first ligand of the following formula;

formula (2)

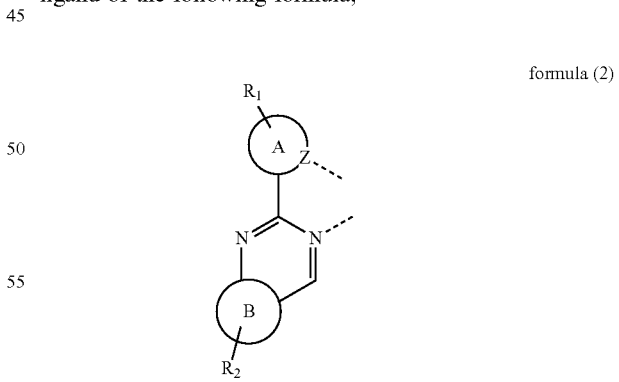

or a tautomer thereof;
    wherein ring A represents a monocyclic aromatic group or a polycyclic aromatic group:
    wherein ring B represents a polycyclic aromatic group;
    wherein Z is a carbon.
    wherein Z and the right N are coordinated to a metal to form a five-membered chelate ring;

wherein $R_1$ and $R_2$ independently resent mono to a maximum possible number of substitutions, or no substitution;

wherein $R_1$ and $R_2$ are each independently a hydrogen or a substituent selected from the group consisting of halide, alkyl, alkoxy, aralkyl, heteroaryl, deuterium, cycloalkyl, heteroalkyl, aryl, alkyl, alkoxy, aryloxy, amino, silyl, alkenyl, cycloalkenyl, heteroalkenyl, alkenyl, acyl, carbonyl, carboxylic acids, ester, nitrile, isonitrile, sulfanyl, sulfinyl, sulfonyl, phosphino, and combinations thereof;

wherein two or more of adjacent $R_1$ or $R_2$ substituents are optionally joined or fused into a ring;

wherein the metal is optionally coordinated to a second ligand; and wherein the organic electroluminescence device is an amber panel.

* * * * *